(12) United States Patent
Castro et al.

(10) Patent No.: US 11,807,633 B2
(45) Date of Patent: *Nov. 7, 2023

(54) CHROMENE DERIVATIVES AS INHIBITORS OF TCR-NCK INTERACTION

(71) Applicant: Artax Biopharma Inc., Cambridge, MA (US)

(72) Inventors: Julio Castro, Barcelona (ES); Andrés Gagete Mateos, Valencia (ES); Peter J. Machin, London (GB); Christopher Loren Vandeusen, Hopkinton, MA (US)

(73) Assignee: Artax Biopharma Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/240,041

(22) Filed: Apr. 26, 2021

(65) Prior Publication Data

US 2022/0081429 A1    Mar. 17, 2022

Related U.S. Application Data

(63) Continuation of application No. 16/878,842, filed on May 20, 2020, now Pat. No. 11,008,310, which is a
(Continued)

(51) Int. Cl.
*C07D 413/06* (2006.01)
*C07D 311/22* (2006.01)
(Continued)

(52) U.S. Cl.
CPC .............. *C07D 413/06* (2013.01); *A61P 3/10* (2018.01); *A61P 11/06* (2018.01); *A61P 17/00* (2018.01);
(Continued)

(58) Field of Classification Search
CPC .. C07D 413/06; C07D 311/22; C07D 311/58; C07D 405/06; C07D 405/12;
(Continued)

(56) References Cited

U.S. PATENT DOCUMENTS 7,060,827 B2    6/2006    Singh et al.
7,390,799 B2    6/2008    Bruncko et al.
(Continued)

FOREIGN PATENT DOCUMENTS

CN    104844471 A    8/2015
EP    2354134 A1    8/2011
(Continued)

OTHER PUBLICATIONS

Al-Maghrabi et al., "Immunoglobulin and T-cell receptor gene rearrangement in Castleman's disease: molecular genetic analysis," Histopathology 2006; 48(3):233-38.
(Continued)

*Primary Examiner* — Taylor V Oh
(74) *Attorney, Agent, or Firm* — Dechert LLP; Andrea L. C. Reid; Gang Wang

(57) ABSTRACT

The present invention provides compounds that modulate the interaction of TCR with Nck, compositions thereof, and methods of treatment using the same.

20 Claims, 1 Drawing Sheet

Related U.S. Application Data continuation of application No. 16/287,771, filed on Feb. 27, 2019, now Pat. No. 10,696,663.

(60) Provisional application No. 62/635,834, filed on Feb. 27, 2018.

(51) Int. Cl.

| | | |
|---|---|---|
| *A61P 37/02* | (2006.01) | |
| *C07D 405/14* | (2006.01) | |
| *C07D 413/14* | (2006.01) | |
| *C07D 405/06* | (2006.01) | |
| *A61P 35/00* | (2006.01) | |
| *C07D 405/12* | (2006.01) | |
| *A61P 37/00* | (2006.01) | |
| *A61P 17/00* | (2006.01) | |
| *A61P 11/06* | (2006.01) | |
| *C07D 413/12* | (2006.01) | |
| *A61P 29/00* | (2006.01) | |
| *C07D 311/58* | (2006.01) | |
| *A61P 3/10* | (2006.01) | |

(52) U.S. Cl.
CPC .............. *A61P 29/00* (2018.01); *A61P 35/00* (2018.01); *A61P 37/00* (2018.01); *A61P 37/02* (2018.01); *C07D 311/22* (2013.01); *C07D 311/58* (2013.01); *C07D 405/06* (2013.01); *C07D 405/12* (2013.01); *C07D 405/14* (2013.01); *C07D 413/12* (2013.01); *C07D 413/14* (2013.01)

(58) Field of Classification Search
CPC .. C07D 405/14; C07D 413/12; C07D 413/14; C07D 405/04; A61P 3/10; A61P 11/06; A61P 17/00; A61P 29/00; A61P 35/00; A61P 37/00; A61P 37/02; A61K 31/352; A61K 31/4025; A61K 31/453; A61K 31/496; A61K 31/5377
USPC ........................................................ 549/408
See application file for complete search history.

(56) References Cited

U.S. PATENT DOCUMENTS

| | | |
|---|---|---|
| 8,138,347 B2 | 3/2012 | Knight et al. |
| 8,338,439 B2 | 12/2012 | Singh et al. |
| 8,614,231 B2 | 12/2013 | Alarcon Sanchez et al. |
| 9,120,764 B2 | 9/2015 | Alarcon Sanchez et al. |
| 10,106,518 B2 | 10/2018 | Mateos et al. |
| 10,131,647 B2 | 11/2018 | Mateos et al. |
| 10,696,663 B2 | 6/2020 | Castro et al. |
| 2002/0068739 A1 | 6/2002 | Festal et al. |
| 2003/0105148 A1 | 6/2003 | Kaltenbach et al. |
| 2011/0207729 A1* | 8/2011 | Kinoyama ............ C07D 333/56 549/345 |
| 2012/0135041 A1 | 5/2012 | Alarcon Sanchez et al. |
| 2014/0005247 A1 | 1/2014 | Alarcon Sanchez et al. |
| 2016/0244423 A1 | 8/2016 | Mateos et al. |
| 2016/0251330 A1 | 9/2016 | Mateos et al. |
| 2019/0263792 A1 | 8/2019 | Castro et al. |
| 2020/0347042 A1 | 11/2020 | Castro et al. |

FOREIGN PATENT DOCUMENTS

| | | |
|---|---|---|
| EP | 2623503 A1 | 8/2013 |
| EP | 3059231 A1 | 8/2016 |
| EP | 3059232 A1 | 8/2016 |
| WO | WO-9933825 A1 | 7/1999 |
| WO | 2001034591 A2 | 5/2001 |
| WO | WO-2001042246 A2 | 6/2001 |
| WO | 0208217 A2 | 1/2002 |
| WO | 2002092076 A1 | 11/2002 |
| WO | WO-2002088112 A1 | 11/2002 |
| WO | WO-2003016270 A2 | 2/2003 |
| WO | 03062272 A1 | 7/2003 |
| WO | 2003096982 A2 | 11/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006078846 A1 | 7/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A2 | 6/2007 |
| WO | WO-2007084786 A1 | 7/2007 |
| WO | 2007115820 A1 | 10/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2009114512 A1 | 9/2009 |
| WO | 2010000900 A1 | 1/2010 |
| WO | 2010009069 A1 | 1/2010 |
| WO | WO-2010026269 A1 | 3/2010 |
| WO | WO-2010064707 A1 | 6/2010 |
| WO | WO-2011090760 A1 | 7/2011 |
| WO | WO-2012042078 A1 | 4/2012 |
| WO | WO-2013019926 A1 | 2/2013 |
| WO | WO-2014020159 A1 | 2/2014 |
| WO | 2015056085 A1 | 4/2015 |
| WO | 2015056086 A1 | 4/2015 |
| WO | WO-2016166239 A1 | 10/2016 |
| WO | 2019169001 A1 | 9/2019 |

OTHER PUBLICATIONS

Babbe et al., "Clonal expansions of CD8(+) T cells dominate the T cell infiltrate in active multiple sclerosis lesions as shown by micromanipulation and single cell polymerase chain reaction," J. Exp. Med. 2000; 192(3): 393-404.

Berge et al., "Pharmaceutical salts," J. Pharmaceutical Sciences 1977; 66(1):1-19.

Caforio et al., "Genetically determined myocarditis: clinical presentation and immunological characteristics," Curr. Opin. Cardiol. 2008; 23(3):219-26.

Cai et al., "New insights of T cells in the pathogenesis of psoriasis," Cell Mol. Immunol. 2012; 9(4):302-09.

Cetkovic-Cvrlje et al., "Therapeutic potential of Janus kinase 3 (JAK3) inhibitors," Curr. Pharm. Des. 2004; 10(15):1767-84.

Cetkovic-Cvrlje et al., "Targeting Janus kinase 3 in the treatment of leukemia and inflammatory diseases," Arch. Immunol. Ther. Exp. 2004; 52(2):69-82.

Choy, "T cells in psoriatic arthritis," Curr. Rheumatol. Rep. Exp. 2007; 9(6):437-41.

Cobrin et al., "Defects in mucosal immunity leading to Crohn's disease," Immunol. Rev. 2005; 206(1):277-95.

Cope et al., "The central role of T cells in rheumatoid arthritis," Clin. Exp. Rheumatol. 2007; 25(5):S4-11.

Crispin et al., "Expanded double negative T cells in patients with systemic lupus erythematosus produce IL-17 and infiltrate the kidneys," J. Immunol. 2008; 181(12):8761-66.

Dai et al., "The T cell regulator gene SH2D2A contributes to the genetic susceptibility of multiple sclerosis," Genes Immun. 2001; 2(5):263-8.

Direskeneli, "Innate and Adaptive Responses to Heat Shock Proteins in Behcet's Disease," Genetics Research International 2013; Article ID 249157, 6 Pages.

Fan et al., "Autoimmune pancreatitis," N. Am. J. Med. Sci. 2009; 1(2):148-51.

Finco et al., "Cytokine release assays: current practices and future directions," Cytokine 2014; 66(2):143-55.

Fuller et al., "All roads lead to actin: the intimate relationship between TCR signaling and the cytoskeleton," Immunol. Rev. 2003; 292:220-36.

(56) References Cited

OTHER PUBLICATIONS

Gonzalez-Rey et al., "Therapeutic effect of vasoactive intestinal peptide on experimental autoimmune encephalomyelitis: down-regulation of inflammatory and autoimmune responses," Am. J. Pathol. 2006; 168(4):1179-88.
Greco et al., "Cogan's syndrome: An autoimmune inner ear disease," Autoimmunity Rev. 2013; 12(3):396-400.
Guida et al., "Clonal CD8+ TCR-Vbeta expanded populations with effector memory phenotype in Churg Strauss syndrome," Clin. Immunol. 2008; 128(1):94-102.
Holgado et al., "Description of an advantageous optical label-free biosensing interferometric read-out method to measure biological species," Sensors 2014; 14(2):3675-89.
Holmdahl et al., "Collagen induced arthritis as an experimental model for rheumatoid arthritis. Immunogenetics, pathogenesis and autoimmunity," APMIS 1989; 97(7): 575-84.
Horai et al., "Microbiota-Dependent Activation of an Autoreactive T Cell Receptor Provokes Autoimmunity in an Immunologically Privileged Site," Immunity 2015; 43(2):343-53.
Issa et al., "Role of T cells in graft rejection and transplantation tolerance," Expert Rev. Clin. Immunol. 2010; 6(1):155-69.
International Search Report and Written Opinion issued by the European Patent Office as International Searching Authority for International Patent Application No. PCT/US2019/019856 dated Apr. 30, 2019 (16 pages).
Kappeler et al., "The role of activated cytotoxic T cells in inflammatory bowel disease," Histol Histopathol. 2000; 15(1):167-72.
Kitazawa et al., "Immunization with amyloid-beta attenuates inclusion body myositis-like myopathology and motor impairment in a transgenic mouse model," J. Neuroscience 2009; 29(19):6132-41.
Kudlacz et al., "The novel JAK-3 inhibitor CP-690550 is a potent immunosuppressive agent in various murine models," Am. J. Transplant. 2004; 4(1):51-7.
Laguna et al., "Antigen-Antibody Affinity for Dry Eye Biomarkers by Label Free Biosensing. Comparison with the ELISA Technique," Sensors 2015; 15(8):19819-29.
Laguna et al., "Optimization of Dengue Immunoassay by Label-Free Interferometric Optical Detection Method," Sensors 2014; 14(4):6695-6700.
Linterman et al., "Follicular helper T cells are required for systemic autoimmunity," J. Exp. Med. 2009; 206(3):561-76.
Manns et al., "Diagnosis and management of autoimmune hepatitis," Hepatology 2010; 51(6):2193-213.
Marks et al., "Innate immunity in inflammatory bowel disease: a disease hypothesis," J Pathol. 2008; 214(2):260-66.
Mazzarella, "Effector and suppressor T cells in celiac disease," World J. Gastroenterol. 2015; 21(24):7349-56.
Meriggioli et al., "Autoimmune myasthenia gravis: emerging clinical and biological heterogeneity," Lancet Neurology 2009; 8(5):475-90.
Morgan et al., "CD4+CD28– T cell expansion in granulomatosis with polyangiitis (Wegener's) is driven by latent cytomegalovirus infection and is associated with an increased risk of infection and mortality," Arthritis & Rheumatism 2011; 63(7):2127-37.
Nograles et al., "IL-22-producing "T22" T cells account for upregulated IL-22 in atopic dermatitis despite reduced IL-17-producing TH17 T cells," J. Allergy Clin. Immunol. 2009; 123(6):1244-52.
Notturno et al., "Susceptibility to chronic inflammatory demyelinating polyradiculoneuropathy is associated to polymorphic GA repeat in the SH2D2A gene," J. Neuroimmunol. 2008; 197(2):124-7.
Onouchi et al., "ITPKC functional polymorphism associated with Kawasaki disease susceptibility and formation of coronary artery aneurysms," Nature Genetics 2008; 40(1):35-42.
O'Sea et al., "A new modality for immunosuppression: targeting the JAK/STAT pathway," Nat. Rev. Drug Doscpv. 2004; 3(7):555-64.
Petukhova et al., "Genome-wide association study in alopecia areata implicates both innate and adaptive immunity," Nature 2010; 466(7302):113-17.
Raveche et al., "Evidence of Borrelia autoimmunity-induced component of Lyme carditis and arthritis," J. Clin. Microbiol. 2005; 43(2):850-56.
Robinson, "The role of the T cell in asthma," J. Allergy Clin. Immunol. 2010; 126(6):1081-91.
Roche et al., "Sensitization to epithelial antigens in chronic mucosal inflammatory disease. Characterization of human intestinal mucosa-derived mononuclear cells reactive with purified epithelial cell-associated components in vitro," J. Clin. Invest. 1985; 75(2):522-530.
Roep, "The role of T-cells in the pathogenesis of Type 1 diabetes: From cause to cure," Diabetologia 2003; 46(3):305-21.
Sasaki et al., "Direct Preparation of 3-lodochromenes from 3-Aryl- and 3-Alkyl-2-propyn-1-ols with Diaryliodonium Salts and NIS," Org. Lett. 2016; 18(5):944-947.
Shlomchik, "Graft-versus-host disease," Nature Rev. Immunology 2007; 7:340-52.
Silva et al., "Diagnosis and classification of autoimmune orchitis," Autoimmun Rev. 2014; 13(4-5):431-34.
Singh et al., "Lyme borreliosis: from infection to autoimmunity," Paediatric Rheumatology 2004; 10(7):598-614.
Smith, "Update on Ankylosing Spondylitis: Current Concepts in Pathogenesis," Curr Allergy Asthma Rep. 2015; 15(1):489.
Sneller et al., "Autoimmune lymphoproliferative syndrome," Curr. Opin. Rheumatology 2003; 15(4):417-21.
Teachey et al., "Unmasking Evans syndrome: T-cell phenotype and apoptotic response reveal autoimmune lymphoproliferative syndrome (ALPS)," Blood 2004; 105(6):2443-48.
Tse et al., "Suppression of allogeneic T-cell proliferation by human marrow stromal cells: implications in transplantation," Transplantation 2003; 75(3):389-97.
Van den Wijngaard et al., "Local immune response in skin of generalized vitiligo patients. Destruction of melanocytes is associated with the prominent presence of CLA+ T cells at the perilesional site," Lab Invest. 2000; 80(8):1299-309.
Zenewicz et al., "CD4 T-cell differentiation and inflammatory bowel disease," Trends Mol. Med. 2009; 15(5):199-207.
Alarcon, Balbino. Initiation of TCR signaling: regulation within CD3 dimers, Immunological Reviews 2003 vol. 191, pp. 38-46. Copyright Blackwell Munksgaard, Denmark.
American Diabetes Association, "complications", http://www.diabetes.org/living-with-diabetes/complications/, accessed Dec. 27, 2017 (Year: 2017).
Asquith et al., Eur. J. Immunol., 2009, vol. 39, No. 8, pp. 2040-2044 (Year: 2009).
Borie, Dominic. Combined Use of the JAK3 Inhibitor CP-690,550 with Mycophenolate Mofetil to Prevent Kidney Allograft Rejection in Nonhuman Primates, Transplantation, vol. 80, No. 12, Dec. 27, 2005, p. 1756, Copyright Lippincott Williams & Wilkins.
Das et al. (Bioorg. Med. Chem. Lett. 16 (2006) 3706-3712).
Database Registry, RN 340014-88-2, Retrieved from STN international [online]; retrieved on Jul. 8, 2013, Japanese Office Action of Japanese Application 2011-515490 dated Jul. 16, 2013.
Francesco Leonetti et al; "Design, Synthesis, and 3D QSAR of Novel Potent and Selective Aromatase Inhibitors", Journal of Medicinal Chemistry, vol. 47, No. 27, Dec. 1, 2004 (Dec. 1, 2004). pp. 6792-6803, XP055096789, ISSN: 0022-2623, DOI: 10.1021/jm049535j *tables 3,4; compound 32*.
Gil, Diana. Recruitment of Nck by CD3e Reveals a Ligand-Induced Conformational Change Essential for T Cell Receptor Signaling and Synapse Formation, Cell, vol. 109, pp. 901-912, Jun. 28, 2002, Copyright 2002 by Cell Press.
Glennon, Richard A. Serotonin Receptor Affinity of Cathinone and Related Analogues, J. Med. Chem 1982, 25, pp. 393-397, Copyright 1982 American Chemical Society =.
Higuchi, Takao. Prevention of Acute Lung Allograft Rejection in Rat by the Janus Kinase 3 Inhibitor, Tyrphostin AG490, The Second Department of Surgery and Department of Biochemistry, Fukuoka University School of Medicine, Fukuoka, Japan, Nov. 13, 2004, Copyright 2005 by the International Society for Heart and Lung Transplantation.
International Search Report dated Jan. 12, 2015 for International Application No. PCT/IB2014/002171, filed Oct. 20, 2014.

(56) References Cited

OTHER PUBLICATIONS

International Search Report issued by the Spanish Patent and Trademark Office as Searching Authority for International Patent Application No. PCT/ES2013/31543, dated Jan. 20, 2015 (4 pages).
Kannan et al., Pathophysiology, 2005, vol. 12., No. 3, pp. 167-181 (Year: 2005).
Kaur et al. (European Journal of Pharmaceutical Sciences 47 (2012) 574-588).
Kremer, Joel M. A Randomized, Double-Blind, Placebo-Controlled Trial of 3 Dose Levels of CP-690,550 Versus Placebo in the Treatment of Active Rheumatoid Arthritis, American College of Rheumatology, 2006 Annual Scientific Meeting, Presentation No. L40.
Kubinyi (3D QSAR in Drug Design: Ligand-Protein Interactions and Molecular Similarity, vol. 2-3, Springer, 1998, 800 pages). pp. 243-44 provided.
Lin, Joseph. T Cell Receptor Signalling, Journal of Cell Science, 114 (2), pp. 243-244.
Malaviya, Ravi. Targeting Janus Kinase 3 in Mast Cells Prevents Immediate Hypersensitivity Reactions and Anaphylaxis, The Journal of Biological Chemistry, vol. 274, No. 38, Sep. 17, 1999, pp. 27028-27038, Copyright 1999 by The American Society for Biochemistry and Molecular Biology, Inc.
Matsumoto, Masahiro. IgE Hyperproduction Through Enhanced Tyrosine Phosphorylation of Janus Kinase 3 in NC/Nga Mice, a Model for Human Atopic Dermatitis, The Journal of Immunology 1999; 162, pp. 1056-1063, Copyright 1999 by The American Association of Immunologists.
Mayo Clinic, "Diabetes", <https://www.mayoclinic.org/diseases-conditions/diabetes/symptoms-causes/syc-20371444>, accessed Dec. 27, 2017 (Year: 2017).
Milici, Anthony J. Cartilage Preservation by Inhibition of Janus Kinase 3 (JAK3) in a Murine Collagen-Induced-Arthritis (CIA) Model and Rat Adjuvant-Arthritis (AA) Model, American College of Rheumatology, 2006 Annual Scientific Meeting, Presentation No. 789.
Minguet, S., Swamy, M., Alarcon, B., Luescher, I.F. and Schamel, W.W. (2007) Immunity., 26, 43-54.
Moudgil et al., Curr. Rheumatol. Rep., 2011, vol. 13, No. 5, pp. 456-463 (Year 2011).
Muller-Ladner, Ulf. Activation of the IL-4 STAT Pathway in Rheumatoid Synovium, The Journal of Immunology 2000, 164, pp. 3894-3901, <http://www.jimmunology.org>.
Narla et al., "Inhibition of Human Glioblastoma Cell Adhesion and Invasion by 4-(4'-Hydroxylphenyl)-amino-6,7-limethoxyquinazoline (WHI-P131) and 4-(3'-Bromo-4'-hydroxylphenyl)-amino-6,7-dimethoxyquinazoline (WHI-P154)," Clinical Cancer Research, vol. 4, Oct. 1998 (pp. 2463-2471).
Paniagua, Ricardo. Effects of JAK3 Inhibition with CP-690,550 on Immune Cell Populations and Their Functions in Nonhuman Primate Recipients of Kidney Allografts, Immunobiology and Genomics, Transplantation, vol. 80, No. 9, Nov. 15, 2005, p. 1283, Copyright Lippincott Williams & Wilkins.
PCT International Search Report from PCT/ES2009/070239 dated Oct. 5, 2009.
PCT International Search Report from PCT/ES2011/070506 dated Dec. 16, 2011.
PCT International Search Report from PCT/IB2014/002171 dated Jan. 12, 2015.
PCT International Search Report from PCT/IB2014/002177 dated Jan. 13, 2015.
Richter, K. et al., "Small molecule AX-024 reduces T cell proliferation independently of CD3/Nck1 interaction, which is governed by a domain swap in the Nck1-SH3.1 domain", Journal of Biological Chemistry, 2020, vol. 295, No. 23, pp. 7849-7864.
Risueno, R.M., Gil, D., Fernandez, E., Sanchez-Madrid, F. and Alarcon, B. (2005) Blood, 106, 601-608.
Risueno, R.M., van Santen, H.M. and Alarcon, B. (2006) Proc NatlAcad Sci U S A., 103, 9625-9630.
Rousvoal, Geraldine. Janus Kinase 3 Inhibition with CP-690,550 Prevents Allograft Vasculopathy, Journal compilation Copyright 2006 European Society for Organ Transplantation, pp. 1014-1021.
Roy, Edwige. Nck Adaptors are Positive Regulators of the Size and Sensitivity of the T-Cell Repertoire, PNAS, Aug. 31, 2010, vol. 107, No. 35, pp. 15529-15534.
Saemann, Marcus. Janus Kinase-3 (JAK3) Inhibition: A Novel Immunosuppressive Option for Allogeneic Transplantation, Transpl Int. (2004) 17: pp. 481-489, Sep. 11, 2004, Copyright Springer-Verlag 2004.
Silva et al., "Immunotherapy for De Novo Renal Transplantation," Drugs, vol. 66, No. 13, No Month Listed 2006 (pp. 1665-1684).
Spanish Search Report dated Jan. 20, 2015 for International Application No. 201331542, filed Oct. 18, 2013.
Sudbeck, Elise A. Structure-based Design of Specific Inhibitors of Janus Kinase 3 as Apoptosis-inducing Antileukemic Agents, Clinical Cancer Research, vol. 5, pp. 1569-1582, Jun. 1999, Copyright 1999 American Association for Cancer Research.
Tibbles, Heather E. Role of a JAK3-dependent Biochemical Signaling Pathway in Platelet Activation and Aggreation, The Journal of Biological Chemistry, vol. 276, No. 21, pp. 17815-17822, May 25, 2001, Copyright 2001 by The American Society for Biochemistry and Molecular Biology, Inc.
Trieu, Vuong. A Specific Inhibitor of Janus Kinase-3 Increases Survival in a Transgenic Mouse Model of Amyotrophic Lateral Sclerosis, Biochemical and Biophysical Research Communications 267, pp. 22-25, Copyright 2000 by Academic Press.
Vogel's Textbook of Practical Organic Chemistry, 5th ed. (1989), 1514 pages). pp. 989-999 provided.
Walker, J.G. Changes in Synovial Tissue JAK-STAT Expression in Rheumatoid Arthritis in Response to Successful DMARD Treatment, Ann Rheum Dis. 2006, 65, pp. 1558-1564.
Wermuth, The Practice of Medicinal Chemsitry, 2d ed. (2003), 768 pages. Chs. 9-10 provided.
Borroto et al., "First-in-class inhibitor of the T cell receptor for the treatment of autoimmune diseases." Sci Transl Med. 2016;8(370):370ra184.

* cited by examiner

| | Stock Conc (mM) | 20 mM | | | | | | | | | | | |
|---|---|---|---|---|---|---|---|---|---|---|---|---|---|
| 100% DMSO | | | 2 µL (20 mM) + 98.25 µL (100% DMSO) | → | | | | | | | | | |
| | | | | | 3.125 fold dilution (16 µL Compound + 24 µL DMSO) | | | | | | | | |
| 100% DMSO | Stock dil (uM) | | | 399 | 133.0000 | 44.3333 | 14.7778 | 4.9259 | 1.6420 | 0.5473 | 0.1824 | 0.0608 | 0.0203 | 0.0068 |
| | 1 µL Compound + 132 µL RPMI Medium | | | → | → | → | → | → | → | → | → | → | → | → |
| 0.75% DMSO | Intermediate dil | | | 3.0000 | 1.0000 | 0.3333 | 0.1111 | 0.0370 | 0.0123 | 0.0041 | 0.0014 | 0.0005 | 0.0002 | 0.0001 |
| | 4 µL Compound in 12 µL total reaction volume | | | → | → | → | → | → | → | → | → | → | → | → |
| 0.25% DMSO | Final Conc (uM) | | | 1.0000000 | 0.333333 | 0.111111 | 0.037037 | 0.012345 | 0.004115 | 0.001372 | 0.000457 | 0.000152 | 0.000051 | 0.0000017 |

CHROMENE DERIVATIVES AS INHIBITORS OF TCR-NCK INTERACTION

TECHNICAL FIELD OF THE INVENTION

The present invention relates to a group of compounds containing a chromene core and having the ability to inhibit lymphocyte proliferation by blocking the interaction of TCR with Nck. Therefore, such compounds are useful for treating diseases, disorders, or conditions where such interaction triggers a complication such as transplant rejection reactions, immune or autoimmune disease or proliferation.

BACKGROUND OF THE INVENTION

Autoimmune and inflammatory diseases such as asthma, multiple sclerosis (MS), allergies, rheumatoid arthritis (RA), Crohn's disease, or psoriasis are a diverse group of disease in which the adaptive immune system, particularly via T-lymphocytes, attack of the body's own antigens. It is commonly accepted that T-cells are at the center of all immunological mechanisms. T-cells can recognize both foreign and self-antigens, and activate the immune response against them. T-cells recognize antigens via the T-cell antigen receptor (TCR), which is responsible for the transmission of signals to the cytoplasm. Indeed, the fact that the haplotype of the major histocompatibility complex (MHC) is the most important genetic risk factor to the human autoimmune disease places T-cells in the center of all immunopathological events.

The T-cell recognizes the antigen peptide associated with MHC (pMHC) via the TCR and is able to translate the small differences in the chemical composition of the pMHC into different quantitative and qualitative results. While a variety of control mechanisms to prevent activation of T-cells bearing TCRs with significant affinity for MHC loaded with self-peptides exists, including suppression of potentially auto-reactive T-cells during maturation in the thymus, these mechanisms are somewhat insufficient in patients what develop autoimmune diseases and auto-reactive T-cells are activated and expand, overcoming homeostatic controls.

Upon stimulation, the TCR is activated and undergoes a conformational change that results in the recruitment of different proteins forming the "TCR signalosome" responsible for signal transduction and cell activation. This complex includes the cytosolic protein non-catalytic region of tyrosine kinase protein (Nck) that binds to the proline-rich sequence (PRS) motif present in the CD3ε subunit of the TCR. As a result, the TCR conformational change stabilizes and the activation signal is efficiently transmitted.

Current therapies for immune diseases appear as immunosuppressive strategies rather than tolerogenic/immunomodulatory approaches. Azathioprine, methotrexate, mycophenolate, and cladribine are cytostatic. Other therapies force the depletion of T-cells (Alemtuzumab, anti-CD25) or their retention in the lymph nodes (Fingolimod). Alternatively, indirect modulation of the immune system is also being used as a powerful strategy (BG-12). Therefore, despite the central role of TCR signal for activating T-cells in autoimmune diseases, recent efforts to modulate activation of T-cells are focused on modulating co-stimulatory signals, cytokine receptors, etc., with the consequent lack of specificity and a large number of associated side effects.

In order to develop a specific immunomodulatory therapy, many efforts have been focused on characterizing the role of Nck in T-cell activation by means of many different research groups. Nck has been attributed an important role in the function of mature T-cells through studies in knock-out mice lacking Nck1 in all tissues and lacking Nck2 conditionally only in T-cells. In these models, the number of peripheral T-cells expressing a TCR with low avidity for self-antigens fell sharply, and a general deterioration in the activation of T-cells by stimulation with weak antigens was observed. Moreover, the importance of Nck was also addressed by generating bone marrow chimeras showing that the PRS motif (Nck binding site in the TCR) is important for the activation of mature T-cells by weak agonists but not strong ones. Similarly, mutation of the PRS motif altered the ability of mice to activate an adaptive immune response in vivo. Furthermore, an inhibitor peptide with high affinity for the SH3.1 domain of Nck alters the assembly of the TCR signalosome, suggesting that the recruitment of Nck is a critical early step in TCR signaling, which represents a target for the modulation of the immune system.

The document WO 2010/064707 describes a series of compounds derived from 2H-chomene for the prevention or treatment of a disease induced by an undesired lymphocyte infiltration mediated by sphingosine-1-phosphate (S1P1).

The document WO 2012/042078 also describes chrome derivative with inhibitory capacity of the TCR-Nck interaction in T-cells and their use for the treatment of autoimmune diseases, inflammatory diseases, or transplant rejection.

It would therefore be desirable to provide novel compounds which are capable of inhibiting TCR-Nck interactions in T lymphocytes, and that are good drug candidates. The compounds should exhibit good activity on in vivo pharmacological trial, good oral absorption when administered orally, as well as being metabolically stable and having a favorable pharmacokinetic profile. Moreover, the compounds should not be toxic and present minimal side effects.

SUMMARY OF THE INVENTION

It has now been found that compounds of this invention, and pharmaceutically acceptable compositions thereof, are effective at modulators of the interaction of TRC with Nck. Such compounds have a general Formula I:

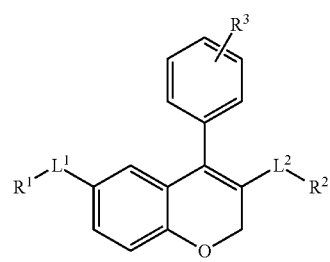

I or a pharmaceutically acceptable salt thereof, wherein each variable is as defined and described herein.

Compounds of the present invention, and pharmaceutically acceptable compositions thereof, are useful for treating a variety of diseases, disorders, or conditions, associated with T-cell activation. Such diseases, disorders, or conditions include those described herein.

BRIEF DESCRIPTION OF DRAWINGS

FIG. 1 depicts an exemplary compound dilution scheme.

DETAILED DESCRIPTION OF CERTAIN EMBODIMENTS

General Description of Certain Embodiments of the Invention

In certain embodiments, the present invention provides a compound of Formula I:

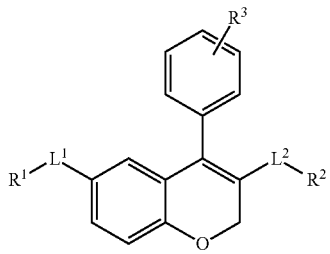

I or a pharmaceutically acceptable salt thereof, wherein:
$R^1$ is R, halogen, —CN, —OR, or —N(R)$_2$;
$R^2$ is R, halogen, —C(O)N(R)$_2$, or —N(R)$_2$;
$R^3$ is hydrogen or an electron withdrawing group;
each R is independently hydrogen or an optionally substituted group selected from C$_{1-6}$ aliphatic, a 3-8 member saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur; or
two R groups on the same nitrogen are taken together with their intervening atoms to form an optionally substituted 5-6 membered heterocyclic ring having 0-1 heteroatoms in addition to the nitrogen attached thereto wherein such heteroatom is oxygen, nitrogen, or sulfur;
$L^1$ is a covalent bond or a C$_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —C(F)$_2$—, —N(R)—, —C(O)N(R)—, —RNC(O)—, —OC(O)N(R)—, —N(R)C(O)N(R)—, or -Cy-;
$L^2$ is a covalent bond or a C$_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —CH(R)—, —C(F)$_2$—, —N(R)—, —C(O)N(R)—, —RNC(O)—, —OC(O)N(R)—, or —N(R)C(O)N(R)—; and
Cy is a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur.

In some embodiments, the present invention provides a compound of Formula I wherein said compound is other than:

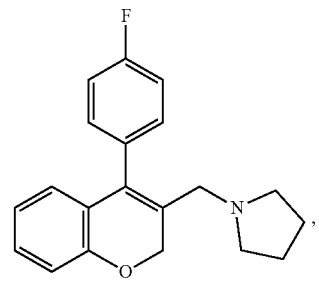

1

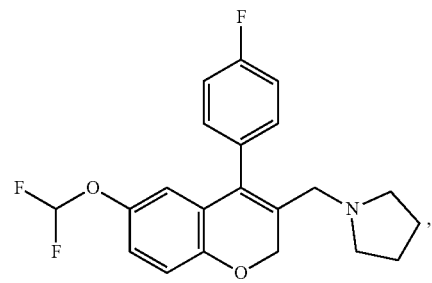

2

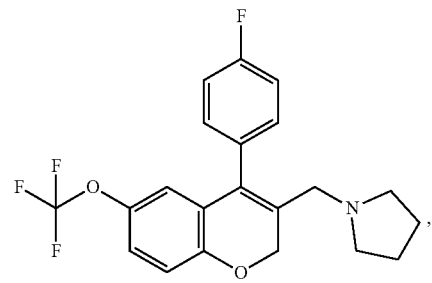

3

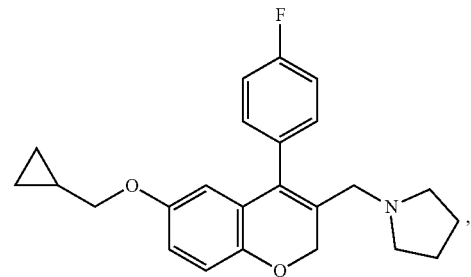

4

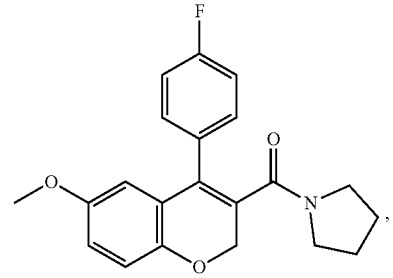

5

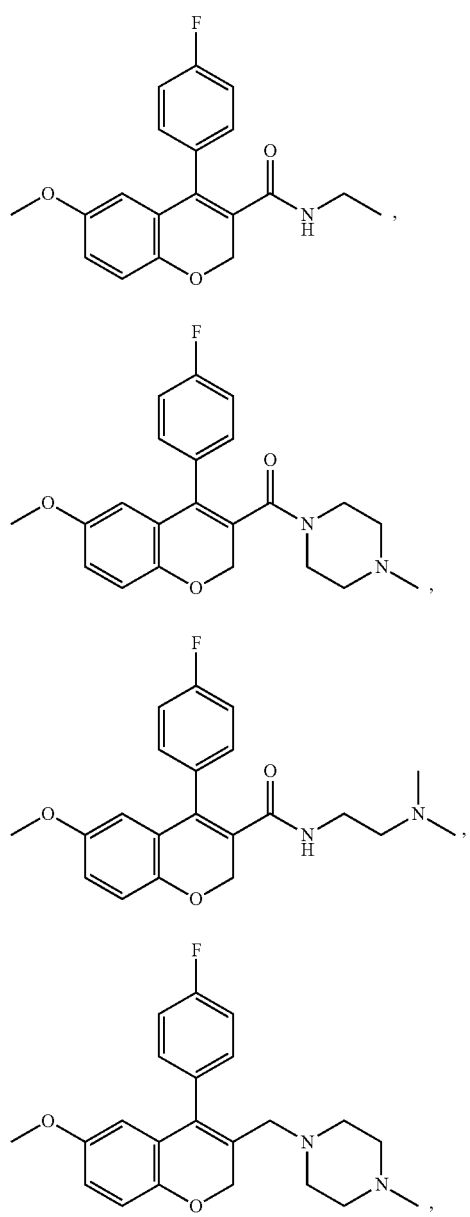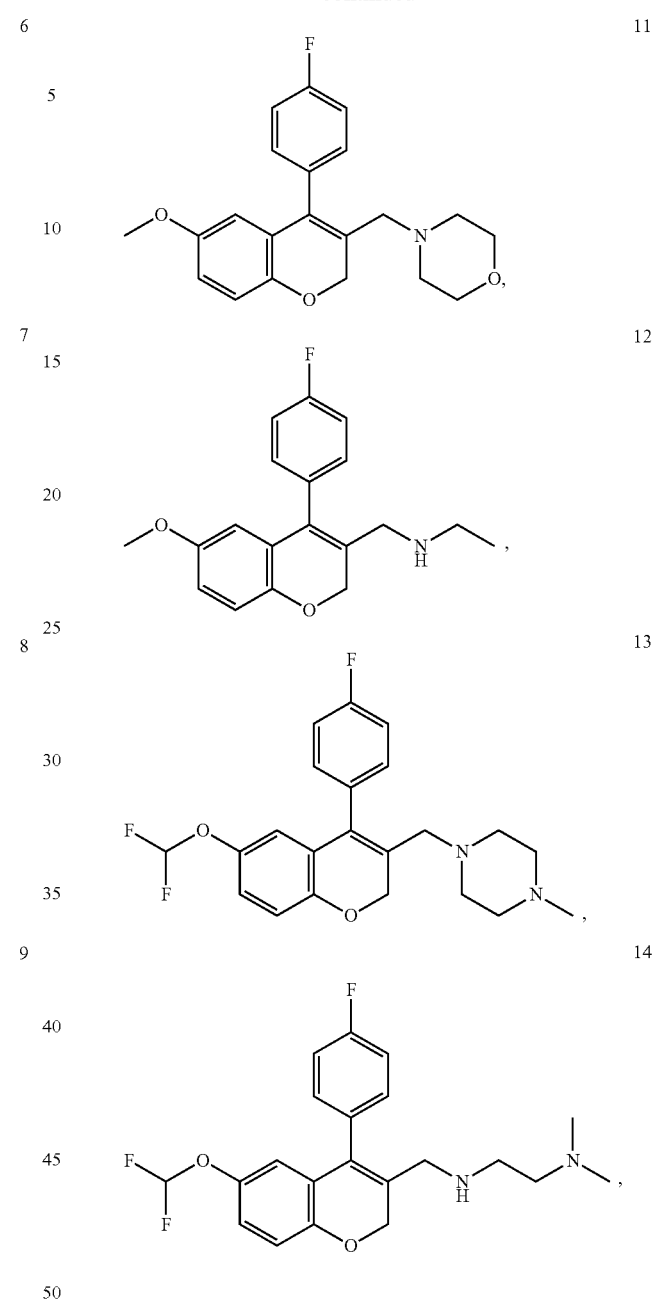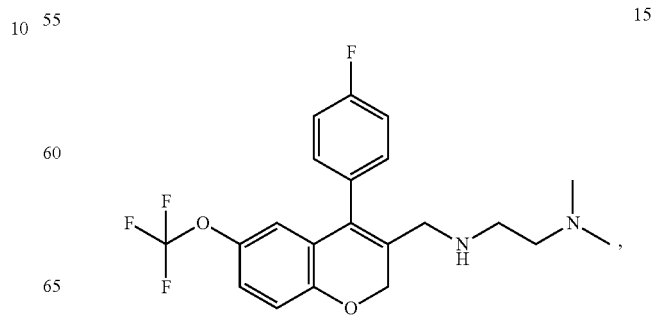

16
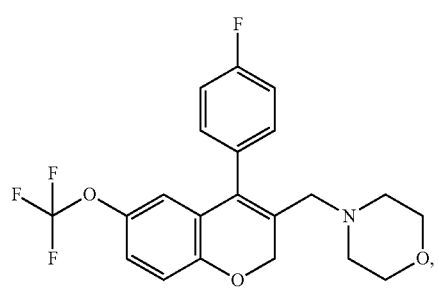
17
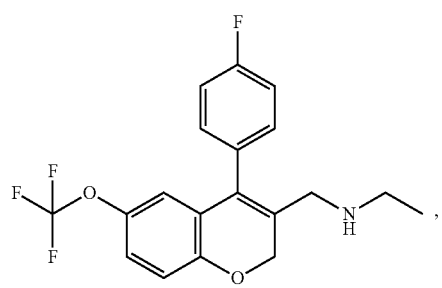
18
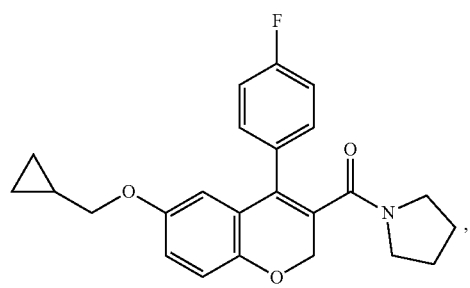
19
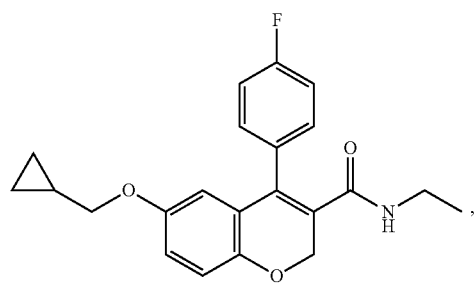
20
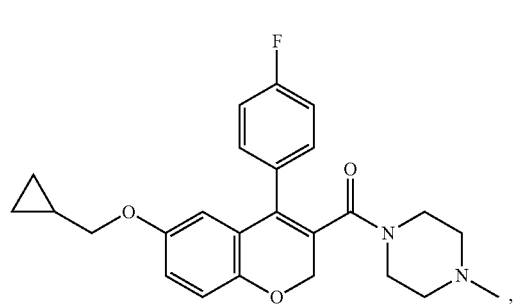
21
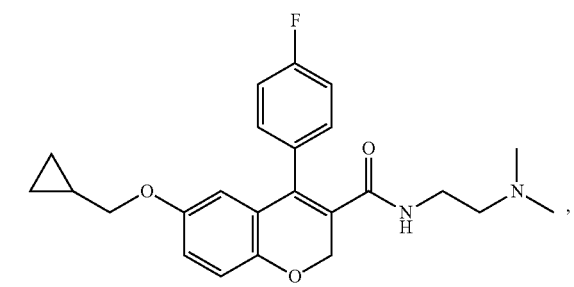
22
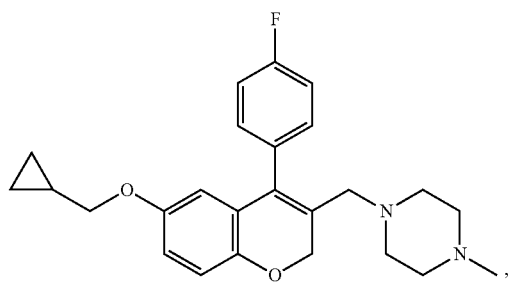
23
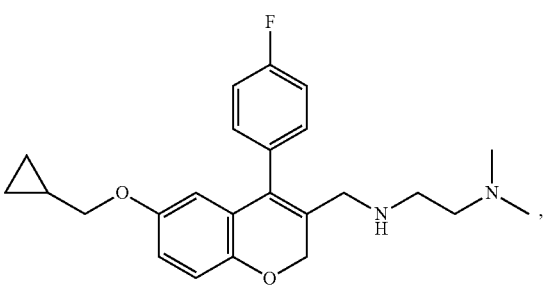
24
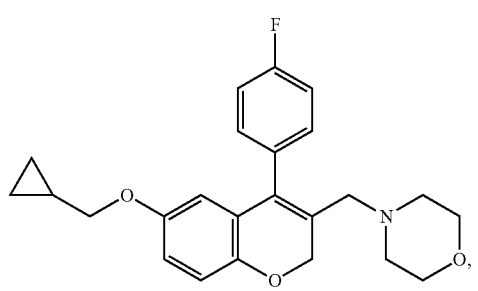
25
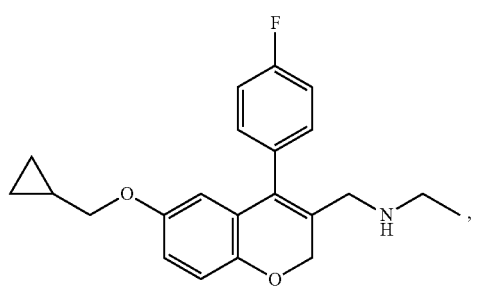

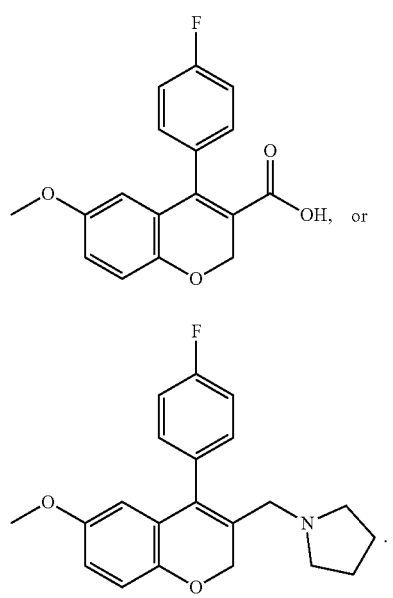
26
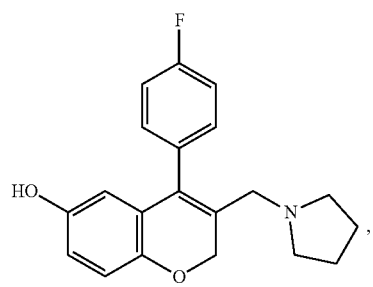
27
In some embodiments, the present invention provides a compound of Formula I wherein said compound is other than:
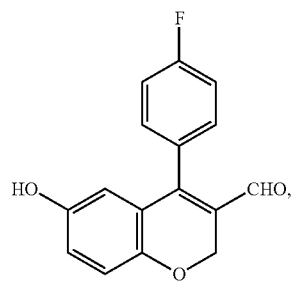
28
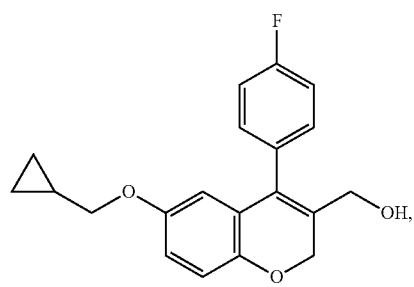
29
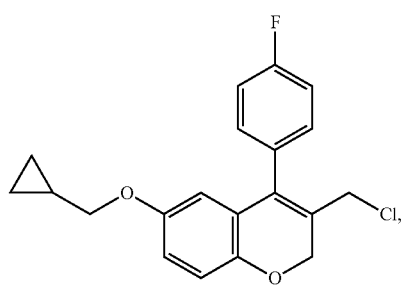
31
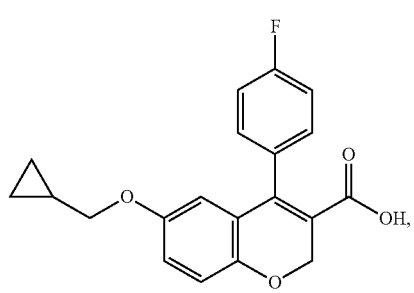
32
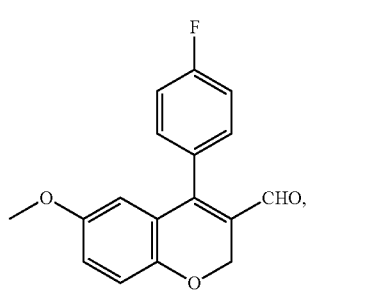
33
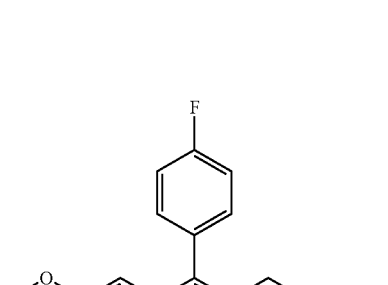
34
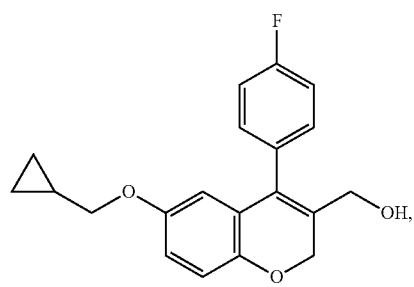
30
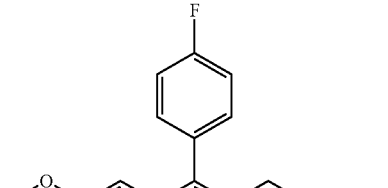
35

36 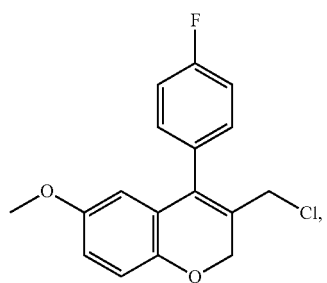
37 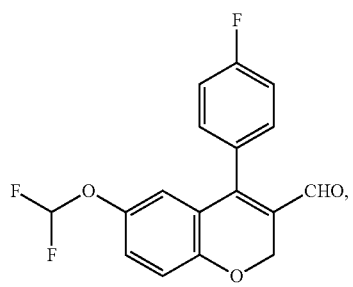
38 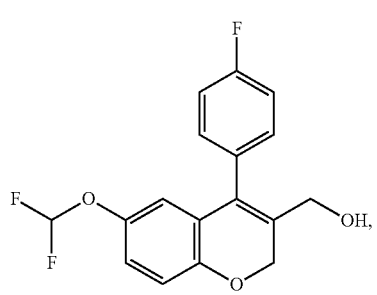
39 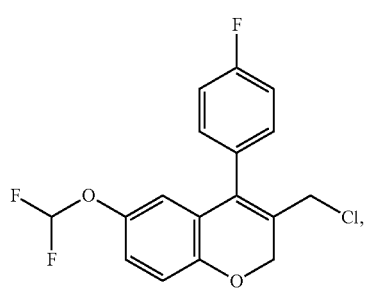
40 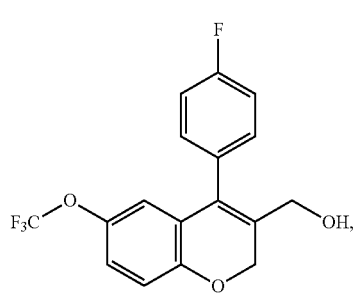
41 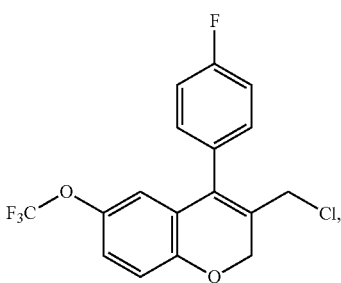
42 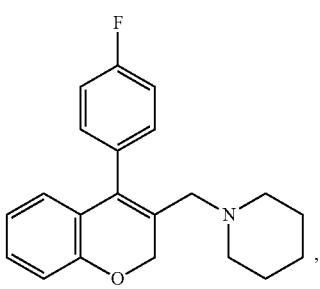
43 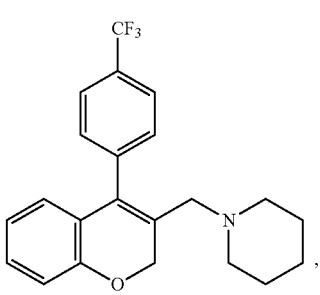
44 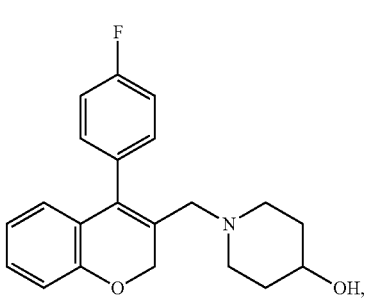
45 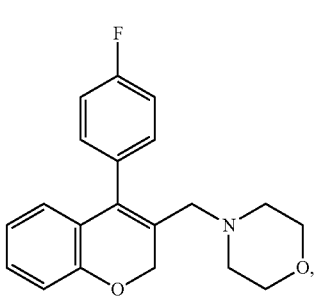

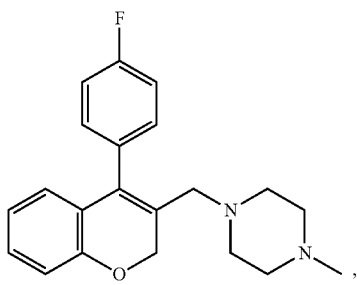

46

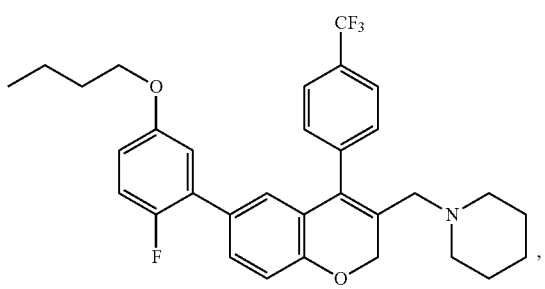

47

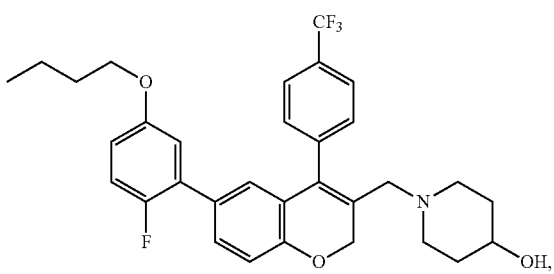

48

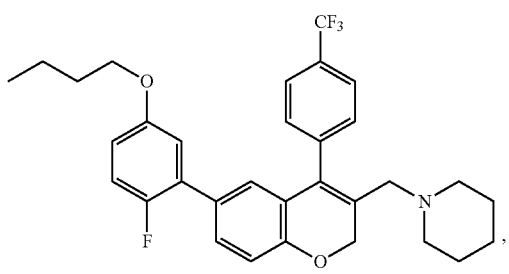

50

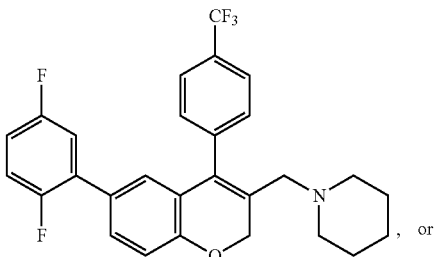

51

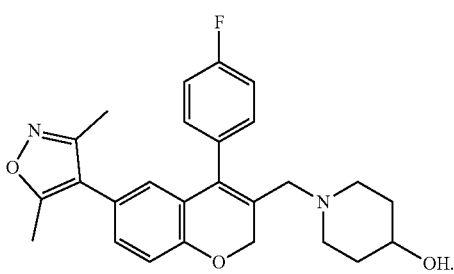

, or

52

Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, *Handbook of Chemistry and Physics*, 75th Ed. Additionally, general principles of organic chemistry are described in *Organic Chemistry*, Thomas Sorrell, University Science Books, Sausalito: 1999, and *March's Advanced Organic Chemistry*, 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e. unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well-known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

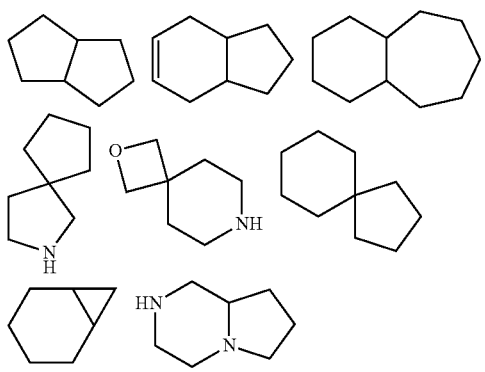

Exemplary bridged bicyclics include:

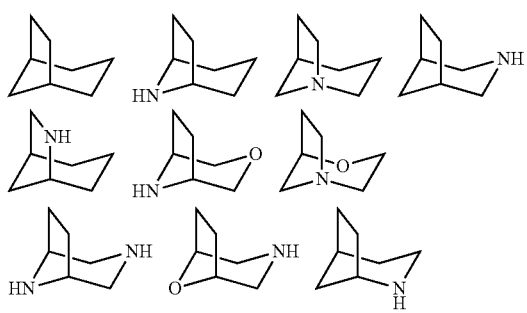

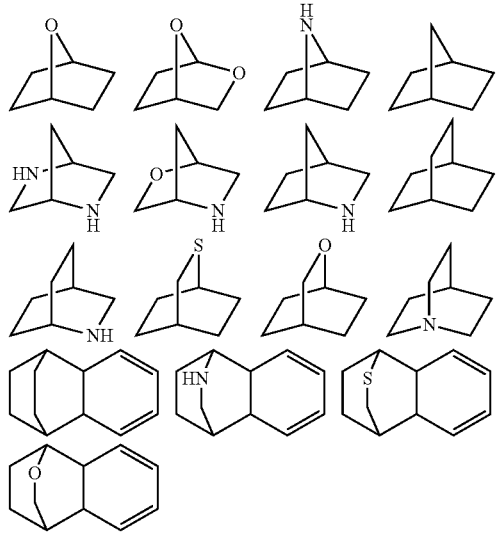

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-4}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

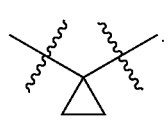 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-40}$S(O)$_2$R°; —S(O)$_2$NR°$_2$; —S(O)(NR°)R°; —S(O)$_2$N═C(NR°$_2$)$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^{\bullet}$; -(haloR$^{\bullet}$); —$(CH_2)_{0-2}OH$; —$(CH_2)_{0-2}OR^{\bullet}$; —$(CH_2)_{0-2}CH(OR^{\bullet})_2$; —O(haloR$^{\bullet}$); —CN; —$N_3$; —$(CH_2)_{0-2}C(O)R^{\bullet}$; —$(CH_2)_{0-2}C(O)OH$; —$(CH_2)_{0-2}C(O)OR^{\bullet}$; —$(CH_2)_{0-2}SR^{\bullet}$; —$(CH_2)_{0-2}SH$; —$(CH_2)_{0-2}NH_2$; —$(CH_2)_{0-2}NHR^{\bullet}$; —$(CH_2)_{0-2}NR^{\bullet}_2$; —$NO_2$, —$SiR°_3$; —$OSiR°_3$; —C(O)SR$^{\bullet}$; —$(C_{1-4}$ straight or branched alkylene)C(O)OR$^{\bullet}$; or —SSR$^{\bullet}$ wherein each R$^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O; =S; =NNR*$_2$; =NNHC(O)R*; =NNHC(O)OR*; =NNHS(O)$_2$R*; =NR*; =NOR*; —O(C(R*$_2$))$_{2-3}$O—; or —S(C(R*$_2$))$_{2-3}$S—; wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^{\bullet}$; -(haloR$^{\bullet}$); —OH, —OR$^{\bullet}$; —O(haloR$^{\bullet}$); —CN; —C(O)OH; —C(O)OR$^{\bullet}$; —$NH_2$; —NHR$^{\bullet}$; —NR$^{\bullet}_2$; or —$NO_2$; wherein each R$^{\bullet}$ is unsubstituted or where preceded by "halo" is substituted only with one or more halogens, and is independently $C_{1-4}$ aliphatic, —$CH_2Ph$; —$O(CH_2)_{0-1}Ph$; or a 5-6-membered saturated; partially unsaturated; or aryl ring having 0-4 heteroatoms independently selected from nitrogen, oxygen, or sulfur.

Suitable substituents on a substitutable nitrogen of an "optionally substituted" group include —R$^{\dagger}$; —NR$^{\dagger}_2$; —C(O)R$^{\dagger}$; —C(O)OR$^{\dagger}$; —C(O)C(O)R$^{\dagger}$; —C(O)CH$_2$C(O)R$^{\dagger}$; —S(O)$_2$R$^{\dagger}$; —S(O)$_2$NR$^{\dagger}_2$; —C(S)NR$^{\dagger}_2$; —C(NH)NR$^{\dagger}_2$; or —N(R$^{\dagger}$)S(O)$_2$R$^{\dagger}$; wherein each R$^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, —R$^{\bullet}$; -(haloR$^{\bullet}$); —OH; —OR$^{\bullet}$; —O(haloR$^{\bullet}$); —CN; —C(O)OH; —C(O)OR$^{\bullet}$; —$NH_2$; —NHR$^{\bullet}$; —NR$^{\bullet}_2$; or —$NO_2$; wherein each R$^{\bullet}$ is unsubstituted or where preceded by "halo" is substituted only with one or more halogens, and is independently $C_{1-4}$ aliphatic, —$CH_2Ph$; —$O(CH_2)_{0-1}Ph$; or a 5-6-membered saturated; partially unsaturated; or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well-known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

As used herein, the term "inhibitor" is defined as a compound that binds to and/or inhibits TCR-Nck with measurable affinity. In certain embodiments, an inhibitor has an $IC_{50}$ and/or binding constant of less than about 100 µM, less than about 50 µM, less than about 1 µM, less than about 500 nM, less than about 100 nM, less than about 10 nM, or less than about 1 nM.

The terms "measurable affinity" and "measurably inhibit," as used herein, means a measurable change in TCR activity between a sample comprising a compound of the present invention, or composition thereof, TCR, and Nck, and an equivalent sample comprising TCR and Nck in the absence of said compound, or composition thereof.

The term "modulate" and "modulating," as used herein, means to influence or alter the activity. Modulation comprises stabilization, destabilization, enhancement, and suppression.

The term "protein-protein interaction," (PPI) as used herein, means the high specificity physical contact between two or more protein molecules. A person having ordinary skill in the art would appreciate that such interaction include short-term, transient interaction, as well as stable interactions.

DESCRIPTION OF EXEMPLARY EMBODIMENTS

In certain embodiments, the present invention provides a compound of Formula I:

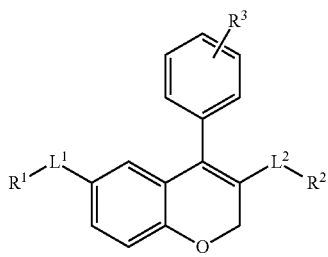

I or a pharmaceutically acceptable salt thereof, wherein:
  $R^1$ is R, halogen, —CN, —OR, or —N(R)$_2$;
  $R^2$ is R, halogen, —C(O)N(R)$_2$, or —N(R)$_2$;
  $R^3$ is hydrogen or an electron withdrawing group;
  each R is independently hydrogen or an optionally substituted group selected from $C_{1-6}$ aliphatic, a 3-8 member saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur; or
    two R groups on the same nitrogen are taken together with their intervening atoms to form an optionally substituted 5-6 membered heterocyclic ring having 0-1 heteroatoms in addition to the nitrogen attached thereto wherein such heteroatom is oxygen, nitrogen, or sulfur;

$L^1$ is a covalent bond or a $C_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —C(F)$_2$—, —N(R)—, —C(O)N(R)—, —RNC(O)—, —OC(O)N(R)—, —N(R)C(O)N(R)—, or -Cy-;

$L^2$ is a covalent bond or a $C_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —CH(R)—, —C(F)$_2$—, —N(R)—, —C(O)N(R)—, —RNC(O)—, —OC(O)N(R)—, or —N(R)C(O)N(R)—; and each Cy is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur.

As defined above and described herein, $R^1$ is R, halogen, —CN, —OR, or —N(R)$_2$.

In some embodiments, $R^1$ is hydrogen.

In some embodiments, $R^1$ is halogen or —CN.

In some embodiments, $R^1$ is R, —OR, or —N(R)$_2$.

In some embodiments, $R^1$ is —CH$_3$, —CD$_3$, —CH(CH$_3$)$_2$,

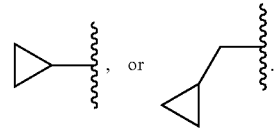

In some embodiments, $R^1$ is

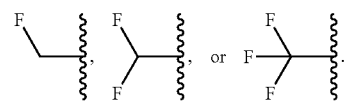

In some embodiments, $R^1$ is R. In some embodiments, R is optionally substituted $C_{1-6}$ aliphatic. In some embodiments, R is optionally substituted $C_{1-6}$ alkyl. In some embodiments, R is $C_{1-6}$ alkyl optionally substituted by halogen or —COOH. In some embodiments, R is $C_{1-6}$ alkyl substituted 1-6 times by halogen. In some embodiments, R is $C_{1-6}$ alkyl substituted 1 time by —COOH.

In some embodiments, $R^1$ is

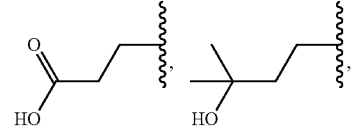

In some embodiments, R¹ is

[structures: N≡C-CH₂CH₂- or HO-N=C(NH₂)-CH₂CH₂-]

In some embodiments, R¹ is

[structures: -CH₂-C(O)OH; -CH₂CH₂-C(O)OH; -CH(-)C(CH₃)₂-C(O)OH; -CH₂-C(CH₃)₂-C(O)OH]

In some embodiments, R¹ is

[structure: -CH(-)C(O)OH]

In some embodiments R¹ is phenyl.
In some embodiments, R¹ is

[structures: 1,2,4-oxadiazole with C(CH₃)₂OH substituent; 1,2,4-oxadiazol-5(4H)-one; tetrazole; piperidinyl; or piperazinyl]

In some embodiments, R¹ is selected from those depicted in Table 1, below.

As defined above and described herein, R² is R, halogen, —C(O)N(R)₂, or —N(R)₂.

In some embodiments, R² is hydrogen.
In some embodiments, R² is R.
In some embodiments, R² is halogen.
In some embodiments, R² is —C(O)N(R)₂, or —N(R)₂.
In some embodiments, R² is —C(O)N(R)₂, or —N(R)₂ wherein each R is independently hydrogen or an optionally substituted group selected from $C_{1-6}$ aliphatic, a 3-8 member saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur.

In some embodiments, R² is —C(O)N(R)₂, or —N(R)₂ wherein the two R groups on the nitrogen are taken together with their intervening atoms to form an optionally substituted 5-6 membered heterocyclic ring having 0-1 heteroatoms in addition to the nitrogen attached thereto wherein such heteroatom is oxygen, nitrogen, or sulfur.

In some embodiments, R² is —N(R)₂ wherein the two R groups on the nitrogen are taken together with their intervening atoms to form a 5-6 membered heterocyclic ring having no heteroatom in addition to the nitrogen attached thereto, and wherein such 5-6 membered heterocyclic ring is optionally substituted 1-6 times by $C_{1-3}$ aliphatic or halogen.

In some embodiments, R² is —NCH₂CH₃ or —N(CH₂)₂N(CH₃)₂.

In some embodiments, R² is

[structure: cyclopropylmethyl-N-]

In some embodiments, R² is

[structures: pyrrolidinyl, piperidinyl, morpholinyl, or piperazinyl-N-methyl]

In some embodiments, R² is

[structures: 3,3-difluoropyrrolidinyl or 3,3,4,4-tetrafluoropyrrolidinyl]

In some embodiments, R² is

[structure: 3-phenyl-1,2,4-oxadiazol-5-yl]

In some embodiments, R² is selected from those depicted in Table 1, below.

As defined above and described herein, R³ is hydrogen or an electron withdrawing group.

In some embodiments, R³ is hydrogen.
In other embodiments, R³ is an electron withdrawing group. Electron withdrawing groups are well-known to one of ordinary skill in the art and include those described in detail in *March's Advanced Organic Chemistry*, 5th Ed., Ed.: Smith, M. B. and March, J., John Wiley & Sons, New York: 2001.

In some embodiments, R³ is an electron withdrawing group selected from halogen, —CN, —NO₂, or $C_{1-4}$ aliphatic substituted with 1-9 halogens.

In some embodiments, $R^3$ is halogen.
In some embodiments, $R^3$ is fluoro, chloro, or bromo.
In some embodiments, $R^3$ is fluoro.
In some embodiments, $R^3$ is selected from

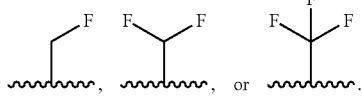

In some embodiments, $R^3$ is

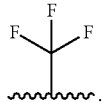

In some embodiments $R^3$ is selected from those depicted in Table 1, below.

As defined above and described herein, R is independently hydrogen or an optionally substituted group selected from $C_{1-6}$ aliphatic, a 3-8 member saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur; or two R groups on the same nitrogen are taken together with their intervening atoms to form an optionally substituted 5-6 membered heterocyclic ring having 0-1 heteroatoms in addition to the nitrogen attached thereto wherein such heteroatom is oxygen, nitrogen, or sulfur.

In some embodiments R is selected from those depicted in Table 1, below.

As defined above and described herein, $L^1$ is a covalent bond or a $C_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —C(F)$_2$—, —N(R)—, —C(O)N(R)—, —RNC(O)—, —OC(O)N(R)—, —N(R)C(O)N(R)—, or -Cy-.

In some embodiments, $L^1$ is a covenant bond.

In some embodiments, $L^1$ is a $C_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —C(F)$_2$—, —N(R)—, —C(O)N(R)—, —RNC(O)—, —OC(O)N(R)—, or —N(R)C(O)N(R)—.

In some embodiments, $L^1$ is a $C_{1-4}$ bivalent straight or branched saturated or unsaturated hydrocarbon chain wherein 1-2 methylene units of the chain are independently and optionally replaced with —O—, —C(R)$_2$—, —C(O)N(R)—, or —RNC(O)—.

In some embodiments, $L^1$ is a $C_{1-4}$ bivalent straight saturated or unsaturated hydrocarbon chain wherein 1-2 methylene units of the chain are independently and optionally replaced with —O—, —C(R)$_2$—, —C(O)N(R)—, or —RNC(O)—.

In some embodiments, $L^1$ is a $C_{1-4}$ bivalent branched saturated or unsaturated hydrocarbon chain wherein 1-2 methylene units of the chain are independently and optionally replaced with —O—, —C(R)$_2$—, —C(O)N(R)—, or —RNC(O)—.

In some embodiments, $L^1$ is —O—.
In some embodiments, $L^1$ is

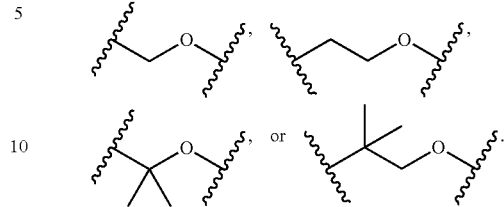

In some embodiments, $L^1$ is

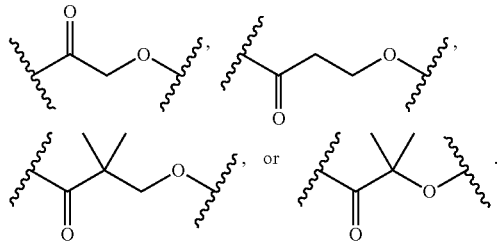

In some embodiments $L^1$ is selected from those depicted in Table 1, below.

As defined above and described herein, $L^2$ is a covalent bond or a $C_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —CH(R)—, —C(F)$_2$—, —N(R)—, —C(O)N(R)—, —RNC(O)—, —OC(O)N(R)—, or —N(R)C(O)N(R)—.

In some embodiments, $L^2$ is a covalent bond.

In other embodiments, $L^2$ is a $C_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —CH(R)—, —C(F)$_2$—, —N(R)—, —C(O)N(R)—, —RNC(O)—, —OC(O)N(R)—, or —N(R)C(O)N(R)—.

In some embodiments, $L^2$ is a $C_{1-4}$ bivalent straight or branched saturated or unsaturated hydrocarbon chain wherein 1 methylene unit of the chain is replaced with —O—, —C(O)—, —C(O)O—, —OC(O)—, —C(R)$_2$—, —C(F)$_2$—, —N(R)—, —C(O)N(R)—, —RNC(O)—.

In some embodiments, $L^2$ is a $C_{1-4}$ bivalent straight or branched saturated or unsaturated hydrocarbon chain.

In some embodiments, $L^2$ is —C(O)—.
In some embodiments, $L^2$ is —CH$_2$— or —(CH$_2$)$_2$—.
In some embodiments $L^2$ is selected from those depicted in Table 1, below.

As defined generally above, each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur.

In some embodiments, -Cy- is a bivalent optionally substituted 3-8 membered saturated or partially unsaturated monocyclic carbocyclic ring. In some embodiments, -Cy- is an optionally substituted phenylene. In some embodiments, -Cy- is an optionally substituted 4-8 membered saturated or partially unsaturated monocyclic heterocyclic ring having 1-3 heteroatoms independently selected from nitrogen, oxygen, or sulfur. In some embodiments, -Cy- is an optionally substituted 5-6 membered monocyclic heteroaromatic ring having 1-4 heteroatoms independently selected from nitrogen, oxygen, or sulfur. In some embodiments, -Cy- is an optionally substituted 8-10 membered bicyclic or bridged bicyclic saturated or partially unsaturated heterocyclic ring having 1-5 heteroatoms independently selected from nitrogen, oxygen, or sulfur. In some embodiments, -Cy- is an optionally substituted 8-10 membered bicyclic or bridged bicyclic heteroaromatic ring having 1-5 heteroatoms independently selected from nitrogen, oxygen, or sulfur.

In some embodiments, -Cy- is

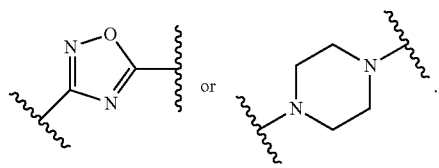 [SMILES: *c1noc(*)n1 ; *N1CCN(*)CC1]

In some embodiments, -Cy- is selected from those depicted in Table 1, below.

Is some embodiments, the present invention provides a compound of Formula II:

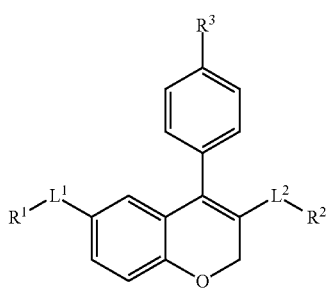

or a pharmaceutically acceptable salt thereof, wherein each $R^1$, $R^2$, $R^3$, R, $L^1$, $L^2$, and -Cy- is defined above and described in the embodiments herein, both singly and in combination.

Is some embodiments, the present invention provides a compound of Formula III:

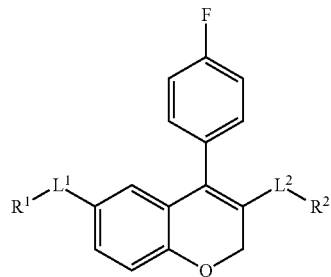

or a pharmaceutically acceptable salt thereof, wherein each $R^1$, $R^2$, R, $L^1$, $L^2$, and -Cy- is defined above and described in the embodiments herein, both singly and in combination.

Is some embodiments, the present invention provides a compound of Formulae IV-a, IV-b, IV-c, or IV-d:

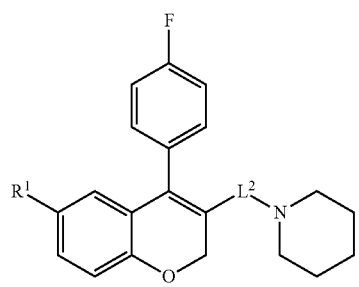

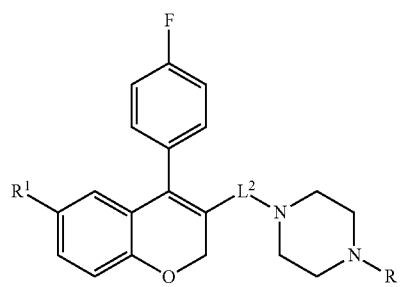

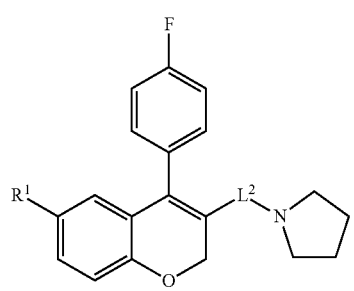

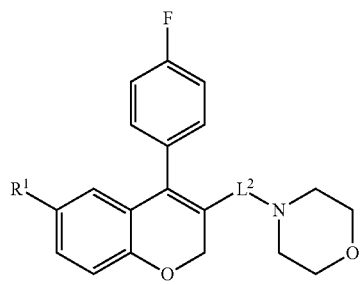

IV-d or a pharmaceutically acceptable salt thereof, wherein each R¹, R, and L², is defined above and described in the embodiments herein, both singly and in combination.

Is some embodiments, the present invention provides a compound of Formulae V-a, V-b, V-c, or V-d:

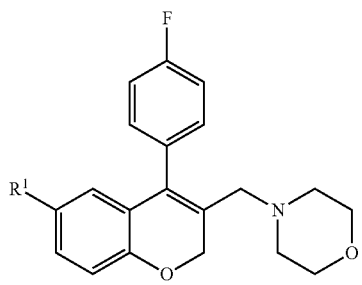

V-d or a pharmaceutically acceptable salt thereof, wherein each R¹ and R is defined above and described in the embodiments herein, both singly and in combination.

Is some embodiments, the present invention provides a compound of any of Formulae VI-a, VI-b, VI-c, and VI-d:

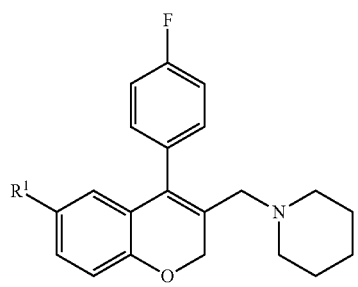

V-a

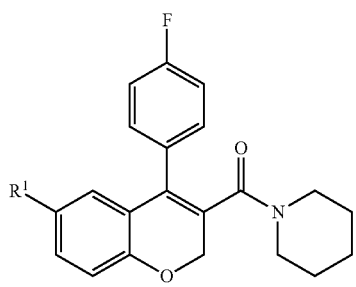

VI-a

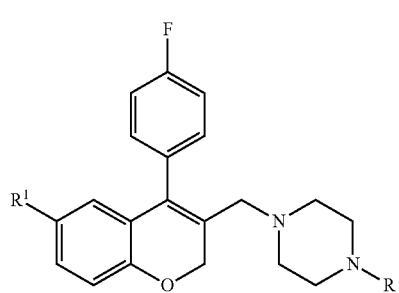

V-b

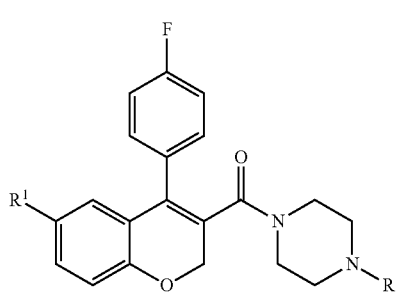

VI-b

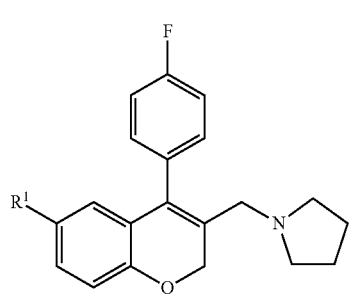

V-c

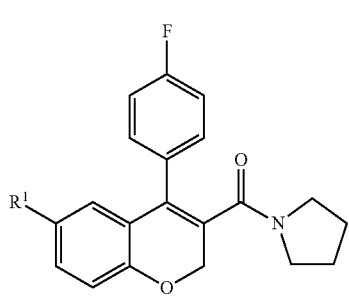

VI-c

-continued

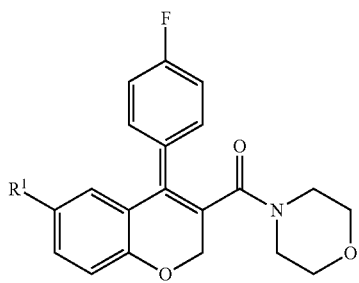

VI-d or a pharmaceutically acceptable salt thereof, wherein each $R^1$ and R, is defined above and described in the embodiments herein, both singly and in combination.

Is some embodiments, the present invention provides a compound of Formula VII:

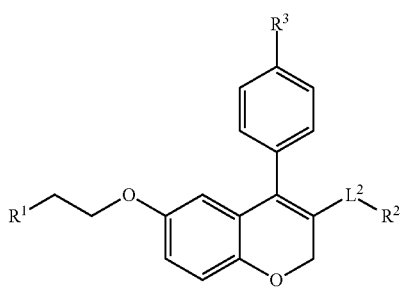

VII or a pharmaceutically acceptable salt thereof, wherein each $R^1$, $R^2$, $R^3$, R, and $L^2$, is defined above and described in the embodiments herein, both singly and in combination.

Is some embodiments, the present invention provides a compound of Formula VIII:

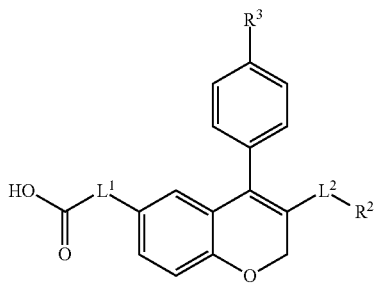

VIII or a pharmaceutically acceptable salt thereof, wherein each $R^2$, $R^3$, $L^1$, and $L^2$, is defined above and described in the embodiments herein, both singly and in combination.

Is some embodiments, the present invention provides a compound of Formula IX:

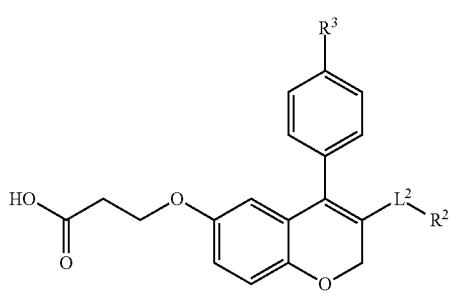

IX or a pharmaceutically acceptable salt thereof, wherein each $R^2$, $R^3$, and $L^2$, is defined above and described in the embodiments herein, both singly and in combination.

Is some embodiments, the present invention provides a compound of Formula X:

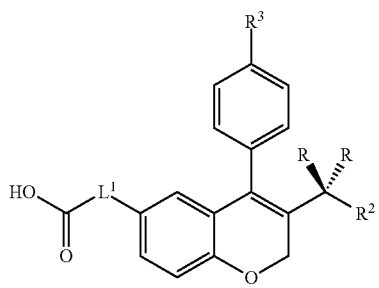

X or a pharmaceutically acceptable salt thereof, wherein each R, $R^2$, $R^3$, and $L^1$, is defined above and described in the embodiments herein, both singly and in combination.

Is some embodiments, the present invention provides a compound of Formulae XI-a or XI-b:

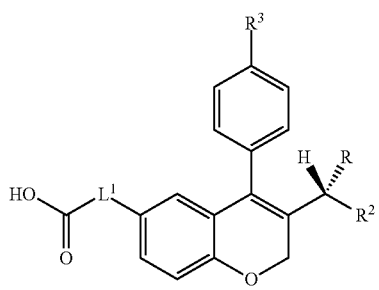

XI-a

-continued

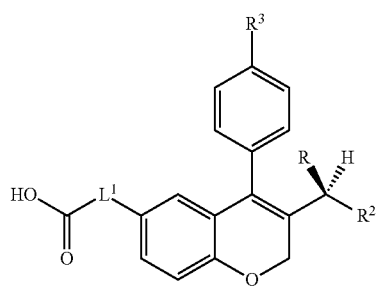
XI-b or a pharmaceutically acceptable salt thereof, wherein each R, R², R³, and L¹, is defined above and described in the embodiments herein, both singly and in combination.

Is some embodiments, the present invention provides a compound of Formula XII:

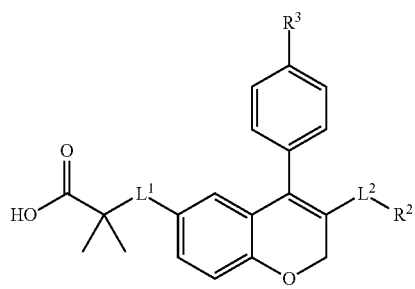
XII or a pharmaceutically acceptable salt thereof, wherein each R², R³, L¹ and L², is defined above and described in the embodiments herein, both singly and in combination.

Is some embodiments, the present invention provides a compound of Formula XIII:

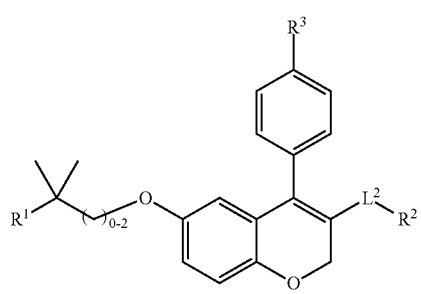
XIII or a pharmaceutically acceptable salt thereof, wherein each R¹, R², R³, and L², is defined above and described in the embodiments herein, both singly and in combination.

Exemplary compounds of the invention are set forth in Table 1, below.

TABLE 1

Exemplary Compounds

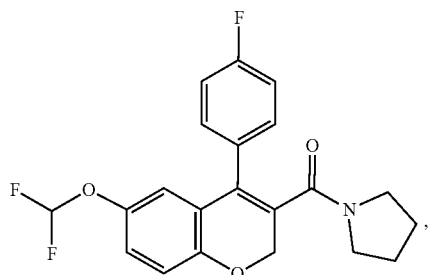
I-1

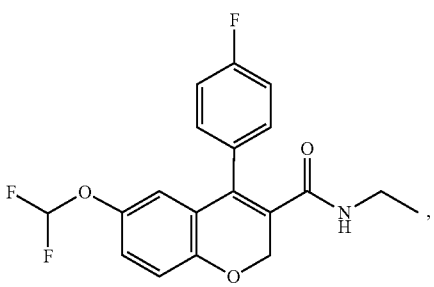
I-2

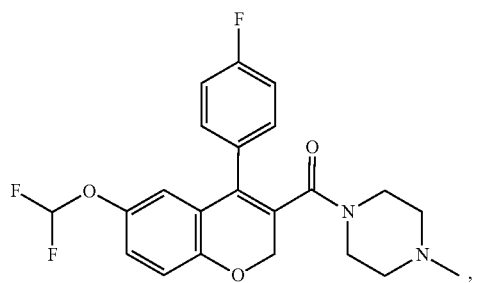 [SMILES: CN1CCN(C(=O)C2=C(c3ccc(F)cc3)c3cc(OC(F)F)ccc3OC2)CC1]
I-3

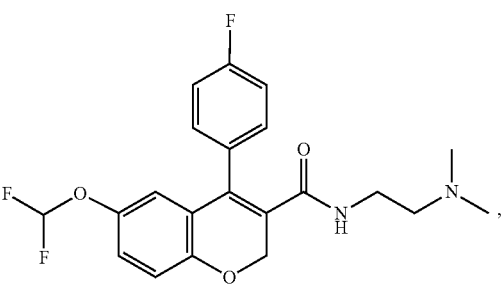 [SMILES: CN(C)CCNC(=O)C1=C(c2ccc(F)cc2)c2cc(OC(F)F)ccc2OC1]
I-4

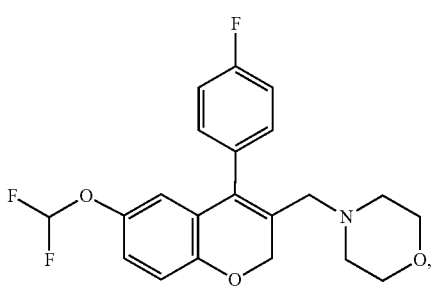 [SMILES: Fc1ccc(C2=C(CN3CCOCC3)COc3ccc(OC(F)F)cc32)cc1]
I-5

TABLE 1-continued

Exemplary Compounds

I-6, I-7, I-8, I-9, I-10, I-11, I-12, I-13, I-14, I-15

TABLE 1-continued
Exemplary Compounds
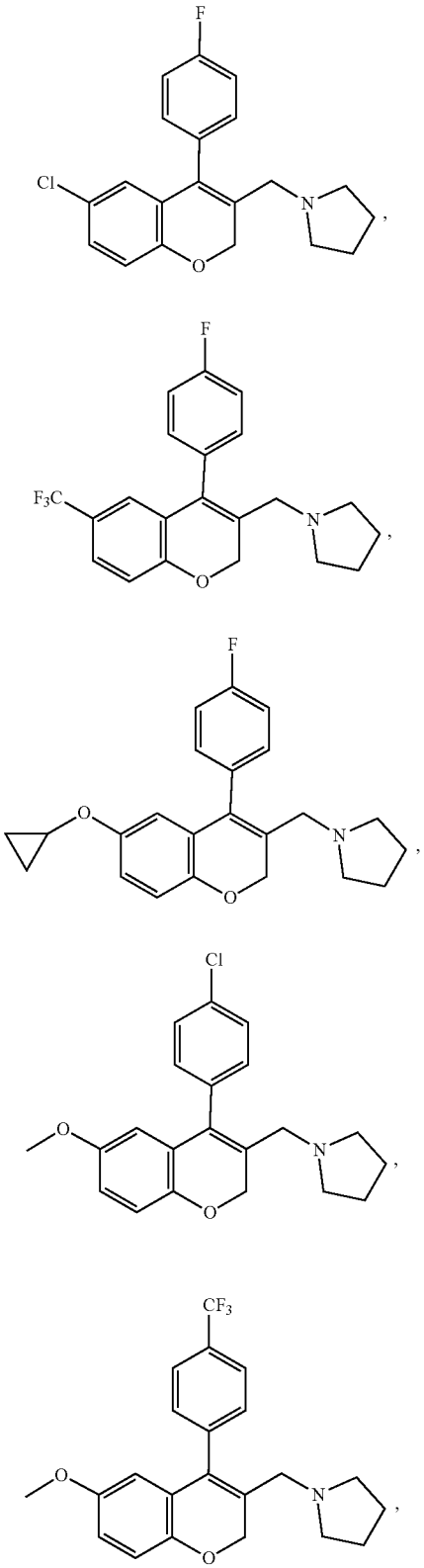
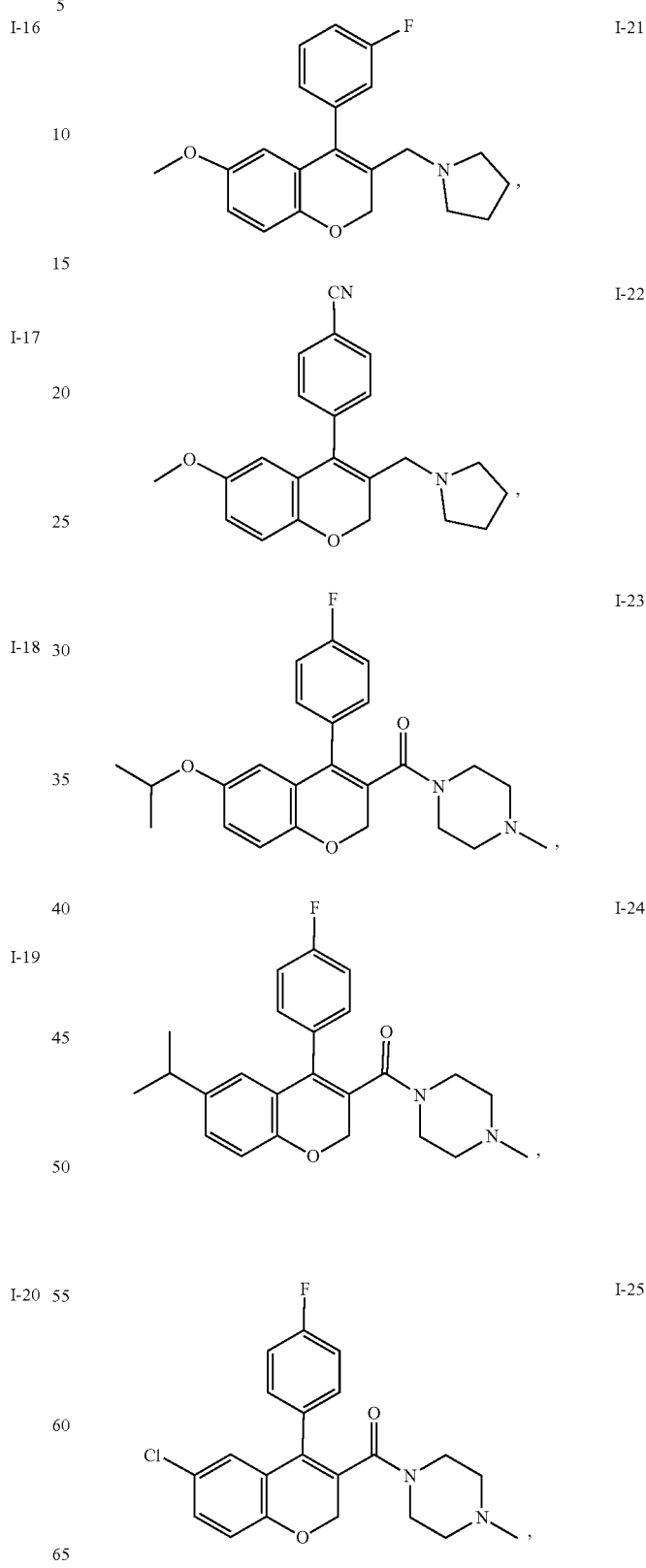

TABLE 1-continued
Exemplary Compounds
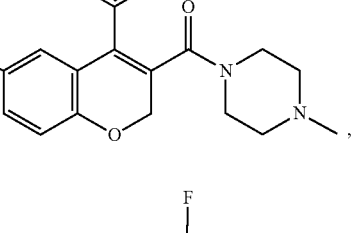  I-26
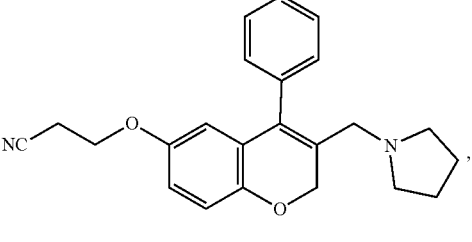  I-27
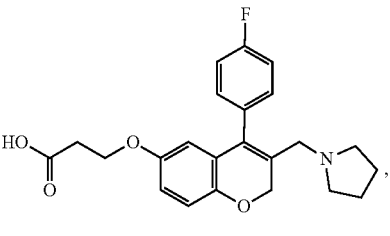 [SMILES: O=C(O)CCOc1ccc2c(c1)C(c1ccc(F)cc1)=C(CN1CCCC1)CO2]  I-28
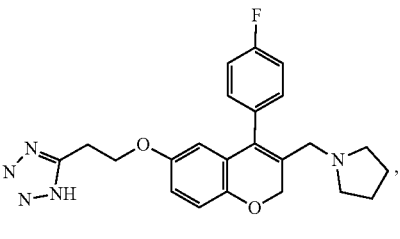  I-29
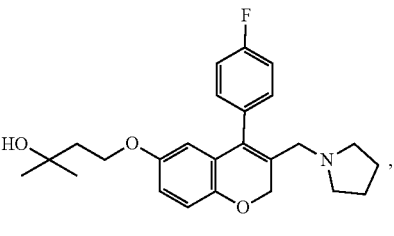 [SMILES: CC(C)(O)CCOc1ccc2c(c1)C(c1ccc(F)cc1)=C(CN1CCCC1)CO2]  I-30
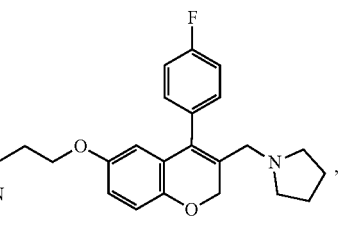  I-31
  I-32
I-33
I-34
I-35
I-36

TABLE 1-continued
Exemplary Compounds
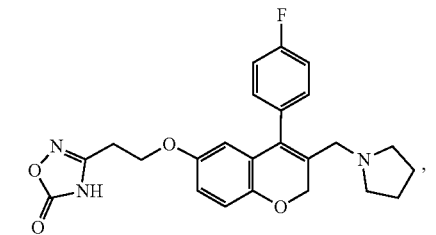 [SMILES: O=c1[nH]c(CCOc2ccc3c(c2)C(c2ccc(F)cc2)=C(CN2CCCC2)CO3)no1]
I-37
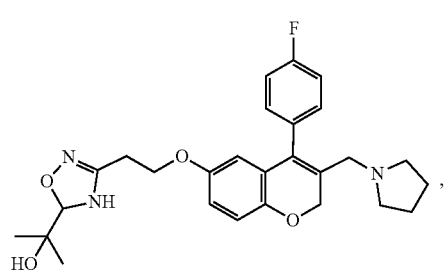 [SMILES: CC(C)(O)C1NC(CCOc2ccc3c(c2)C(c2ccc(F)cc2)=C(CN2CCCC2)CO3)=NO1]
I-38
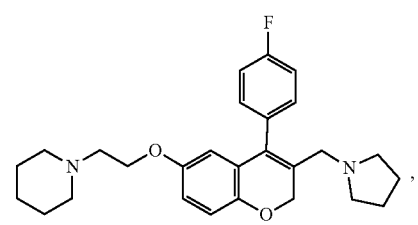 [SMILES: Fc1ccc(C2=C(CN3CCCC3)COc3ccc(OCCN4CCCCC4)cc32)cc1]
I-39
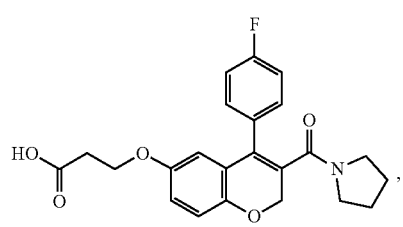
I-40
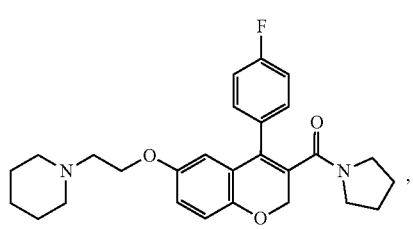 [SMILES: O=C(C1=C(c2ccc(F)cc2)c2cc(OCCN3CCCCC3)ccc2OC1)N1CCCC1]
I-41
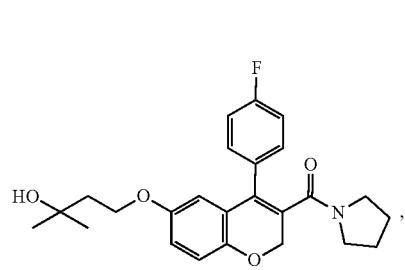 [SMILES: CC(C)(O)CCOc1ccc2c(c1)C(c1ccc(F)cc1)=C(C(=O)N1CCCC1)CO2]
I-42
TABLE 1-continued
Exemplary Compounds
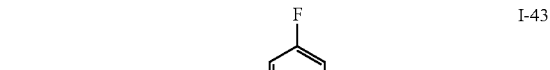
I-43
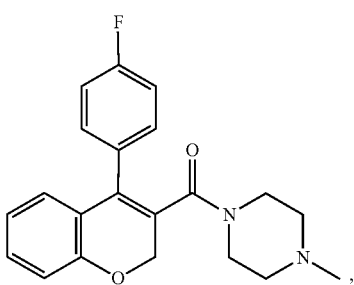 [SMILES: CN1CCN(C(=O)C2=C(c3ccc(F)cc3)c3ccccc3OC2)CC1]
I-44
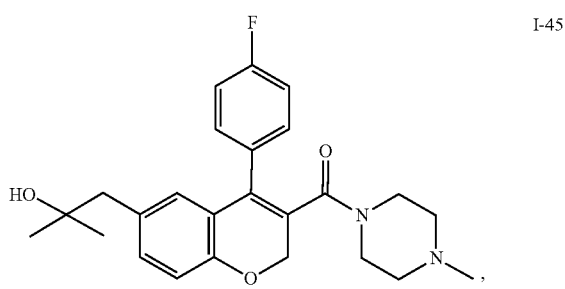
I-45
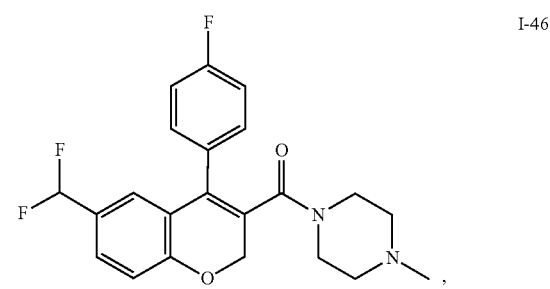
I-46
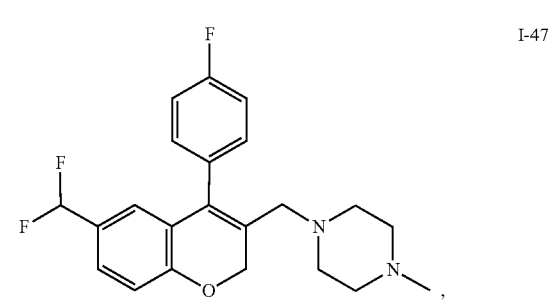
I-47

TABLE 1-continued
Exemplary Compounds
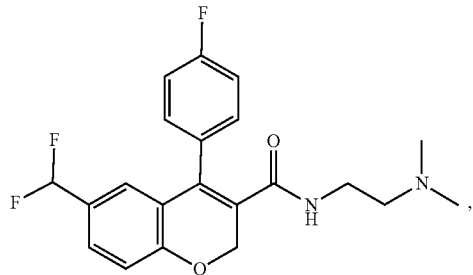 [SMILES: CN(C)CCNC(=O)C1=C(c2ccc(F)cc2)c2cc(C(F)F)ccc2OC1]
I-48
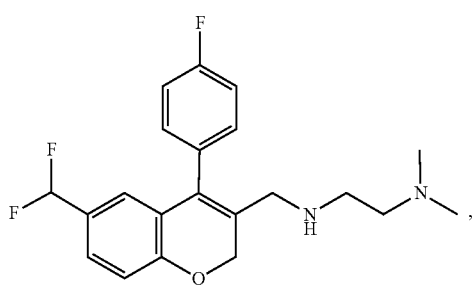 [SMILES: CN(C)CCNCC1=C(c2ccc(F)cc2)c2cc(C(F)F)ccc2OC1]
I-49
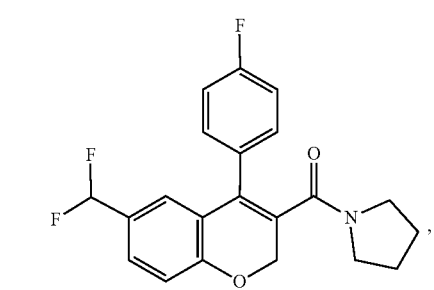 [SMILES: O=C(C1=C(c2ccc(F)cc2)c2cc(C(F)F)ccc2OC1)N1CCCC1]
I-50
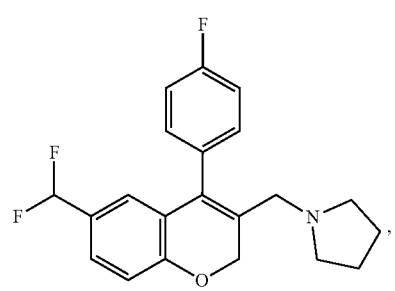 [SMILES: Fc1ccc(C2=C(CN3CCCC3)COc3ccc(C(F)F)cc32)cc1]
I-51
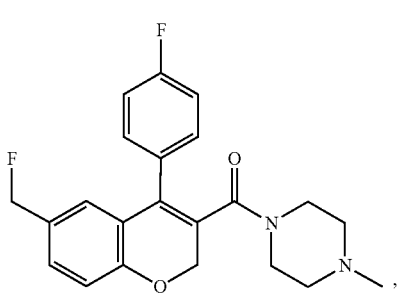 [SMILES: CN1CCN(C(=O)C2=C(c3ccc(F)cc3)c3cc(CF)ccc3OC2)CC1]
I-52
TABLE 1-continued
Exemplary Compounds
I-53
I-54
I-55
I-56
I-57

TABLE 1-continued
Exemplary Compounds
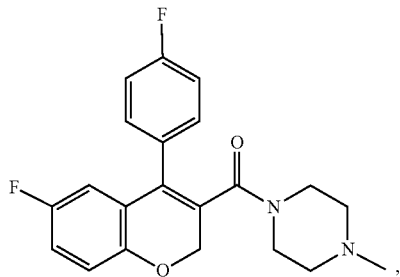 [SMILES: CN1CCN(C(=O)C2=C(c3ccc(F)cc3)c3cc(F)ccc3OC2)CC1] I-58
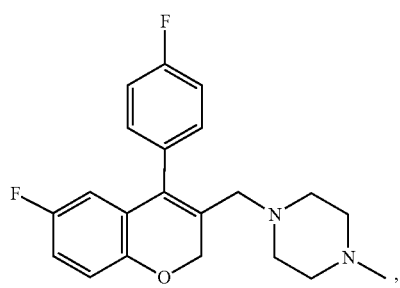 [SMILES: CN1CCN(CC2=C(c3ccc(F)cc3)c3cc(F)ccc3OC2)CC1] I-59
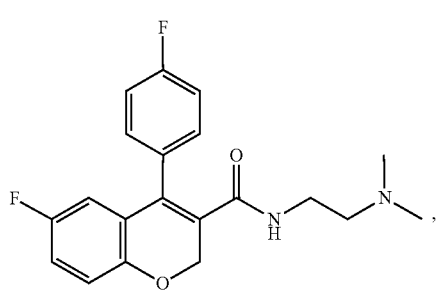 [SMILES: CN(C)CCNC(=O)C1=C(c2ccc(F)cc2)c2cc(F)ccc2OC1] I-60
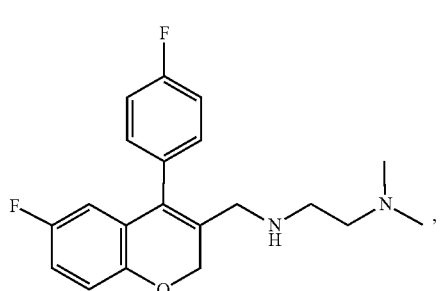 I-61
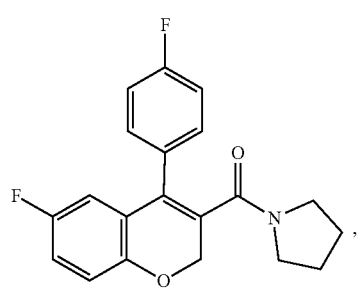 I-62
TABLE 1-continued
Exemplary Compounds
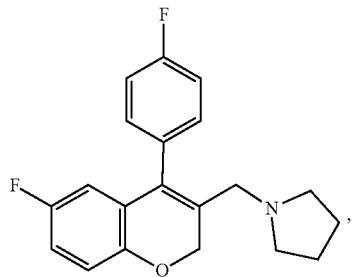 [SMILES: Fc1ccc(C2=C(CN3CCCC3)COc3ccc(F)cc32)cc1] I-63
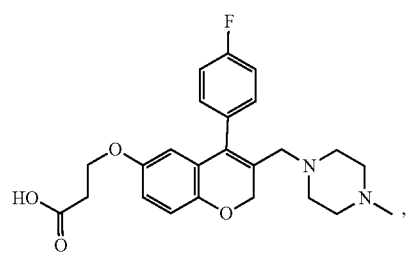 [SMILES: CN1CCN(CC2=C(c3ccc(F)cc3)c3cc(OCCC(=O)O)ccc3OC2)CC1] I-64
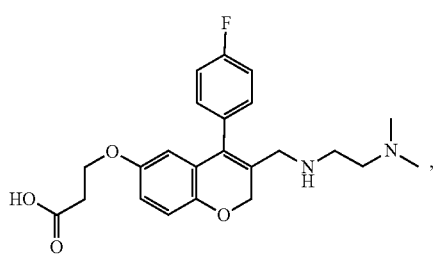 [SMILES: CN(C)CCNCC1=C(c2ccc(F)cc2)c2cc(OCCC(=O)O)ccc2OC1] I-65
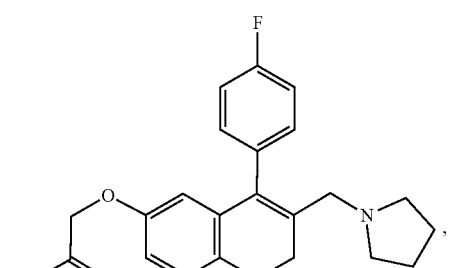 I-65
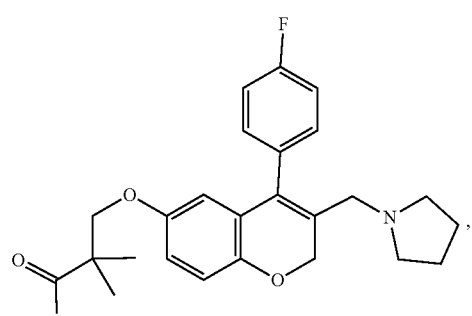 I-66

TABLE 1-continued

Exemplary Compounds

I-67: 4-((4-(4-fluorophenyl)-3-(pyrrolidin-1-ylmethyl)-2H-chromen-6-yl)oxy)butanoic acid I-68: 3-((3-(pyrrolidin-1-ylmethyl)-4-(4-(trifluoromethyl)phenyl)-2H-chromen-6-yl)oxy)propanoic acid I-69: 3-((3-((4-methylpiperazin-1-yl)methyl)-4-(4-(trifluoromethyl)phenyl)-2H-chromen-6-yl)oxy)propanoic acid I-70: 3-((3-(((2-(dimethylamino)ethyl)amino)methyl)-4-(4-(trifluoromethyl)phenyl)-2H-chromen-6-yl)oxy)propanoic acid I-71: 3-((3-((3,3-difluoropyrrolidin-1-yl)methyl)-4-(4-fluorophenyl)-2H-chromen-6-yl)oxy)propanoic acid I-72: 3-((4-(4-fluorophenyl)-3-((3,3,4,4-tetrafluoropyrrolidin-1-yl)methyl)-2H-chromen-6-yl)oxy)propanoic acid I-73: 2-((3-((3,3-difluoropyrrolidin-1-yl)methyl)-4-(4-fluorophenyl)-2H-chromen-6-yl)oxy)acetic acid I-74: 2-((4-(4-fluorophenyl)-3-((3,3,4,4-tetrafluoropyrrolidin-1-yl)methyl)-2H-chromen-6-yl)oxy)acetic acid I-76: 3-((3-(morpholinomethyl)-4-(4-(trifluoromethyl)phenyl)-2H-chromen-6-yl)oxy)propanoic acid I-76: 3-((4-(4-fluorophenyl)-3-(morpholinomethyl)-2H-chromen-6-yl)oxy)propanoic acid TABLE 1-continued Exemplary Compounds

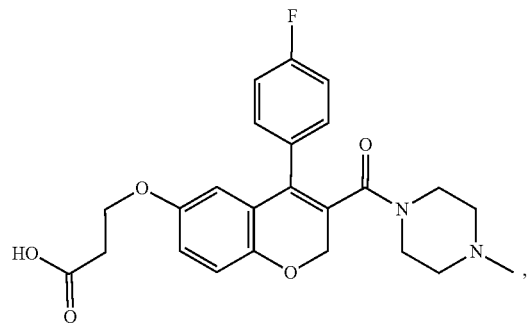 [SMILES: CN1CCN(C(=O)C2=C(c3ccc(C(F)(F)F)cc3)c3cc(OCCC(=O)O)ccc3OC2)CC1]
I-77

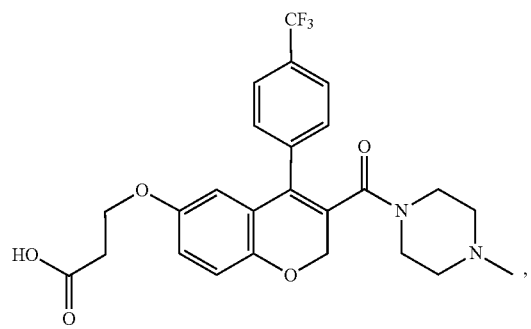
I-78

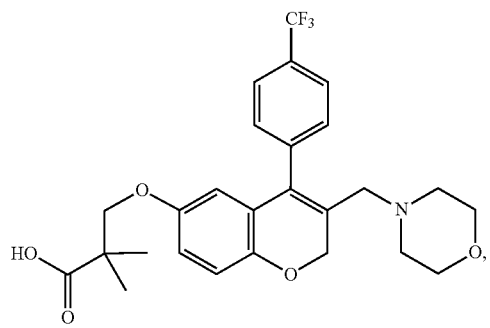 [SMILES: CC(C)(COc1ccc2c(c1)C(c1ccc(C(F)(F)F)cc1)=C(CN1CCOCC1)CO2)C(=O)O]
I-79

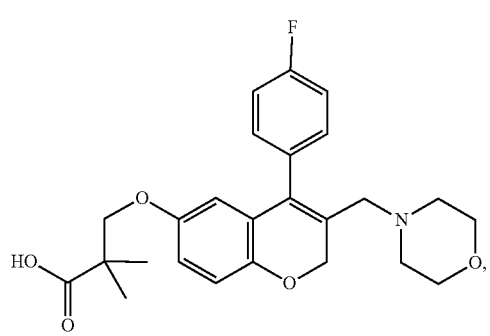 [SMILES: CC(C)(COc1ccc2c(c1)C(c1ccc(F)cc1)=C(CN1CCOCC1)CO2)C(=O)O]
I-80

TABLE 1-continued

Exemplary Compounds

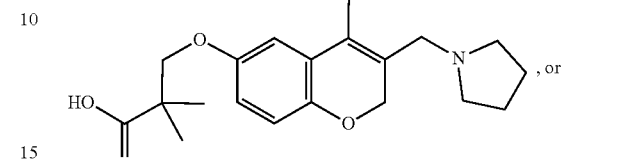
I-81, or

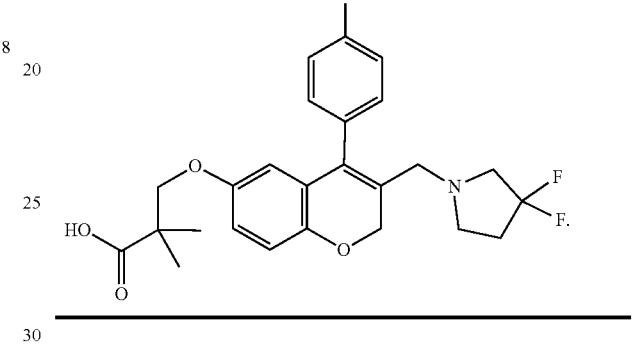
I-82

In some embodiments, the present invention provides a compound set forth in Table 1, above, or a pharmaceutically acceptable salt thereof.

Uses, Formulations, and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate the interaction between TCR and Nck, in a biological sample or in a patient. In certain embodiments, the amount of compound in compositions of this invention is such that is effective to measurably modulate the interaction between TCR and Nck in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants, or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see supra) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulation of TCR signaling and T-cell activation via modulation of the interaction between TCR and Nck.

The activity of a compound utilized in this invention as a modulator of the TCR-Nck interaction, may be assayed in vitro, in vivo or in a cell line. In vitro assays include, for example, assays that measure the proliferation of T-lymphocytes (e.g., Tse, W. T. et al., Transplantation, 2003, 75(3): 389-97, whose contents is incorporated here by reference); measure the polymerization of the actin cytoskeleton induced in T-cells after TCR stimulation (e.g., Fuller, C. L. et al., Immunol. Rev. 2003, 292: 220-36, whose contents is incorporated here by reference); and measure the secretion of cytokines by T-cells caused by stimulation of the TCR (e.g., Finco, D. et al., Cytokine, 2014, 66(2): 143-55, whose contents is incorporated here by reference). In vivo assays include standard animal models for immune and autoimmune disease, which are well-known and are part of the state of the art such as, for example, delayed hypersensitivity (e.g., Kudlacz, E. et al., Am. J. Transplant., 2004, 4(1): 51-7, whose contents is incorporated here by reference); models for rheumatoid arthritis (e.g., Holmdahl, R. et al., APMIS, 1989, 97(7): 575-84, whose contents is incorporated here by reference); models of multiple sclerosis (experimental autoimmune encephalomyelitis) (e.g., Gonzalez-Rey, E. et al., Am. J. Pathol. 2006, 168(4): 1179-88, whose contents is incorporated here by reference; and models of transplant rejection (see, e.g., various animal models described in the references above in relation to the treatment of transplant rejection, incorporated here by reference).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are modulators of the TCR-Nck interaction and are therefore useful for treating one or more disorders associated with activity of TCR. Thus, in certain embodiments, the present invention provides a method for treating a TCR-Nck mediated disorder comprising the step of administering to a patient in need thereof a compound of the present invention, or pharmaceutically acceptable composition thereof.

As used herein, the terms "TCR-Nck mediated" disorders, diseases, and/or conditions means any disease, or other deleterious condition, in which the TCR is known to play a role. Accordingly, another embodiment of the present invention relates to treating or lessening the severity of one or more diseases in which TCR is known to play a role. Such TCT-Nck mediated disorders include, without limitation, autoimmune and inflammatory disorders; disorders associated with transplantation; proliferative disorders; and neurological disorders. (See, e.g., O'Sea, J. et al., Nat. Rev. Drug Doscpv. 2004, 3(7): 555-64; Cetkovic-Cvrlje, M. et al., Curr. Pharm. Des. 2004, 10(15): 1767-84; Cetkovic-Cvrlje, M. et al., Arch. Immunol. Ther. Exp. 2004, 52(2): 69-82).

Autoimmune and Inflammatory Disorders

As used herein, "autoimmune and inflammatory disorder" refers to those diseases, illnesses, or conditions engendered when the host's systems are attacked by the host's own immune system. The targets of autoimmune interaction can range anywhere from the cellular level (e.g., myelin basic protein in multiple sclerosis, or the thyrotropin receptor in Graves' disease) to organ specific effects in rheumatoid arthritis or Crohn's disease to system wide effects as seen in systemic lupus erythematosus. Some of the events that have been postulated in the causation of autoimmune diseases have included cytokine over expression, for example TNF-α, IL-2, or IL-2 receptor in inflammatory bowel disease, or under expression (IL-10 under expression in Type 1 diabetes), to defects in allele expression (HLA Class I B27 in ankylosing spondylitis), to altered expression of apoptosis proteins (under expression of Fas in autoimmune lymphoproliferative syndrome type I (ALPS 1). See "Harrison's Principles of Internal Medicine", 16th ed., McGraw-Hill, N.Y., 2005; Chapter 295 for additional information on autoimmune diseases.

In certain embodiments, the autoimmune or inflammatory disorder is Addison's disease, agammaglobulinemia, alopecia areata, alopecia universalis, amyloidosis, ankylosing spondylitis, anti-GBM/anti-TBM nephritis, antiphospholipid syndrome, autoimmune angioedema, autoimmune dysautonomia, autoimmune encelphalomyelitis, autoimmune hepatitis, autoimmune inner ear disease (Meniere's disease), autoimmune myocarditis, autoimmune pancreatitis, autoimmune retinopathy, autoimmune urticarial, axon and neuronal neropathy, Baló disease, Behçet's disease, benign mucosal pemphigoid, bullous pemhigoid, Castleman disease, Celiac disease, Chagasa disease, chronic inflammatory demyelination polyneuropathy, chronic recurrent multifocal osteomyelitis, Churg-Strauss, cicatrical pemphioid, Cogan's syndrome, cold agglutinin disease, congenital heart block, Coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, essential mixed cryoglobulinemia, Evan's syndrome, fibromyalgia, fibrosing alveolitis, giant cell arteritis, giant cell myocarditis, glomerulonephritis, Goodpasture's syndrome, granulomatosis with polyangitis, Grave's disease, Guillain-Barre Syndrome, Hashimoto's thyroiditis, hemolytic anemia, Henoch-Schonlein purpura, herpes gestationis or pemphigoid gestationis, hypogammalglobulinemia, IgA nephropathy, IgG4-related sclerosing disease, immune thrombocytopenic purpura, inclusion body myositis, inflammatory bowel disease, interstitial cystitis, juvenile arthritis, juvenile diabetes, juvenile myositis, Kawasaki disease, Lambert-Eaton syndrome, leukocytoclasic vasculitis, lichen planus, lichen sclerosis, ligneous conjunctivitis, linear IgA disease, lupus erythematosus, Lyme disease chronic, Lyme neuroborreliosis, microscopic polyangitis, mixed connective tissue disease, Mooren's ulcer, Mucha-Habermann disease, multiple sclerosis, myasthenia gravis, myositis, neuromyelitis optica, neutropenia, ocular cicatricial pemphigold, optic neuritis, palindromic rheumatism, PANDAS, paraneoplastic cerebellar degeneration, paroxysmal nocturnal hemoglobunuria, Parry-Romberg syndrome, Pars planitis, Parsonage-Turner syndrome, pemphigus, peripheral neuropathy, perivenous encephalomyelitis, pernicious anemia, POEMS syndrome, polyarteritis *nodosa*, polyglandular syndromes types I, II, and III, polymyalgia rhematica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis, thrombocytopenic purpura (TTP), Tolosa-Hunt syndrome, transverse myelitis, type 1 diabetes, ulcerative colitis, undifferentiated connective tissue disease, uveitis, vasculitis, vitiligo and Wegener's granulomatosis (or granulomatosis with polyangiitis).

Disorders Associated with Transplantation

In some embodiments, the disorder is associated with transplantation. In some embodiments the disorder associated with transplantation is transplant rejection. In some embodiments the disorder associated with transplantation is graft-versus-host disease.

Proliferative Disorders

In some embodiments, the disorder is a proliferative disorder. In some embodiments, the proliferative disorder is a cancer.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancer cells. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. An "adenocarcinoma" refers to a carcinoma derived from glandular tissue or in which the tumor cells form recognizable glandular structures. The term "sarcoma" is art recognized and refers to malignant tumors of mesenchymal derivation.

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

In some embodiments the proliferative disorder is a hematological cancers. In some embodiments the proliferative disorder is a leukemia. In some embodiments, the leukemia is a T-cell leukemia.

Neurological Disorders

In some embodiments, the disorder is a neurological disorder. In some embodiments, the neurological disorder is Balo's disease, chronic inflammatory demyelinating polyneuropathy, Devic's neuromyelitis optica, Marburg acute multiple sclerosis, multiple sclerosis, Schilder's disease, or perivenous encephalomyelitis.

Acceptable Compositions

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well-known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Methods of Treatment

In other embodiments, the present invention provides a method for treating a disorder mediated by TCR-Nck interaction in a patient in need thereof, comprising the step of administering to said patient a compound according to the present invention or pharmaceutically acceptable composition thereof. In some embodiments the method of modulating TCR-Nck is used to treat autoimmune and inflammatory disorders; disorders associated with transplantation; proliferative disorders; and neurological disorders.

In some embodiments, the method of modulating TCR-Nck is used to treat alopecia areata. (See, e.g., Petukhova, L. et al., Nature, 2010, 466(7302): 113-17). Accordingly, in some embodiments, the present invention provides a method of treating alopecia areata, in a patient in need thereof, comprising the step of administering to said patient a provided compound or a pharmaceutically acceptable salt thereof.

In some embodiments, the method of modulating TCR-Nck is used to treat ankylosing spondylitis. (See, e.g., Smith, J. A., Curr Allergy Asthma Rep. 2015, 15(1): 489). Accordingly, in some embodiments, the present invention provides a method of treating ankylosing spondylitis, in a patient in need thereof, comprising the step of administering to said patient a provided compound or a pharmaceutically acceptable salt thereof.

In some embodiments, the method of modulating TCR-Nck is used to treat asthma. (See, e.g., Robinson, D. S., J. Allergy Clin. Immunol., 2010, 126(6): 1081-91). Accordingly, in some embodiments, the present invention provides a method of treating asthma, in a patient in need thereof, comprising the step of administering to said patient a provided compound or a pharmaceutically acceptable salt thereof.

In some embodiments, the method of modulating TCR-Nck is used to treat autoimmune hepatitis. (See, e.g., Manns, M. P. et al., Hepatology, 2010, 51(6), 2193-213. Accordingly, in some embodiments, the present invention provides a method of treating autoimmune hepatitis, in a patient in need thereof, comprising the step of administering to said patient a provided compound or a pharmaceutically acceptable salt thereof.

In some embodiments, the method of modulating TCR-Nck is used to treat autoimmune lymphoproliferative syndrome (ALPS). (See, e.g., Sneller, M. C. et al., Curr. Opin. Rheumatology, 2003, 15(4) 417-21). Accordingly, in some embodiments, the present invention provides a method of treating ALPS, in a patient in need thereof, comprising the step of administering to said patient a provided compound or a pharmaceutically acceptable salt thereof.

In some embodiments, the method of modulating TCR-Nck is used to autoimmune myocarditis. (See, e.g., Caforio, A. L. and Iliceto, S., Curr. Opin. Cardiol., 2008, 23(3): 219-26). Accordingly, in some embodiments, the present invention provides a method of treating autoimmune myocarditis, in a patient in need thereof, comprising the step of administering to said patient a provided compound or a pharmaceutically acceptable salt thereof.

In some embodiments, the method of modulating TCR-Nck is used to autoimmune orchitis. (See, e.g., Silva, C. A. et al., Autoimmun Rev., 2014, 13(4-5): 431-34). Accordingly, in some embodiments, the present invention provides a method of treating autoimmune orchitis, in a patient in need thereof, comprising the step of administering to said patient a provided compound or a pharmaceutically acceptable salt thereof.

In some embodiments, the method of modulating TCR-Nck is used to autoimmune pancreatitis. (See, e.g., Fan, B. G. and Andren-Sandberg, A., N. Am. J. Med. Sci. 2009, 1(2): 148-51). Accordingly, in some embodiments, the present invention provides a method of treating autoimmune pancreatitis, in a patient in need thereof, comprising the step of administering to said patient a provided compound or a pharmaceutically acceptable salt thereof.

In some embodiments, the method of modulating TCR-Nck is used to treat atopic dermatitis. (See, e.g., Nograles, K. E. et al., J. Allergy Clin. Immunol., 2009, 123(6): 1244-52). Accordingly, in some embodiments, the present invention provides a method of treating systemic atopic dermatitis, in a patient in need thereof, comprising the step of administering to said patient a provided compound or a pharmaceutically acceptable salt thereof.

In some embodiments, the method of modulating TCR-Nck is used to treat Behçet's disease. (See, e.g., Direskeneli, H., Genetics Research International, 2013, Article ID 249157 doi:10.1155/2013/249157). Accordingly, in some embodiments, the present invention provides a method of treating Behçet's disease, in a patient in need thereof, comprising the step of administering to said patient a provided compound or a pharmaceutically acceptable salt thereof.

In some embodiments, the method of modulating TCR-Nck is used to treat Castleman disease. (See, e.g., Al-Maghrabi, J. et al., Histopathology, 2005, 48(3): 233-38). Accordingly, in some embodiments, the present invention provides a method of treating Castleman disease, in a patient in need thereof, comprising the step of administering to said patient a provided compound or a pharmaceutically acceptable salt thereof.

In some embodiments, the method of modulating TCR-Nck is used to treat Celiac disease. (See, e.g., Mazzarella, G., World J. Gastroenterol., 2015, 21(24): 7349-56). Accordingly, in some embodiments, the present invention provides a method of treating Celiac disease, in a patient in need thereof, comprising the step of administering to said patient a provided compound or a pharmaceutically acceptable salt thereof.

In some embodiments, the method of modulating TCR-Nck is used to treat chronic inflammatory demyelinating polyneuropathy. (See, e.g., Notturno, F. et al., J. Neuroimmunol. 2008, 197(2): 124-7). Accordingly, in some embodiments, the present invention provides a method of treating chronic inflammatory demyelinating polyneuropathy, in a patient in need thereof, comprising the step of administering to said patient a provided compound or a pharmaceutically acceptable salt thereof.

In some embodiments, the method of modulating TCR-Nck is used to treat Cogan's syndrome. (See, e.g., Greco, A. et al., Autoimmunity Rev. 2013, 12(3): 396-400). Accordingly, in some embodiments, the present invention provides a method of treating Cogan's syndrome, in a patient in need thereof, comprising the step of administering to said patient a provided compound or a pharmaceutically acceptable salt thereof.

In some embodiments, the method of modulating TCR-Nck is used to treat Churg-Strauss syndrome. (See, e.g., Guida, G. et al., Clin. Immunol., 2008 128(1): 94-102). Accordingly, in some embodiments, the present invention provides a method of treating Churg-Strauss syndrome, in a patient in need thereof, comprising the step of administering to said patient a provided compound or a pharmaceutically acceptable salt thereof.

In some embodiments, the method of modulating TCR-Nck is used to treat Crohn's disease. (See, e.g., Roche, J. K. et al., J. Clin. Invest. 1985, 75(2):522-530; Marks, D. J. and Segal, A. W. J. Pathol. 2008, 214(2): 260-66; Cobrin, G. M. and Abreu, M. T. Immunol. Rev. 2005, 206(1): 277-95). Accordingly, in some embodiments, the present invention provides a method of treating Crohn's disease, in a patient in need thereof, comprising the step of administering to said patient a provided compound or a pharmaceutically acceptable salt thereof.

In some embodiments, the method of modulating TCR-Nck is used to treat Evans syndrome. (See, e.g., Teachery, D. T. et al., Blood, 2004, 105(6):2443-48). Accordingly, in some embodiments, the present invention provides a method of treating Evans syndrome, in a patient in need thereof, comprising the step of administering to said patient a provided compound or a pharmaceutically acceptable salt thereof.

In some embodiments, the method of modulating TCR-Nck is used to treat inclusion body myositis. (See, e.g., Kitazawa, M. et al., J. Neuroscience, 2009, 29(19): 6132-41). Accordingly, in some embodiments, the present invention provides a method of treating inclusion body myositis, in a patient in need thereof, comprising the step of administering to said patient a provided compound or a pharmaceutically acceptable salt thereof.

In some embodiments, the method of modulating TCR-Nck is used to treat inflammatory bowel disease. (See, e.g., Zenewicz, L. A. et al., Trends Mol. Med., 2009, 15(5): 199-207). Accordingly, in some embodiments, the present invention provides a method of treating inflammatory bowel disease, in a patient in need thereof, comprising the step of administering to said patient a provided compound or a pharmaceutically acceptable salt thereof.

In some embodiments, the method of modulating TCR-Nck is used to treat Kawasaki disease. (See, e.g., Onouchi, Y. et al., Nature Genetics, 2008, 40: 35-42). Accordingly, in some embodiments, the present invention provides a method of treating Kawasaki disease, in a patient in need thereof, comprising the step of administering to said patient a provided compound or a pharmaceutically acceptable salt thereof.

In some embodiments, the method of modulating TCR-Nck is used to treat Lyme disease (chronic). (See, e.g., Singh, S. K. and Girschick, H. J. Paediatric Rheumatology, 2004, 10(7): 598-614; Raveche, E. S. et al., J. Clin. Microbiol. 2005, 43(2): 850-56). Accordingly, in some embodiments, the present invention provides a method of treating Lyme disease (chronic), in a patient in need thereof, comprising the step of administering to said patient a provided compound or a pharmaceutically acceptable salt thereof.

In some embodiments, the method of modulating TCR-Nck is used to treat multiple sclerosis. (See, e.g., Babbe, H. et al., J. Exp. Med., 2000, 192(3): 393-404; Dai, K. Z. et al., Genes Immun. 2001, 2(5): 263-8). Accordingly, in some embodiments, the present invention provides a method of treating multiple sclerosis, in a patient in need thereof, comprising the step of administering to said patient a provided compound or a pharmaceutically acceptable salt thereof.

In some embodiments, the method of modulating TCR-Nck is used to treat myasthenia gravis. (See, e.g., Meriggioli, M. N. and Sanders, D. B. S., Lancet Neurology, 2009, 8(5): 475-90). Accordingly, in some embodiments, the present invention provides a method of treating myasthenia gravis, in a patient in need thereof, comprising the step of administering to said patient a provided compound or a pharmaceutically acceptable salt thereof.

In some embodiments, the method of modulating TCR-Nck is used to treat psoriasis. (See, e.g., Cai, Y. et al., Cell Mol. Immunol., 2012, 9(4): 302-09). Accordingly, in some embodiments, the present invention provides a method of treating psoriasis, in a patient in need thereof, comprising the step of administering to said patient a provided compound or a pharmaceutically acceptable salt thereof.

In some embodiments, the method of modulating TCR-Nck is used to treat psoriatic arthritis. (See, e.g., Choy, E., Curr. Rheumatol. Rep. Exp., 2007, 9(6): 437-41). Accordingly, in some embodiments, the present invention provides a method of treating psoriatic arthritis, in a patient in need thereof, comprising the step of administering to said patient a provided compound or a pharmaceutically acceptable salt thereof.

In some embodiments, the method of modulating TCR-Nck is used to treat rheumatoid arthritis. (See, e.g., Cope, A. P. et al., Clin. Exp. Rheumatol., 2007, 25(5): S4-11). Accordingly, in some embodiments, the present invention provides a method of treating rheumatoid arthritis, in a patient in need thereof, comprising the step of administering to said patient a provided compound or a pharmaceutically acceptable salt thereof.

In some embodiments, the method of modulating TCR-Nck is used to treat systemic lupus erythematosus. (See, e.g., Crispin, J. C. et al., J. Immunol., 2008, 181(12): 8761-66; Linterman, M. A. et al., J. Exp. Med. 2009, 206(3): 561-76). Accordingly, in some embodiments, the present invention provides a method of treating systemic lupus erythematosus, in a patient in need thereof, comprising the step of administering to said patient a provided compound or a pharmaceutically acceptable salt thereof.

In some embodiments, the method of modulating TCR-Nck is used to treat type I diabetes. (See, e.g., Roep, B. O., Diabetologia, 46(3): 305-21). Accordingly, in some embodiments, the present invention provides a method of treating type I diabetes, in a patient in need thereof, comprising the step of administering to said patient a provided compound or a pharmaceutically acceptable salt thereof.

In some embodiments, the method of modulating TCR-Nck is used to treat ulcerative colitis. (See, e.g., Kappeler, A. and Mueller, C., Histol Histopathol., 2000, 15(1): 167-72). Accordingly, in some embodiments, the present invention provides a method of treating ulcerative colitis, in a patient in need thereof, comprising the step of administering to said patient a provided compound or a pharmaceutically acceptable salt thereof.

In some embodiments, the method of modulating TCR-Nck is used to treat uveitis. (See, e.g., Horai, R. et al., Immunity, 2015, 43(2): 343-53). Accordingly, in some embodiments, the present invention provides a method of treating uveitis, in a patient in need thereof, comprising the step of administering to said patient a provided compound or a pharmaceutically acceptable salt thereof.

In some embodiments, the method of modulating TCR-Nck is used to treat vitiligo. (See, e.g., Van den Wijngaard, R. et al., Lab Invest. 2000, 80(8): 1299-309). Accordingly, in some embodiments, the present invention provides a method of treating vitiligo, in a patient in need thereof, comprising the step of administering to said patient a provided compound or a pharmaceutically acceptable salt thereof.

In some embodiments, the method of modulating TCR-Nck is used to treat rejection of transplants. (See, e.g., Issa, F. et al., Expert Rev. Clin. Immunol. 2010, 6(1): 155-69). Accordingly, in some embodiments, the present invention provides a method of treating rejection of transplants, in a patient in need thereof, comprising the step of administering to said patient a provided compound or a pharmaceutically acceptable salt thereof.

In some embodiments, the method of modulating TCR-Nck is used to treat granulomatosis with polyangiitis (Wegener's granulomatosis). (See, e.g., Morgan, M. D. et al., Arthritis & Rheumatism, 2011, 63(7): 2127-37). Accordingly, in some embodiments, the present invention provides a method of treating granulomatosis with polyangiitis (Wegener's granulomatosis), in a patient in need thereof, comprising the step of administering to said patient a provided compound or a pharmaceutically acceptable salt thereof.

In some embodiments, the method of modulating TCR-Nck is used to treat hematological cancer. Accordingly, in some embodiments, the present invention provides a method of treating hematological cancer, in a patient in need thereof, comprising the step of administering to said patient a provided compound or a pharmaceutically acceptable salt thereof.

In some embodiments, the method of modulating TCR-Nck is used to treat transplant rejection. (See, e.g., Issa, F. et al., Expert Rev. Clin. Immunol. 2010, 6(1): 155-69). In some embodiments, the method of modulating TCR-Nck is used to treat graft-versus-host disease. (See, e.g., W. D., Nature Rev. Immunology, 2007, 7: 340-52). Accordingly, in some embodiments, the present invention provides a method of treating a disorder associated with transplantation, in a patient in need thereof, comprising the step of administering to said patient a provided compound or a pharmaceutically acceptable salt thereof.

Combinations

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. As used herein, additional therapeutic agents that are normally administered to treat a particular disease, or condition, are known as "appropriate for the disease, or condition, being treated."

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating a TCR-Nck mediated disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmicort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevirapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmicort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch- Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behçet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behçet's disease, scleroderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T-cell activation, a cardiovascular disorder, and a CNS disorder.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation.

A compound of the current invention may also be used to advantage in combination with antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; antiandrogens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g., in the form as it is marketed, e.g., under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R. P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g., under the trademark Carboplat™. Oxaliplatin can be administered, e.g., in the form as it is marketed, e.g., under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g., BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof, see WO 2008/118802), navitoclax (and analogs thereof, see U.S. Pat. No. 7,390,799), NH-1 (Shenayng Pharmaceutical University), obatoclax (and analogs thereof, see WO 2004/106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO 2008/039218 and WO 2011/090760, the entirety of which are incorporated herein by reference.

Further examples of SYK inhibitory compounds, and conditions treatable by such compounds in combination with compounds of this invention can be found in WO 2003/063794, WO 2005/007623, and WO 2006/078846, the entirety of which are incorporated herein by reference.

Further examples of PI3K inhibitory compounds, and conditions treatable by such compounds in combination with compounds of this invention can be found in WO 2004/019973, WO 2004/089925, WO 2007/016176, U.S. Pat. No. 8,138,347, WO 2002/088112, WO 2007/084786, WO 2007/129161, WO 2006/122806, WO 2005/113554, and WO 2007/044729 the entirety of which are incorporated herein by reference.

Further examples of JAK inhibitory compounds, and conditions treatable by such compounds in combination with compounds of this invention can be found in WO 2009/114512, WO 2008/109943, WO 2007/053452, WO 2000/142246, and WO 2007/070514, the entirety of which are incorporated herein by reference.

Further anti-angiogenic compounds include compounds having another mechanism for their activity, e.g., unrelated to protein or lipid kinase inhibition e.g., thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g., inhibitors of phosphatase 1, phosphatase 2A, or CDC125, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, "Principles of Radiation Therapy", Cancer, in Principles and Practice of Oncology", Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g., Patents International (e.g., IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATIONS

The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

It will be appreciated that, although the general methods depict the synthesis of certain compounds of the present invention, the following general methods, and other methods known to one of ordinary skill in the art, can be applied to all compounds and subclasses and species of each of these compounds, as described herein.

Certain compounds as described herein can also be prepared using the synthetic methods described in prior U.S. patents, for example, U.S. Pat. Nos. 8,614,231, 9,120,764, 10,131,647 and 10,106,518, each of which is incorporated herein by reference in its entirety.

List of Common Abbreviations Used in the Experimental Section

4A MS: 4 Å molecular sieves
AcOH: acetic acid
Anhyd: anhydrous
aq: aqueous
$BH_3$-THF: borane tetrahydrofuran complex
BINAP: (2,2'-bis(diphenylphosphino)-1,1'-binaphthyl)
Bn: benzyl
Boc: tert-butoxycarbonyl
$(Boc)_2O$: di-tert-butyl dicarbonate
BrettPhos: 2-(Dicyclohexylphosphino)3,6-dimethoxy-2', 4',6'-triisopropyl-1,1'-biphenyl
CbzCl: benzyl chloroformate
Cbz-OSU: N-(Benzyloxycarbonyloxy)succinimide
CHIRAL-HPLC: chiral high performance liquid chromatography
CMBP: (cyanomethylene)tributylphosphorane
Conc.: concentrated
CuCN: copper cyanide
d: days
DAST: diethylaminosulfur trifluoride
DavePhos: 2-Dicyclohexylphosphino-2'-(N,N-dimethylamino)biphenyl
dba: dibenzylideneacetone
DBU: 1,8-diazobicyclo[5.4.0]undec-7-ene
DCE: 1,2-dichloroethane
DCM: dichloromethane
DEA: diethylamine
DIBAL-H: diisobutylaluminium hydride
DIPEA: N,N-diisopropylethylamine
DMA: N,N-dimethylacetamide
DMAP: 4-dimethylaminopyridine
DMF: N,N-dimethylformamide
DMPU: 1,3-dimethyl-3,4,5,6-tetrahydro-2-pyrimidinone
DMSO: dimethyl sulfoxide
DPPA: diphenylphosphoryl azide
dppf: 1,1'-bis(diphenylphosphino)ferrocene
EA: ethyl acetate
EDCI: 1-(3-dimethylaminopropyl)-3-ethylcarbodiimide hydrochloride
EDTA: ethylenediaminetetraacetic acid
ee: enantiomeric excess
ESI: electrospray ionization
$Et_3N$: triethylamine
$Et_2O$: diethyl ether
EtOAc: ethyl acetate
EtOH: ethanol
Fmoc: fluorenylmethyloxycarbonyl
Fmoc-OSu: N-(9-fluorenylmethoxycarbonyloxy)succinimide
h: hours
HATU: N,N,N',N'-tetramethyl-O-(7-azabenzotriazol-1-yl)uranium hexafluorophosphate
HOBt: Hydroxybenzotriazole
HPLC: high performance liquid chromatography
HCl: hydrochloric acid
IBX: 2-iodoxybenzoic acid
IPA: isopropyl alcohol
JackiePhos: 2-{Bis[3,5-bis(trifluoromethyl)phenyl]phosphino}-3,6-dimethoxy-2',4',6'-triisopropyl-1,1'-biphenyl, Bis(3,5-bis(trifluoromethyl)phenyl)(2',4',6'-triisopropyl-3,6-dimethoxybiphenyl-2-yl)phosphine
LDA: lithium diisopropylamide
M: molar
mCPBA: meta-chloroperoxybenzoic acid
Me: methyl
MeCN: acetonitrile
MeOH: methanol
MgO: magnesium oxide min: minutes
mL: milliliters
mM: millimolar
mmol: millimoles
MOM: methoxymethyl
MsCl: Mesyl Chloride
MTBE: methyl tert-butyl ether
NMP: N-methyl-2-pyrrolidone
n-BuLi: n-butyl lithium
NBS: N-bromosuccinimide
NIS: N-iodosuccinimide
NMO: 4-methylmorpholine N-oxide
NMP: N-methylpyrrolidine
NMR: Nuclear Magnetic Resonance
° C.: degrees Celsius
PBS: phosphate buffered saline
Pd/C: palladium on carbon
$Pd_2(dba)_3$: tris(dibenzylideneacetone)dipalladium(0)
PE: petroleum ether
prep-HPLC: preparative high performance liquid chromatography
P(o-tol)$_3$: tri(o-tolyl)phosphine
PTFE: polytetrafluoroethylene
Rel: relative
rt: room temperature
RuPhos: 2-dicyclohexylphosphino-2',6'-diisopropoxybiphenyl
sat: saturated
SFC: supercritical fluid chromatography
SGC: silica gel chromatography
STAB: sodium triacetoxyborohydride
TBAB: Tetra-n-butylammonium bromide
TBAF: Tetra-n-butylammonium fluoride
TBSCl: tert-Butyldimethylsilyl chloride
tBuOK: potassium tert-butoxide
tBuONa: sodium tert-butoxide
TEA: triethylamine
TEBAC: Benzyltriethylammonium chloride
Tf: trifluoromethanesulfonate
TfAA: trifluoromethanesulfonic anhydride
TFA: trifluoracetic acid
TIPS: triisopropylsilyl
TLC: thin layer chromatography
THF: tetrahydrofuran
TMSCN: trimethylsilyl cyanide
pTSA: para-toluenesulfonic acid
TsOH: p-Toluenesulfonic acid
XantPhos: 4,5-Bis(diphenylphosphino)-9,9-dimethylxanthene
XPhos: 2-Dicyclohexylphosphino-2',4',6'-triisopropylbiphenyl General Methods of Providing the Present Compounds The preparation of representative non-limiting examples of provided compounds are described below.

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g., fluoride, chloride, bromide, iodide), sulfonates (e.g., mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well-known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenyl-methyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, o-nitrobenzyl, p-nitrobenzyl, p-halobenzyl, 2,6-dichlorobenzyl, p-cyanobenzyl, and 2- and 4-picolyl.

Amino protecting groups are well-known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. (Houben-Weyl 4th Ed. 1952, *Methods of Organic Synthesis*, Thieme, Volume 21). Further, the compounds of the present invention can be produced by organic synthesis methods known to one of ordinary skill in the art as shown in the following examples.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. (See e.g., *March's Advanced Organic Chemistry*, 5$^{th}$ Ed., Ed.: Smith, M. B. and March, J., John Wiley & Sons, New York: 2001). Such interconversions may require one or more of the aforementioned techniques, and certain methods for synthesizing compounds of the invention are described below.

EXAMPLES

Synthetic Scheme 1

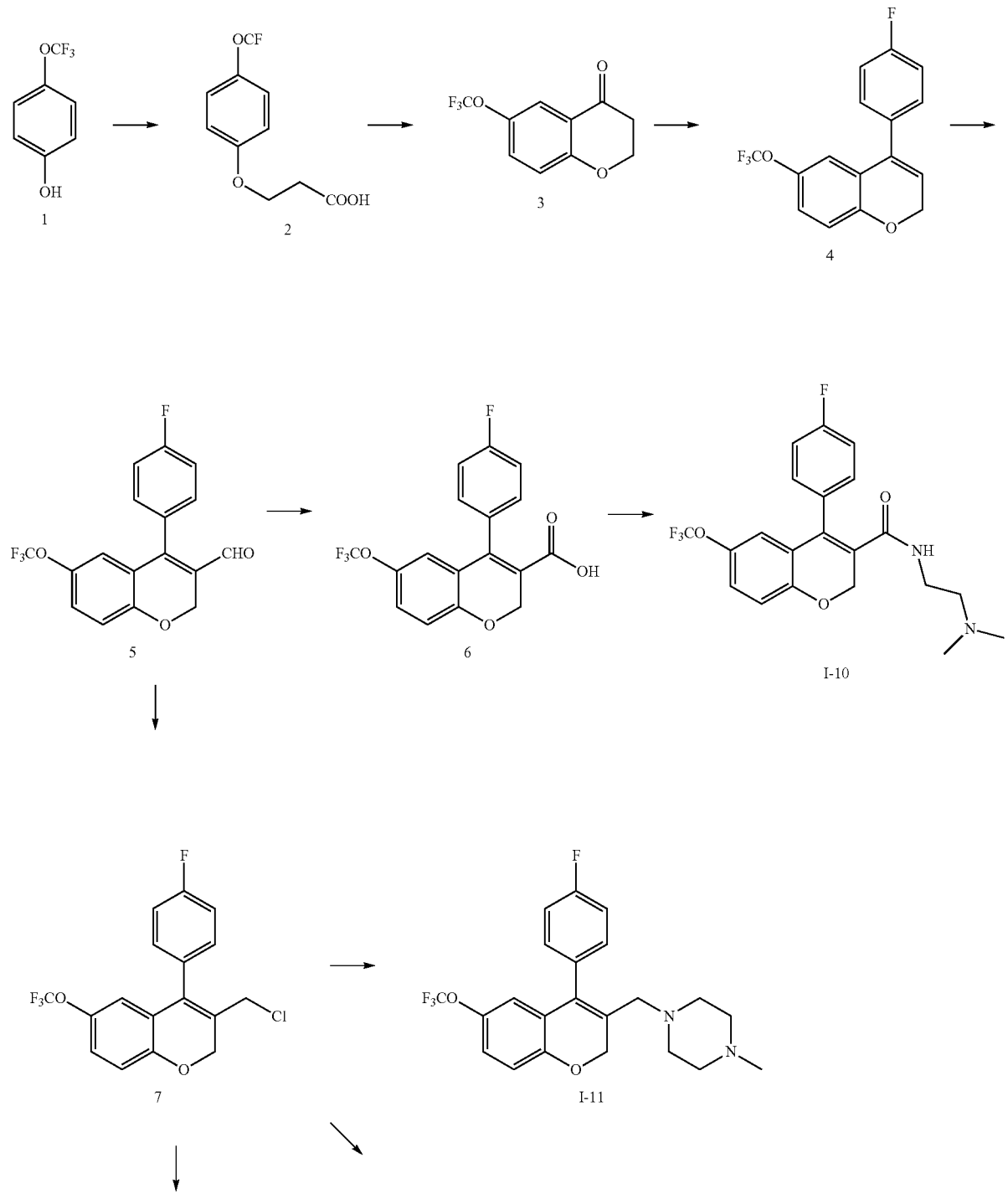

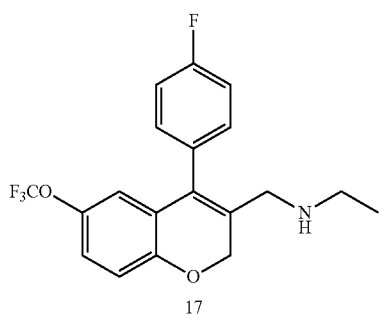

17

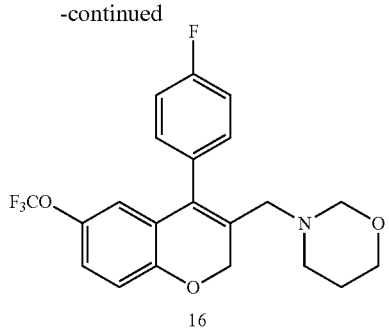

16

Example 1: N-(2-(dimethylamino)ethyl)-4-(4-fluorophenyl)-6-(trifluoromethoxy)-2H-chromene-3-carboxamide

I-10

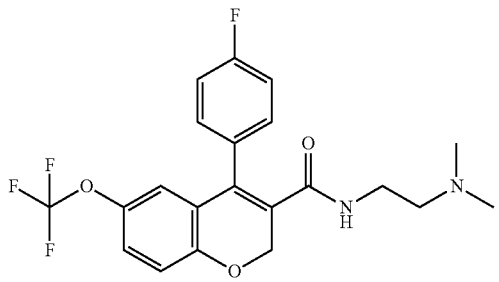

Step 1: Synthesis of 3-(4-(trifluoromethoxy)phenoxy)propanoic acid

Chloropropanonic acid (24.49 g, 224.7 mmol) in 2N NaOH (100 mL) was added drop wise over 10 min at 100° C. to a well-stirred mixture of 4-(trifluoromethoxy)phenol (compound 1; 20 g, 112.35 mmol). The reaction was stirred for 4 h at 100° C. On completion the reaction mixture was cooled to rt and acidified to pH 2-3 using 1N HCl. The resulting solid precipitated was collected by filtration; yielding 4 g of crude compound 2 which was used directly in the next step without any further purification.

Step 2: Synthesis of 6-(trifluoromethoxy)chroman-4-one (Compound 3)

Triflic acid (2.14 mL) was added drop wise over 10 min to a well-stirred mixture of compound 2 (4 g, 16.06 mmol) in TFA (4.56 g, 40.0 mmol) at 0° C. The reaction mixture was stirred for 24 h. On completion the reaction mixture was poured into cold $H_2O$ (100 mL) and extracted with EtOAc (2×150 mL). The combined organic layers were washed with $H_2O$ (100 mL) and brine (100 mL), separated and then dried over anhydrous $Na_2SO_4$. Purification of the crude product by column chromatography (Hexane:EtOAc; 95:5) yielded compound 3 (2.8 g).

Step 3: Synthesis of 4-(4-fluorophenyl)-6-(trifluoromethoxy)-2H-chromene n-BuLi (4.9 mL, 1.6 M in hexane, 8.0 mmol) was added drop wise over 10 min at −78° C. to a well-stirred mixture of 4-fluoro-bromobenzne (1.0 g, 8.0 mmol) in THF (20 mL). The reaction was stirred at −78° C. for 30 min. Compound 3 (4.5 g, 30.4 mmol) was dissolved in THF (20 mL) and added to the reaction drop wise over 10 min at −78° C. The reaction temperature was gradually raised to −50° C. and stirred until the starting material was consumed as monitored by TLC. After 4 h, the reaction temperature was brought to −30° C. On completion aq. $NH_4Cl$ (50 mL) was added to the reaction mixture and extracted with EtOAc (2×150 mL). The combined organic layers were washed with $H_2O$ (100 mL) and brine (100 mL), separated and then dried over anhydrous $Na_2SO_4$. Evaporation of the organic layer under reduced pressure yielding crude product which was used directly in the next step without any purification or analysis. To this crude product 20% aq. $H_2SO_4$ (5 mL) and 1,4-dioxane (5 mL) were added and the reaction was refluxed over 6 h at 95° C., then the contents were washed with NaOH (1%, 20 mL) and extracted with EtOAc (2×100 mL). The combined organic layers were washed with $H_2O$ (100 mL) and brine (100 mL), separated and then dried over anhydrous $Na_2SO_4$. Purification of the crude product by column chromatography (hexane) yielded compound 4 (0.525 g).

Step 5: Synthesis of 4-(4-fluorophenyl)-6-(trifluoromethoxy)-2H-chromene-3-carbaldehyde DMF (368 mg, 5.03 mmol) was added drop wise to $POCl_3$ (770 mg, 5.03 mmol) in a round bottom flask and the contents were heated to 40° C. for 45 min. A solution of compound 4 (520 mg, 1.677 mmol) in DMF (1 mL) was added drop wise to the same reaction flask and the contents were heated to 60° C. for 15 hrs. The reaction mixture was cooled to rt and diluted with sat. aq. $NaHCO_3$ solution (pH~8) and extracted with EtOAc (2×50 mL). The combined organic layers were washed with $H_2O$ (100 mL) and brine (100 mL), separated and then dried over anhydrous $Na_2SO_4$. Purification of the crude product by column chromatography (hexane) yielded compound 5 (0.455 g).

Step 6: Synthesis of 4-(4-fluorophenyl)-6-(trifluoromethoxy)-2H-chromene-3-carboxylic acid $NaH_2PO_4.2H_2O$ (551 mg, 3.99 mmol), $NaClO_2$ (359 mg, 3.99 mmol), and 2-methyl-2-butene (932 mg, 13.3 mmol) were added to a well-stirred solution of compound 5 (450 mg, 1.33 mmol) in t-BuOH (25 mL) followed by water (2 mL) at rt. The reaction was then stirred for 20 min. The reaction was monitored by TLC; on completion the contents were evaporated and the reaction pH was adjusted to 2-3 by adding 2N HCl. The resulting solid product precipitate and was isolated by filtration and dried to yield compound 6 (0.463 g).

Step 7: Synthesis of N-(2-(dimethylamino)ethyl)-4-(4-fluorophenyl)-6-(trifluoromethoxy)-2H-chromene-3-carboxamide (I-10)

HOBt (175 mg, 1.29 mmol) was added to a mixture of compound 6 (460 mg, 1.29 mmol), diamine (138 mg, 1.95 mmol), EDC·HCl (374 mg, 1.95 mmol), and DIPEA (838 mg, 6.49 mmol) in THF (5 mL) at rt. The reaction mixture was then irradiated (p-wave) for 3 min. On completion the contents were poured into cold H$_2$O (20 mL) and extracted with EtOAc (2×30 mL). The combined organic layers were washed with H$_2$O (20 mL) and brine (10 mL), and separated and then dried over anhydrous Na$_2$SO$_4$. Purification of the crude product by Prep HPLC yielded I-10 (31 mg).

Example 2: 1-((4-(4-fluorophenyl)-6-(trifluoromethoxy)-2H-chromen-3-yl)methyl)-4-methylpiperazine

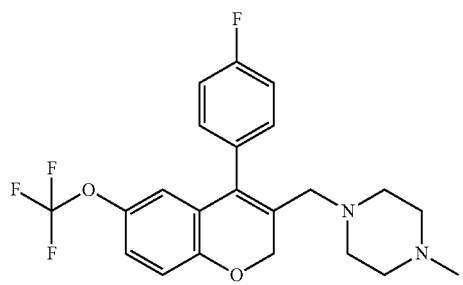

I-11

Step 1: Synthesis of 3-(chloromethyl)-4-(4-fluorophenyl)-6-(trifluoromethoxy)-2H-chromene Sodium borohydride (0.5 eq.) in toluene (20 mL), was added drop wise at rt to a mixture of compound 5 (3 g, 1 eq.) in methanol (2 mL). The reaction was stirred at rt for 2 h. The reaction was monitored by TLC; on completion the reaction mixture was poured into cold water (100 mL) and extracted with ethyl acetate (2×30 mL). The combined organic layers were washed with water (20 mL) and brine solution (10 mL), then dried over anhydrous Na$_2$SO$_4$. Evaporation of the organic layer under reduced pressure yielded 2.7 g of the desired product. This material was used directly in the next step without any purification or analysis. The crude compound (2.7 g) was dissolved in toluene (30 mL). To this mixture, thionyl chloride (1.78 g, 1.4 eq.) was added drop wise at 0° C. and stirred at rt for 2 h. The reaction was monitored by TLC; on completion the reaction mixture was poured into the ice-cold water (25 mL) and extracted with ethyl acetate (2×25 mL). The combined organic layers were washed with water (30 mL) and brine solution (10 mL), and dried over anhydrous Na$_2$SO$_4$. Evaporation of the organic layer under reduced pressure yielded 2.4 g of crude compound 7. This material was used directly in the next step without any purification or analysis.

Step 2: Synthesis of 1-((4-(4-fluorophenyl)-6-(trifluoromethoxy)-2H-chromen-3-yl)methyl)-4-methylpiperazine (I-11)

The mixture of compound 7 (0.2 g, 1 eq.), K$_2$CO$_3$ (0.2 g. 3 eq.), and pyrrolidine (0.05 g, 1.2 eq.) in diisopropyl ether (4 mL) was stirred at rt for 15 h. The reaction was monitored by TLC; on completion the reaction mixture was poured into cold water (20 mL) and extracted with ethyl acetate (2×30 mL). The combined organic layers were washed with water (20 mL) and brine solution (10 mL), and then dried over anhydrous Na$_2$SO$_4$. Purification of the crude product by column chromatography yielded 22 mg of I-11.

Example 3: 4-((4-(4-fluorophenyl)-6-(trifluoromethoxy)-2H-chromen-3-yl)methyl)morpholine

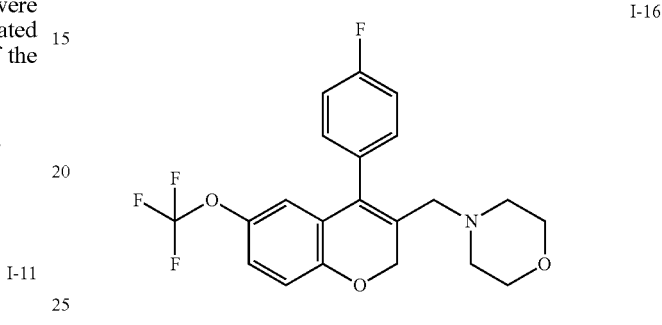

I-16

Synthesis of 4-((4-(4-fluorophenyl)-6-(trifluoromethoxy)-2H-chromen-3-yl)methyl)morpholine (I-16)

The mixture of compound 7 (0.4 g, 1 eq.), K$_2$CO$_3$ (0.5 g. 3 eq.), and morpholine (0.13 g, 1.2 eq.) in diisopropyl ether (4 mL) was stirred at rt for 15 h. The reaction was monitored by TLC; on completion the reaction mixture was poured into cold water (20 mL) and extracted with ethyl acetate (2×30 mL). The combined organic layers were washed with water (20 mL) and brine solution (10 mL), and then dried over anhydrous sodium sulfate. Purification of the crude product by column chromatography yielded 20 mg of I-16.

Example 4: N-((4-(4-fluorophenyl)-6-(trifluoromethoxy)-2H-chromen-3-yl)methyl)ethanamine

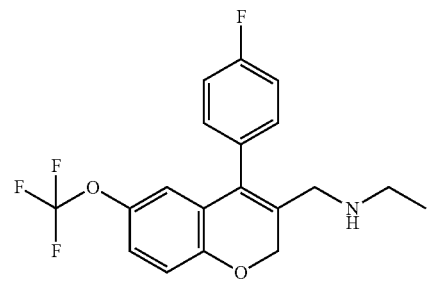

17

Synthesis of N-((4-(4-fluorophenyl)-6-(trifluoromethoxy)-2H-chromen-3-yl)methyl)ethanamine (17)

The mixture of compound 7 (0.4 g, 1 eq.), K$_2$CO$_3$ (0.5 g. 3 eq.) and ethylamine HCl (0.12 g, 1.2 eq.) in diisopropyl ether (4 mL) was stirred at rt for 15 h. The reaction was monitored by TLC; on completion the reaction mixture was poured into cold water (20 mL) and extracted with ethyl acetate (2×30 mL). The combined organic layer was washed with water (20 mL) and brine solution (10 mL), and then dried over anhydrous sodium sulfate. Purification of the crude product by column chromatography yielded 22 mg of 17.
Synthetic Scheme 2
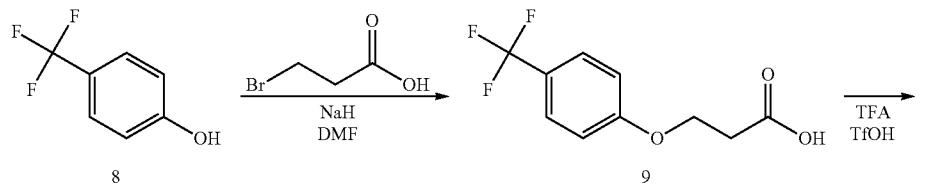
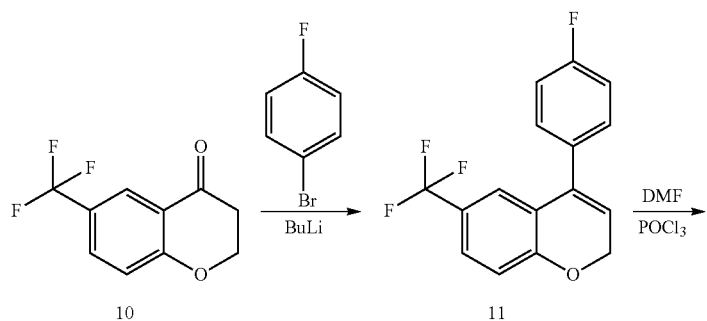
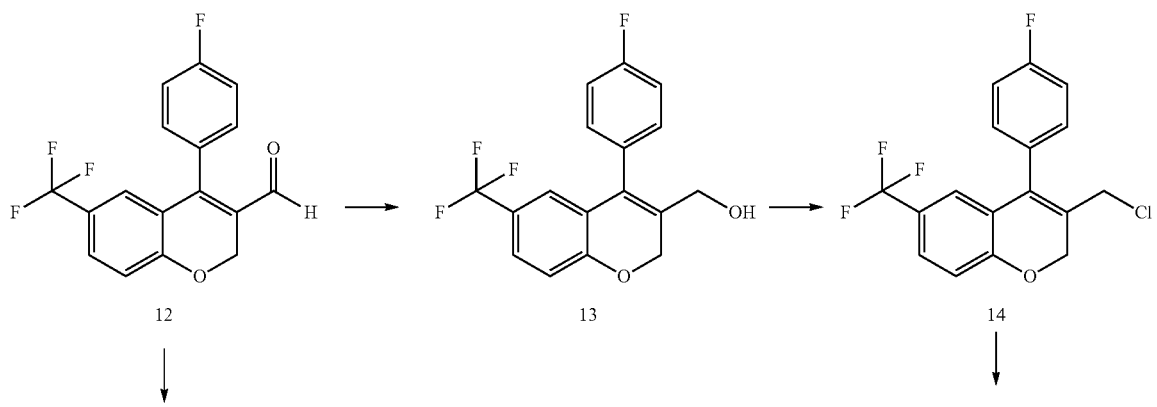
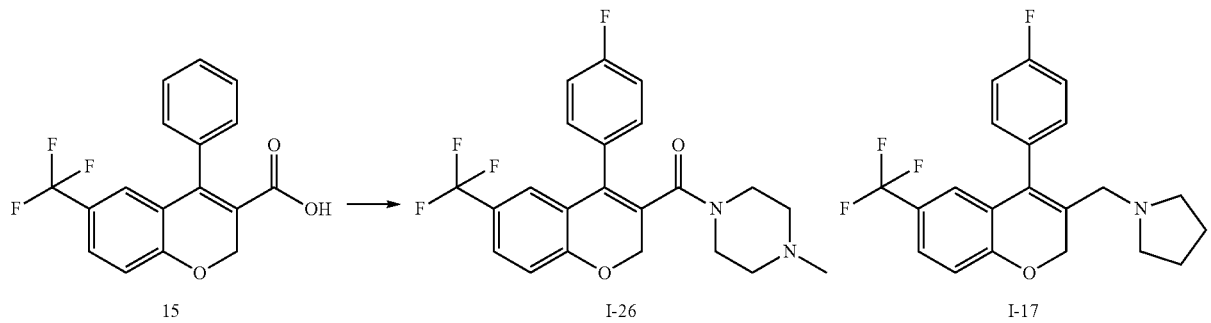

Example 5: 1-((4-(4-fluorophenyl)-6-(trifluoromethyl)-2H-chromen-3-yl)methyl)pyrrolidine

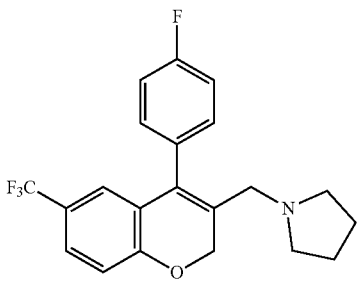

I-17

Step 1: Synthesis of 3-(4-(trifluoromethyl)phenoxy)propanoic acid 3-bromo-propionic acid (7.0 g, 0.046 mol) was added drop wise over 10 min to a well-stirred mixture of compound 8 (5.0 g, 0.033 mol) in DMF (100 mL) at 0° C., then the temperature was allowed to slowly rise to rt. On completion, aq. NH$_4$Cl (200 mL) was added and the reaction mixture was extracted with EtOAc (2×150 mL). The combined organic layers were washed with H$_2$O (100 mL) and brine (100 mL), separated and then dried over anhydrous Na$_2$SO$_4$. Evaporation of the organic layer under reduced pressure yielded 2.9 g of the crude compound 9 which was used directly in the next step without any purification or analysis.

Step 2: Synthesis of 6-(trifluoromethyl)chroman-4-one

Triflic acid (1.64 mL) was added drop wise over 10 min to a well stirred mixture of compound 9 (2.9 g, 0.012 mmol) in TFA (2.38 mL, 0.03 mol) at 0° C. The reaction was stirred at this temperature for 24 h. On completion the contents were poured into cold H$_2$O (100 mL) and extracted with EtOAc (2×100 mL). The combined organic layers were washed with H$_2$O (100 mL) and brine (100 mL), separated and then dried over anhydrous Na$_2$SO$_4$. Purification of the crude product by column chromatography (hexane:EtOAc; 95:5) yielded compound 10 (15 g).

Step 3: Synthesis of 4-(4-fluorophenyl)-6-(trifluoromethyl)-2H-chromene n-BuLi (16.0 mL, 1.6 M in hexane, 6.94 mol) was added drop wise over 10 min to a well-stirred mixture of 3-fluoro-bromobenzne (1.2 g, 6.94 mol) in THF (20 mL) at −78° C. The reaction temperature was allowed to rise slowly to −50° C. and was then stirred for 1 h. Compound 10 (1.5 g, 6.94 mol) was dissolved in THE (20 mL) and added to the reaction at −78° C. drop wise over 10 min and the reaction mixture was allowed to warm to rt and then stirred for 2 h. On completion aq. NH$_4$Cl (200 mL) was added to the reaction mixture followed by extracted with EtOAc (2×150 mL). The combined organic layers were washed with H$_2$O (100 mL) and brine (100 mL), separated and then dried over anhydrous Na$_2$SO$_4$. Evaporation of the organic layer under reduced pressure yielded 2 g of the crude product which was used directly in the next step without any purification or analysis. To this crude product aq. H$_2$SO$_4$ (15 mL, 20%) and 1,4-dioxane (15 mL) were added and the mixture was refluxed for 2 h at 105° C. The contents were then washed with aq. NaOH (20 mL, 1%) and extracted with EtOAc (2×100 mL). The combined organic layers were washed with H$_2$O (100 mL) and brine (100 mL), separated and then dried over anhydrous Na$_2$SO$_4$. Purification of the crude product by column chromatography (hexane:EtOAc; 98:2) yielded compound 11 (1.8 g).

Step 4: Synthesis of 4-(4-fluorophenyl)-6-(trifluoromethyl)-2H-chromene-3-carbaldehyde DMF (1.18 mL, 15.3 mol) and POCl$_3$ (1.14 mL, 12.2 mol) were stirred at 0° C. for 30 min. Then compound 11 (1.8 g, 6.12 mol) in DCM (5 mL) was added to the well-stirred the reaction mixture at 0° C. The reaction mixture was refluxed at 45° C. for 7 h. On completion, the reaction mixture was poured into cold H$_2$O (50 mL) and extracted with EtOAc (2×100 mL). The combined organic layers were washed with sat. sodium bicarbonate solution (100 mL) and brine (100 mL), separated and then dried over anhydrous Na$_2$SO$_4$. Evaporation of the organic layer under reduced pressure gave 2 g of crude 12 which was purified by column chromatography (hexane:EtOAc; 98:2) to yield compound 12 (0.6 g).

Step 5: Synthesis of (4-(4-fluorophenyl)-6-(trifluoromethyl)-2H-chromen-3-yl)methanol Sodium borohydride (52 mg, 1.39 mol) was added portion-wise to a well-stirred mixture of compound 12 (0.3 g, 0.9 mol) in methanol (10 mL) at rt. The reaction was then stirred at rt for 1 h. The reaction was monitored by TLC; on completion the reaction mixture was poured into sat. sodium bicarbonate solution (50 mL) and extracted with ethyl acetate (2×50 mL). The combined organic layers were washed with water (50 mL) and brine solution (20 mL), separated and then dried over Na$_2$SO$_4$. Evaporation of the organic layer under reduced pressure followed by was purification by column chromatography (hexane:EtOAc; 85:15) yielded compound 13 (0.3 g).

Step 6: Synthesis of 3-(chloromethyl)-4-(4-fluorophenyl)-6-(trifluoromethyl)-2H-chromene Compound 13 (0.3 g) was dissolved in toluene (6 mL) and thionyl chloride (0.1 mL, 1.2 mol) was added drop wise at 0° C. The reaction mixture was then stirred at rt for 1 h and monitored by TLC. On completion the mixture was poured into the ice cold water (25 mL) and extracted with EtOAC (2×25 mL). The combined organic layers were washed with water (30 mL) and brine (10 mL), separated and dried over anhydrous Na$_2$SO$_4$. Evaporation of the organic layer under reduced pressure gave (0.3 g) crude 14 which was used directly in the next step without any purification or analysis.

Step 7: Synthesis of 1-((4-(4-fluorophenyl)-6-(trifluoromethyl)-2H-chromen-3-yl)methyl)pyrrolidine (I-17)

A mixture of compound 14 (0.3 g, 0.87 mol), K$_2$CO$_3$ (0.36 g, 2.62 mol), and pyrrolidine (93 mg, 1.31 mol) was stirred in diisopropyl ether (15 mL) at rt. The reaction was monitored by TLC; on completion the mixture was poured into cold water (20 mL) and extracted with EtOAc (2×30 mL). The combined organic layers were washed with water (20 mL) and brine (10 mL), separated and then dried over anhydrous Na$_2$SO$_4$. Purification of the crude product by column chromatography (hexane:EtOAc; 85:15) yielded I-17 (28 mg).

Example 6: (4-(4-fluorophenyl)-6-(trifluoromethyl)-2H-chromen-3-yl)(4-methylpiperazin-1-yl)methanone

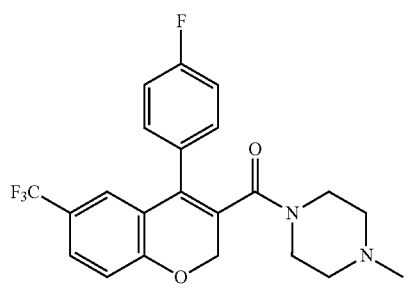
I-26

Step 1: Synthesis of 4-phenyl-6-(trifluoromethyl)-2H-chromene-3-carboxylic acid

Water (0.9 mL) was added drop wise at rt to a well-stirred mixture of compound 12 (0.3 g, 0.96 mol) in t-BuOH (10 mL), 2-Methyl-2-butene (1.08 g, 9.62 mol), sodium chlorite (0.26 g, 2.88 mol), and NaH$_2$PO$_4$·H$_2$O (0.34 g, 2.88 mol) followed by stirring for 1.5 h. The reaction was monitored by TLC; on completion the mixture was evaporated and pH of the mixture was adjusted to 2-3 by adding 2N HCl. The resulting solid product precipitated and was isolated by filtration and dried to yield compound 15 (0.2 g).

Step 2: Synthesis of (4-(4-fluorophenyl)-6-(trifluoromethyl)-2H-chromen-3-yl)(4-methylpiperazin-1-yl)methanone (I-26)

A mixture of compound 15 (0.2 g, 0.59 mol), EDC (0.17 g, 0.88 mol), N-methyl piperzine (89 mg, 0.88 mol), HOBt (90 mg, 0.59 mol), and DIPEA (0.3 mL, 1.77 mol) was stirred in THF (10 mL) at rt. The reaction was monitored by TLC; on completion the mixture was poured on ice and stirred for 30 min. The resulting solid precipitant was filtered and washed with water. Purification of the crude product by column chromatography (DCM:MeOH; 96:4) yielded I-26 (22 mg).

Synthetic Scheme 3

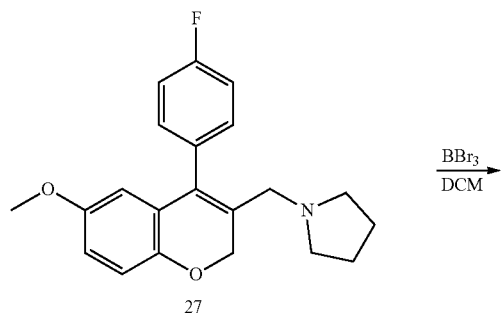

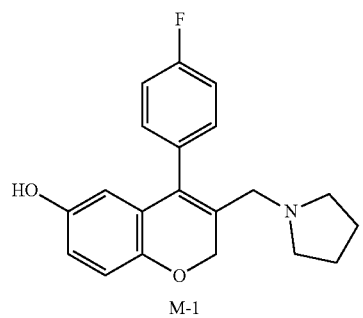
M-1

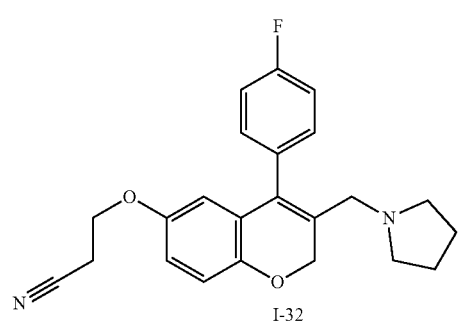
I-32

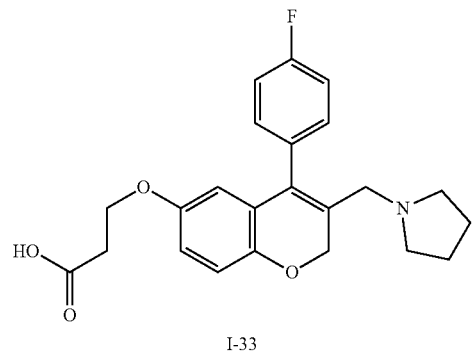
I-33

Example 7: 3-((4-(4-fluorophenyl)-3-(pyrrolidin-1-ylmethyl)-2H-chromen-6-yl)oxy)propanenitrile

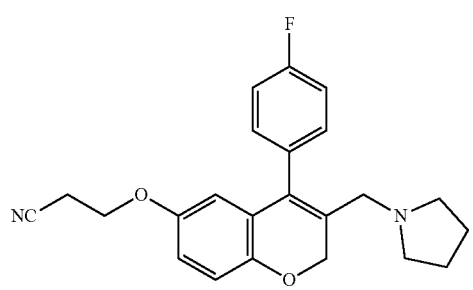
I-32

Step 1: Synthesis of 4-(4-fluorophenyl)-3-(pyrrolidin-1-ylmethyl)-2H-chromen-6-ol BBr₃ (11.4 g, 1.3 eq.) was added drop wise at 0° C. to a solution of 1-((4-(4-fluorophenyl)-6-methoxy-2H-chromen-3-yl)methyl)pyrrolidine 27(10 g, 1 eq.) in dry DCM (150 mL), followed by stirring at rt overnight. The reaction was monitored by TLC; on completion, the reaction mixture was poured into ice cold water and extracted with DCM (2×150 mL). The combined organic layers were washed with water (2×70 mL) and brine solution (20 mL), and dried over Na₂SO₄. Purification of crude product by column chromatography (40% ethyl acetate in hexane) yielded the 4.7 g of M-1.

Step 2: Synthesis of 3-((4-(4-fluorophenyl)-3-(pyrrolidin-1-ylmethyl)-2H-chromen-6-yl)oxy)propanenitrile (I-32)

K₂CO₃ (380 mg, 2.7 mmol) was added to a well-stirred mixture of compound M–1 (0.3 g, 0.92 mmol) in acrylonitrile (1.5 mL) and DMF (1.5 mL). The reaction mixture was refluxed for 24 h at 85° C. On completion the mixture was poured into cold H₂O (200 mL) and extracted with toluene (2×300 mL). The combined organic layers were washed with H₂O (200 mL) and brine (100 mL), separated and then dried over anhydrous Na₂SO₄. Evaporation of the organic layer under reduced pressure yielded 150 mg of crude I-32 which was used directly in the next step without any further purification.

Example 8: 3-((4-(4-fluorophenyl)-3-(pyrrolidin-1-ylmethyl)-2H-chromen-6-yl)oxy)propanoic acid

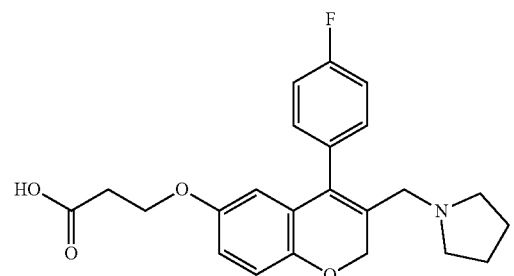

I-33

Synthesis of 3-((4-(4-fluorophenyl)-3-(pyrrolidin-1-ylmethyl)-2H-chromen-6-yl)oxy)propanoic acid (I-33)

A mixture of compound I-32 (150 mg) in conc. HCl (0.75 mL) was refluxed for 1 h at 100° C. On completion the mixture was poured into cold H₂O (200 mL) and the resulting solid precipitate was collected by filtration. Purification by column chromatography yielded I-33 (100 mg).

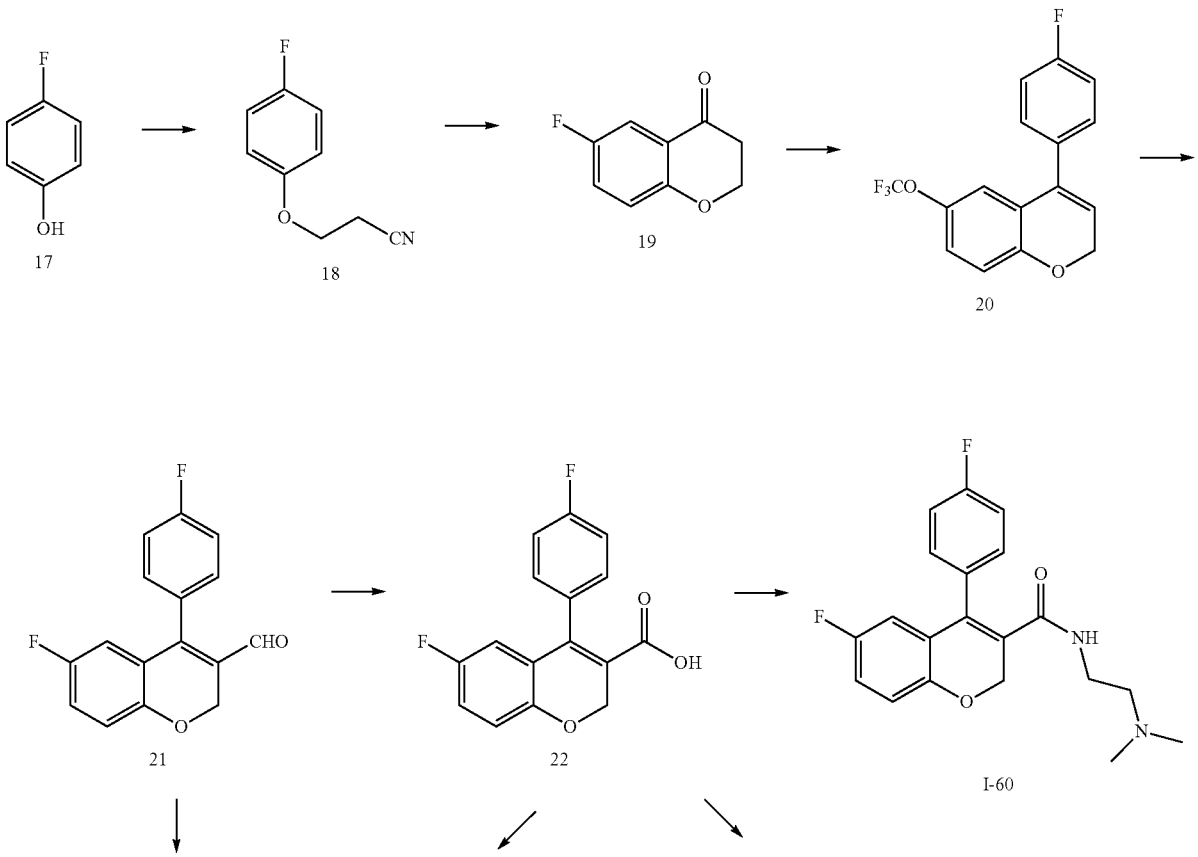

Synthetic Scheme 4

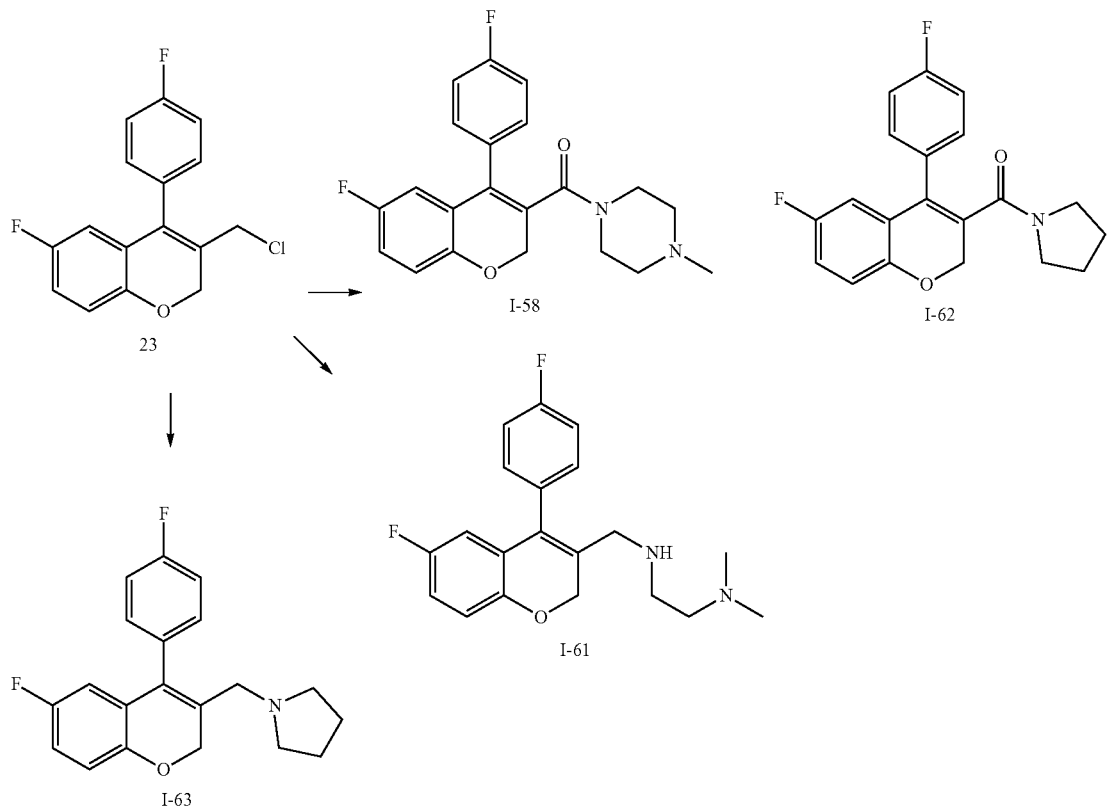

Example 9: 6-fluoro-4-(4-fluorophenyl)-2H-chromen-3-yl)(4-methylpiperazin-1-yl)methanone

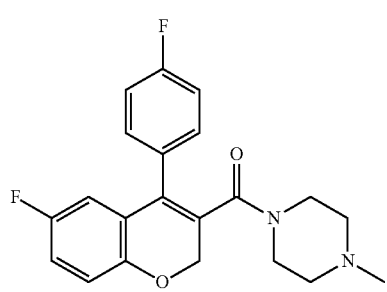

I-58

Step 1: Synthesis of 3-(4-fluorophenoxy)propanenitrile

K₂CO₃ (44.4 g, 322 mmol) was added to a well-stirred mixture of 4-fluorophenol (compound 17; 12 g, 107.1 mmol) in acrylonitrile (120 mL). The reaction was refluxed for 24 h at 85° C. On completion the mixture was poured into cold H₂O (200 mL) and extracted with toluene (2×300 mL). The combined organic layers were washed with H₂O (200 mL) and brine (100 mL), separated and then dried over anhydrous Na₂SO₄. Evaporation of the organic layer under reduced pressure yielded 7.2 g of crude compound 18 which was use directly in the next step without any further purification.

Step 2: Synthesis of 6-fluorochroman-4-one

Triflic acid (5.78 mL) was added drop wise over 10 min to a well-stirred mixture of compound 18 (7.2 g, 43.6 mmol) in TFA (19.89 g, 174.4 mmol) at 0° C. The reaction was stirred for 24 h. On completion the mixture was poured into cold H₂O (100 mL) and extracted with EtOAc (2×150 mL). The combined organic layers were washed with H₂O (100 mL) and brine (100 mL), separated and then dried over anhydrous Na₂SO₄. Purification of the crude product by column chromatography (hexane:EtOAc; 95:5) yielded compound 19 (4.6 g).

Step 3: Synthesis of 4-(4-fluorophenyl)-6-(trifluoromethoxy)-2H-chromene n-BuLi (26 mL, 1.6 M in hexane, 42.0 mmol) was added of over 10 min to a well-stirred mixture of 4-fluoro-bromobenzne (7.3 g, 42.0 mmol) in THF (60 mL) at −78° C. The reaction was stirred at −78° C. for 30 min. Compound 19 (4.6 g, 27.8 mmol) was dissolved in THF (20 mL) and added drop wise over 10 min to the reaction at −78° C., then the reaction temperature was gradually raised to −50° C. The reaction was monitoring by TLC; after the starting material was consumed (4 h) the reaction temperature was raised to −30° C. and on completion aq. NH₄Cl (50 mL) was added and the reaction mixture was then extracted with EtOAc (2×150 mL). The combined organic layers were washed with H₂O (100 mL) and brine (100 mL), separated and then dried over anhydrous Na₂SO₄. Evaporation of the organic layer under reduced pressure yielded the crude product which was used directly in the next step without any purification or analysis. To this crude product aq. H₂SO₄ (20 mL, 20%) and 1,4-dioxane (50 mL) were added and the reaction was refluxed for 6 h at 95° C. The mixture was then washed with aq. NaOH (20 mL, 1%) and extracted with EtOAc (2×100 mL). The combined organic layers were washed with H₂O (100 mL) and brine (100 mL), separated and then dried over anhydrous Na₂SO₄. Purification of the crude product by column chromatography (hexane) yielded compound 20 (3.9 g).

Step 4: Synthesis of 6-fluoro-4-(4-fluorophenyl)-2H-chromene-3-carbaldehyde

DMF (2.92 g, 40.0 mmol) was added drop wise to POCl₃ (4.90 g, 31.92 mmol) in a round bottom flask, then the mixture was heated to 40° C. for 45 min. A solution of compound 20 (3.9 g, 15.98 mmol) in DCM (10 mL) was added drop wise at the same reaction flask and the mixture was heated to 60° C. for 15 hrs. The reaction mixture was cooled to rt, diluted with sat. NaHCO₃ solution (pH~ 8), and extracted with EtOAc (2×50 mL). The combined organic layers were washed with H₂O (100 mL) and brine (100 mL), separated and then dried over anhydrous Na₂SO₄. Purification of the crude product by column chromatography (hexane) yielded compound 21 (1.5 g).

Step 5: Synthesis of 6-fluoro-4-(4-fluorophenyl)-2H-chromene-3-carboxylic acid

NaH₂PO₄.2H₂O (3.97 g, 28.7 mmol), NaClO₂ (2.6 g, 28.7 mmol) and 2-methyl-2-butene (6.72 g, 96.0 mmol), followed by water (2.6 mL) were added to a well-stirred solution of compound 21 (2.6 g, 9.5 mmol) in t-BuOH (52 mL) at rt, followed by stirring for 20 min. The reaction was monitored by TLC; on completion the mixture was evaporated and the pH was adjusted to 2-3 by adding 2N HCl. The resulting solid product precipitate was isolated by filtration and dried to yield compound 22 (1.463 g).

Step 6: Synthesis of (6-fluoro-4-(4-fluorophenyl)-2H-chromen-3-yl)(4-methylpiperazin-1-yl)methanone (I-58)

HOBt (159 mg, 1.04 mmol) was added to a mixture of compound 22 (300 mg, 1.04 mmol), N-methyl piperazine (156 mg, 1.56 mmol), EDC HCl (299 mg, 1.56 mmol), and DIPEA (400 mg, 3.13 mmol) in THF (10 mL) at rt. The reaction mixture was then irradiated (p-wave) for 3 min. On completion the reaction mixture was poured into cold H₂O (20 mL) and extracted with EtOAc (2×30 mL). The combined organic layers were washed with H₂O (20 mL) and brine (10 mL), and separated and then dried over anhydrous Na₂SO₄. Purification of the crude product by column chromatography yielded 25 mg of I-58.

Example 10: 1-((6-fluoro-4-(4-fluorophenyl)-2H-chromen-3-yl)methyl)pyrrolidine

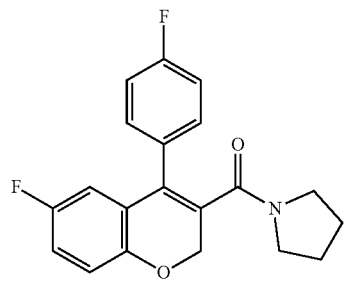

I-62

Synthesis of 1-((6-fluoro-4-(4-fluorophenyl)-2H-chromen-3-yl)methyl)pyrrolidine (I-62)

HOBt (159 mg, 1.04 mmol) was added to a solution mixture of compound 22 (300 mg, 1.04 mmol), pyrrolidine (110 mg, 1.56 mmol), EDC HCl (299 mg, 1.56 mmol), and DIPEA (400 mg, 3.13 mmol) in THF (10 mL) at rt. The reaction mixture was then irradiated (p-wave) for 3 min. On completion the reaction mixture was poured into cold H₂O (20 mL) and extracted with EtOAc (2×30 mL). The combined organic layers were washed with H₂O (20 mL) and brine (10 mL), and separated and then dried over anhydrous Na₂SO₄. Purification of the crude product by column chromatography yielded 28 mg of I-62.

Example 11: $N^1$-((6-fluoro-4-(4-fluorophenyl)-2H-chromen-3-yl)methyl)-$N^2$,$N^2$-dimethylethane-1,2-diamine

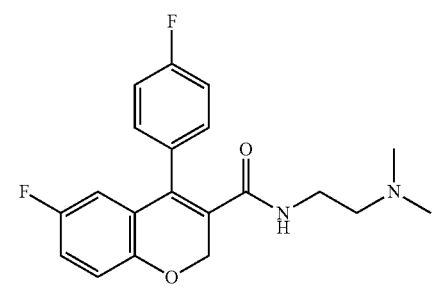

I-60

Synthesis of $N^1$-((6-fluoro-4-(4-fluorophenyl)-2H-chromen-3-yl)methyl)-$N^2$,$N^2$-dimethylethane-1,2-diamine (I-60)

HOBt (159 mg, 1.04 mmol) was added to a solution mixture of compound 22 (300 mg, 1.04 mmol), diamine (140 mg, 1.56 mmol), EDC HCl (299 mg, 1.56 mmol), and DIPEA (400 mg, 3.13 mmol) in THF (10 mL) at rt. The reaction mixture was then irradiated (p-wave) for 3 min. On completion the reaction mixture was poured into cold H₂O (20 mL) and extracted with EtOAc (2×30 mL). The combined organic layers were washed with H₂O (20 mL) and brine (10 mL), and separated and then dried over anhydrous Example 12: 1-((6-fluoro-4-(4-fluorophenyl)-2H-chromen-3-yl)methyl)-4-methylpiperazine

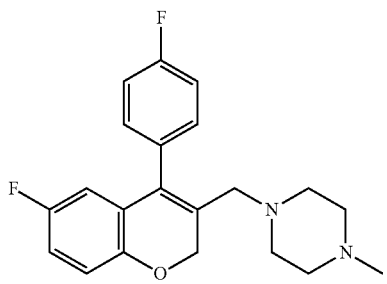

I-59

Step 1: Synthesis of 3-(chloromethyl)-6-fluoro-4-(4-fluorophenyl)-2H-chromene

Methanol (10 mL) added drop wise at rt to a well-stirred mixture of compound 22 (1.5 g, 1 eq.) and sodium borohydride (0.2 g, 1 eq.) in toluene (20 mL). The reaction was stirring at rt for 2 h. The reaction was monitored by TLC; on completion the reaction mixture was poured into cold water (100 mL) and extracted with ethyl acetate (2×30 mL). The combined organic layer was washed with water (20 mL) and brine solution (10 mL), and dried over anhydrous sodium sulfate. Evaporation of the organic layer under reduced pressure yielded 0.6 g of the desired product. This material was used directly in the next step without any purification or analysis. The crude compound (0.6 g) was dissolved in in toluene (6 mL) and thionyl chloride (0.344 g, 1.4 eq.) was added drop wise at 0° C. The reaction was then warmed and stirred at rt for 2 h. The reaction was monitored by TLC; on completion the reaction mixture was poured into ice cold water (25 mL) and extracted with ethyl acetate (2×25 mL). The combined organic layers were washed with water (30 mL) and brine solution (10 mL), and dried over anhydrous $Na_2SO_4$. Evaporation of the organic layer under reduced pressure yielded 1.5 g of crude compound 23. This material was use directly in the next step without any purification or analysis.

Step 2: Synthesis of 1-((6-fluoro-4-(4-fluorophenyl)-2H-chromen-3-yl)methyl)-4-methylpiperazine (I-59)

The mixture of compound 23 (0.3 g, 1 eq.), $K_2CO_3$ (0.43 g. 3 eq.), N-methyl piperazine (0.134 g, 1.3 eq.) in diisopropyl ether (10 mL) was stirred at rt for 15 h. The reaction was monitored by TLC; on completion the reaction mixture was poured into cold water (20 mL) and extracted with ethyl acetate (2×30 mL). The combined organic layers were washed with water (20 mL) and brine solution (10 mL), and dried over anhydrous $Na_2SO_4$. Purification of the crude product by prep TLC purification yielded 25 mg of I-59.

Example 13: 1-((6-fluoro-4-(4-fluorophenyl)-2H-chromen-3-yl)methyl)pyrrolidine

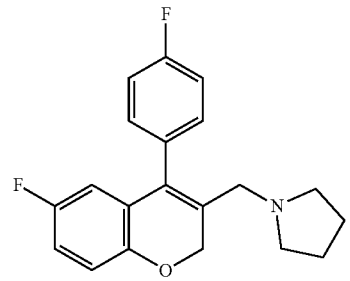

I-63

Synthesis of 1-((6-fluoro-4-(4-fluorophenyl)-2H-chromen-3-yl)methyl)pyrrolidine (I-63)

The mixture of compound 23 (0.3 g, 1 eq.), $K_2CO_3$ (0.43 g. 3 eq.), pyrrolidine (0.09 g, 1.2 eq.) in diisopropyl ether (4 mL) was stirred at rt for 15 h. The reaction was monitored by TLC; on completion the reaction mixture was poured in to cold water (20 mL) and extracted with ethyl acetate (2×30 mL). The combined organic layers were washed with water (20 mL) and brine solution (10 mL), and dried over anhydrous $Na_2SO_4$. Purification of the crude product by column chromatography yielded 28 mg of I-63.

Example 14: $N^1$-((6-fluoro-4-(4-fluorophenyl)-2H-chromen-3-yl)methyl)-$N^2,N^2$-dimethylethane-1,2-diamine

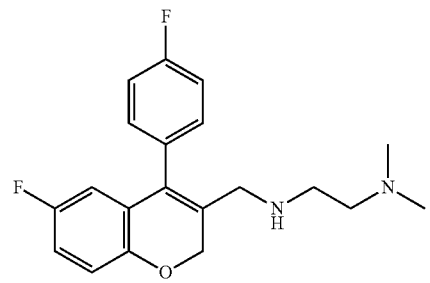

I-61

Synthesis of $N^1$-((6-fluoro-4-(4-fluorophenyl)-2H-chromen-3-yl)methyl)-$N^2,N^2$-dimethylethane-1,2-diamine (I-61)

Sodium borohydride (0.017 g, 0.5 eq.) was added to the mixture of compound 23 (0.25 g, 1 eq.) and ethylamine HCl (0.08 g, 1.2 eq.) in dry MeOH (5 mL) and the mixture was stirred at rt for 0.5 h. The reaction was monitored by TLC; on completion the reaction mixture was poured into cold water (20 mL) and extracted with ethyl acetate (2×30 mL). The combined organic layers were washed with water (20 mL) and brine solution (10 mL), and dried over anhydrous $Na_2SO_4$. Purification of the crude product by prep TLC purification yielded 15 mg of I-61.

Synthetic Scheme 5

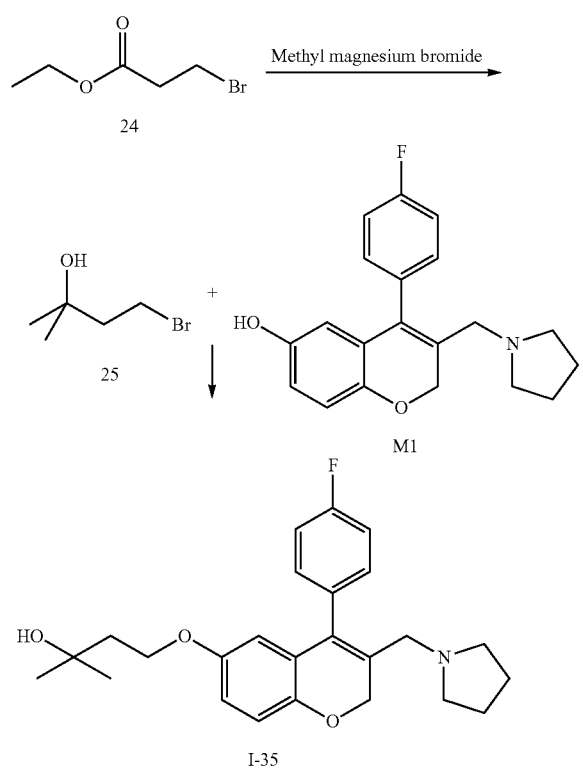

I-35

Example 15: 4-((4-(4-fluorophenyl)-3-(pyrrolidin-1-ylmethyl)-2H-chromen-6-yl)oxy)-2-methylbutan-2-ol

I-35

Step 1: Synthesis of 4-bromo-2-methylbutan-2-ol

Methyl magnesium bromide (11.04 mL, 33.14 mmol) was added drop wise over 10 min to a well-stirred mixture of ethyl 3-bromopropanoate (compound 24; 2.0 g, 11.04 mmol) in diethyl ether (25 mL) at −20° C. The reaction mixture was stirred at rt for over 2 h. On completion the reaction mixture was poured into aq. NH$_4$Cl (25 mL) and extracted with EtOAc (2×25 mL). The combined organic layers were washed with H$_2$O (100 mL) and brine (100 mL), separated and then dried over anhydrous Na$_2$SO$_4$. Evaporated under reduced pressure yielded 2.1 g of crude compound 25 which was used directly in the next step without any further purification.

Step 2: Synthesis of 4-((4-(4-fluorophenyl)-3-(pyrrolidin-1-ylmethyl)-2H-chromen-6-yl)oxy)-2-methylbutan-2-ol (I-35)

Compound 25 (0.24 g, 1.4 mmol) and K$_2$CO$_3$ (44.4 g, 322 mmol) were added to a well-stirred mixture of compound M1 (0.1 g, 0.3 mmol) in acetonitrile (10 mL). The mixture was refluxed for 24 h at 85° C. On completion the reaction mixture were poured into cold H$_2$O (200 mL) and extracted with ethyl acetate (2×20 mL). The combined organic layers were washed with H$_2$O (20 mL) and brine (20 mL), separated and then dried over anhydrous Na$_2$SO$_4$. Purification of the crude product by prep TLC yielded I-35 (20 mg).

Synthetic Scheme 6

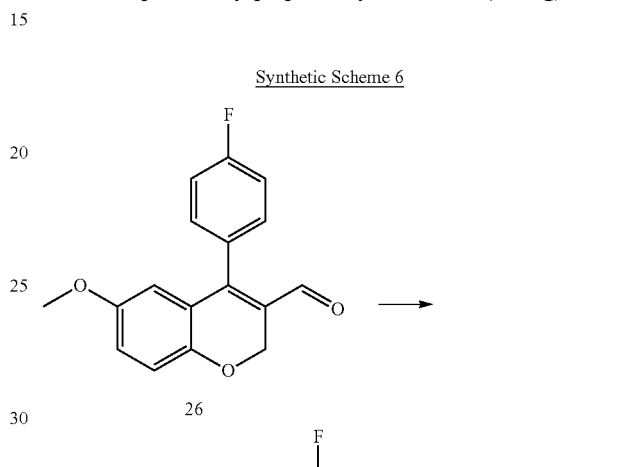

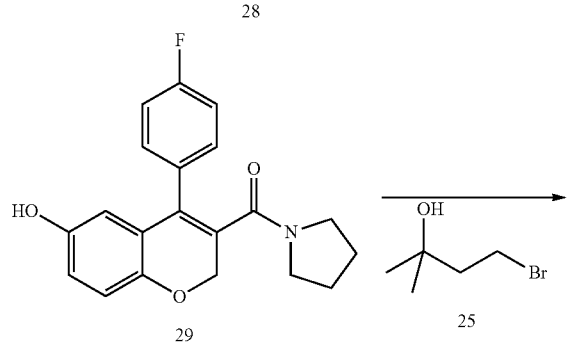

Example 16: (4-(4-fluorophenyl)-6-(3-hydroxy-3-methylbutoxy)-2H-chromen-3-yl)(pyrrolidin-1-yl)methanone

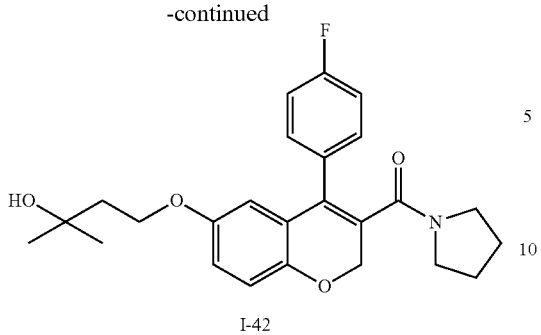

I-42

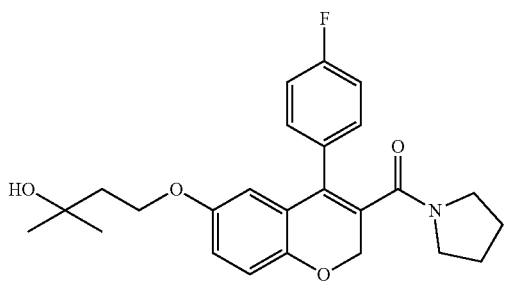

I-42

Step 1: Synthesis of 4-(4-fluorophenyl)-6-hydroxy-2H-chromene-3-carbaldehyde

BBr$_3$ (2.17 g, 1.3 eq.) was added drop wise to the well-stirred solution of 4-(4-fluorophenyl)-6-methoxy-2H-chromene-3-carbaldehyde (compound 26; 5 g, 1 eq.) in dry DCM (50 mL) at 0° C. the reaction was then stirred at rt overnight. The reaction was monitored by TLC; on completion, the reaction mixture was poured into ice cold water and extracted with DCM (2×150 mL). The combined organic layers were washed water (2×70 mL) and brine solution (20 mL), and dried over Na$_2$SO$_4$. Purification of crude product by column chromatography (40% ethyl acetate in hexane) yielded the 1.6 g of compound 27.

Step 2: Synthesis of 4-(4-fluorophenyl)-6-hydroxy-2H-chromene-3-carboxylic acid

NaH$_2$PO$_4$.2H$_2$O (2.44 g, 17.7 mmol), NaClO$_2$ (1.6 g, 17.7 mmol) and 2-methyl-2-butene (6.25 mL, 59.0 mmol) were added to a well-stirred solution of compound 27 (1.6 g, 5.9 mmol) in t-BuOH (15 mL) at rt, followed by water (1.6 mL). The reaction was stirred at rt for 20 min and monitored by TLC. On completion the reaction mixture was evaporated and the pH was adjusted to 2-3 by adding 2N HCl. The resulting solid product precipitate was isolated by filtration and dried to yield compound 28 (670 mg).

Step 3: Synthesis of (4-(4-fluorophenyl)-6-hydroxy-2H-chromen-3-yl)(pyrrolidin-1-yl)methanone HOBt (358 mg, 2.34 mmol) was added to a solution mixture of compound 28 (670 mg, 2.34 mmol), pyrrolidene (240 mg, 3.56 mmol), EDC HCl (673 mg, 3.56 mmol), and DIPEA (1.2 mL, 7.0 mmol) in THF (10 mL) at rt. The reaction mixture was then irradiated (p-wave) for 3 min. On completion the mixture was poured into cold H$_2$O (20 mL) and extracted with EtOAc (2×30 mL). The combined organic layers were washed with H$_2$O (20 mL) and brine (10 mL), separated and then dried over anhydrous Na$_2$SO$_4$. Purification of the crude product yielded compound 29 (200 mg).

Step 4: Synthesis of (4-(4-fluorophenyl)-6-(3-hydroxy-3-methylbutoxy)-2H-chromen-3-yl)(pyrrolidin-1-yl)methanone (I-42)

Compound 25 (0.39 g, 2.3 mmol) and K$_2$CO$_3$ (0.1 g, 0.76 mmol) were added to a well-stirred mixture of compound 29 (0.2 g, 0.58 mmol) in acetonitrile (10 mL). The reaction was refluxed for 24 h at 85° C. On completion the mixture was poured into cold H$_2$O (200 mL) and extracted with ethyl acetate (2×20 mL). The combined organic layers were washed with H$_2$O (20 mL) and brine (20 mL), separated and then dried over anhydrous Na$_2$SO$_4$. Purification of the crude product by column chromatography yielded I-42 (25 mg).

Synthetic Scheme 7

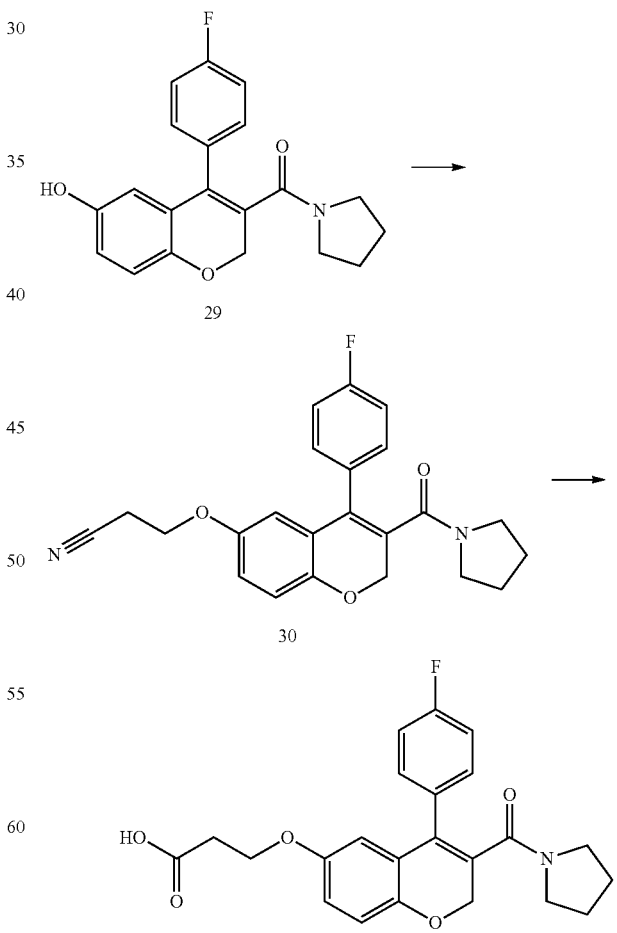

Example 17: 3-((4-(4-fluorophenyl)-3-(pyrrolidine-1-carbonyl)-2H-chromen-6-yl)oxy)propanoic acid

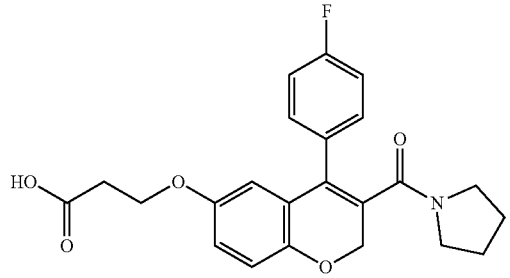

I-40

Step 1: Synthesis of 3-((4-(4-fluorophenyl)-3-(pyrrolidine-1-carbonyl)-2H-chromen-6-yl)oxy)propanenitrile $K_2CO_3$ (0.24 g, 2.94 mmol) was added to a well-stirred mixture of (4-(4-fluorophenyl)-6-hydroxy-2H-chromen-3-yl)(pyrrolidin-1-yl)methanone (compound 29; 0.2 g, 0.58 mmol) in acrylonitrile (5 mL). The reaction was refluxed for 24 h at 85° C. On completion the mixture was poured into cold $H_2O$ (200 mL) and extracted with ethyl acetate (2×25 mL). The combined organic layers were washed with $H_2O$ (20 mL) and brine (20 mL), separated and then dried over anhydrous $Na_2SO_4$. Purification of the crude product by column chromatography (Hexane:EtOAc; 50:50) yielded compound 30 (0.1 g).

Step 2: Synthesis of 3-((4-(4-fluorophenyl)-3-(pyrrolidine-1-carbonyl)-2H-chromen-6-yl)oxy)propanoic acid (I-40)

The mixture of compound 29 (0.1 g) in conc. HCl (0.5 mL) was refluxed for 1 h at 100° C. On completion the mixture was poured into cold $H_2O$ (200 mL) and the resulting solid precipitate was collected by filtration. Further purification by column chromatography yielded I-40 (25 mg).

Synthetic Scheme 8

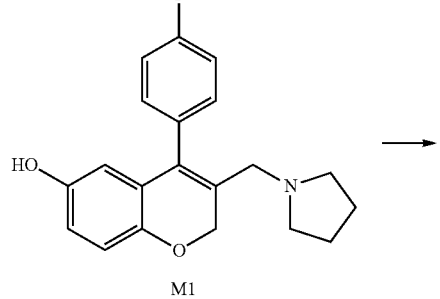

M1

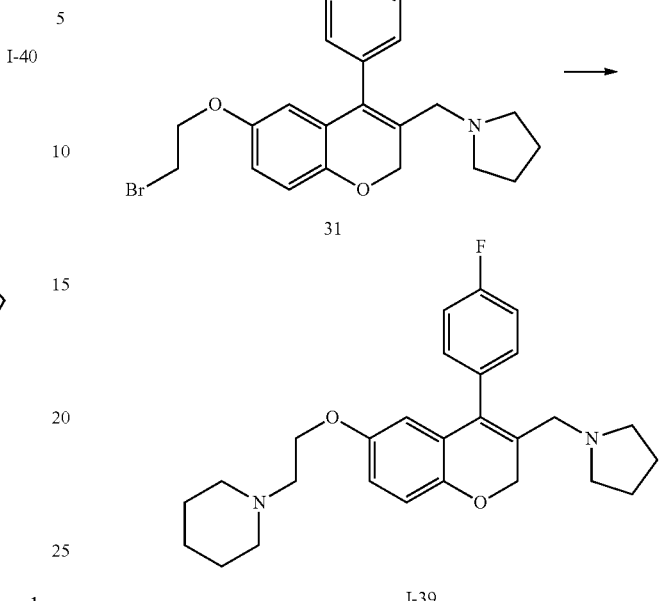

31

I-39

Example 18: 1-(2-((4-(4-fluorophenyl)-3-(pyrrolidin-1-ylmethyl)-2H-chromen-6-yl)oxy)ethyl)piperidine

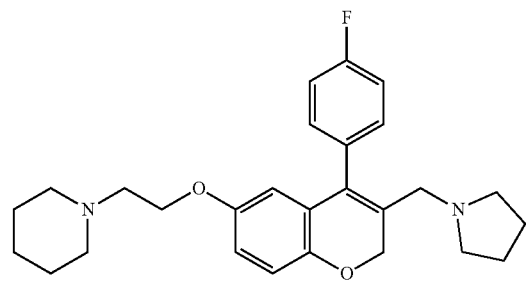

I-39

Step 1: Synthesis of 1-((6-(2-bromoethoxy)-4-(4-fluorophenyl)-2H-chromen-3-yl)methyl)pyrrolidine $Na_2CO_3$ (4.78 g, 45.2 mmol) was added to a well-stirred mixture of compound M1 (2.45 g, 9.04 mmol) and dibromo ethane (0.93 mL, 10.8 mmol) in THF (20 mL). The reaction was refluxed for 24 h at 65° C. On completion the reaction mixture was poured into cold $H_2O$ (200 mL) and extracted with ethyl acetate (2×25 mL). The combined organic layers were washed with $H_2O$ (20 mL) and brine (20 mL), separated and then dried over anhydrous $Na_2SO_4$. Purification of the crude product by column chromatography (hexane:EtOAc; 40:60) yielded compound 31 (0.5 g).

Step 2: Synthesis of 1-(2-((4-(4-fluorophenyl)-3-(pyrrolidin-1-ylmethyl)-2H-chromen-6-yl)oxy)ethyl)piperidine (I-39)

$K_2CO_3$ (0.75 g, 0.55 mmol) was added to a well-stirred mixture of compound 31 (0.16 g, 0.42 mmol) and piperidine (0.16 mL, 1.69 mmol) in acetonitrile (10 mL) The reaction was refluxed for 24 h at 85° C. On completion the reaction mixture was poured into cold H₂O (200 mL) and extracted with ethyl acetate (2×25 mL). The combined organic layers were washed with H₂O (20 mL) and brine (20 mL), separated and then dried over anhydrous Na₂SO₄. Purification of the crude product by prep TLC yielded compound I-39 (18 mg).

mmol) in DMF (10 mL). The reaction was heated for 5 h at 120° C. On completion the reaction mixture was poured into cold H₂O (200 mL) and extracted with ethyl acetate (2×25 mL). The combined organic layers were washed with H₂O (20 mL) and brine (20 mL), separated and then dried over anhydrous Na₂SO₄. Purification of the crude product by prep HPLC yielded compound I-34 (15 mg).

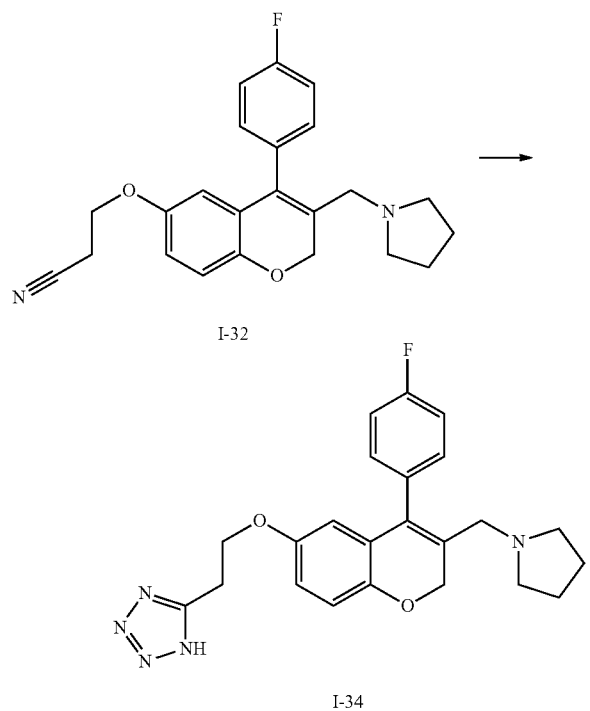

Example 19: 5-(2-((4-(4-fluorophenyl)-3-(pyrrolidin-1-ylmethyl)-2H-chromen-6-yl)oxy)ethyl)-1H-tetrazole Synthesis of 5-(2-((4-(4-fluorophenyl)-3-(pyrrolidin-1-ylmethyl)-2H-chromen-6-yl)oxy)ethyl)-1H-tetrazole (I-34)

A catalytic amount of CuI was added to a well-stirred mixture of I-32 (0.1 g, 0.26 mmol) and NaN₃ (0.13 g, 0.52

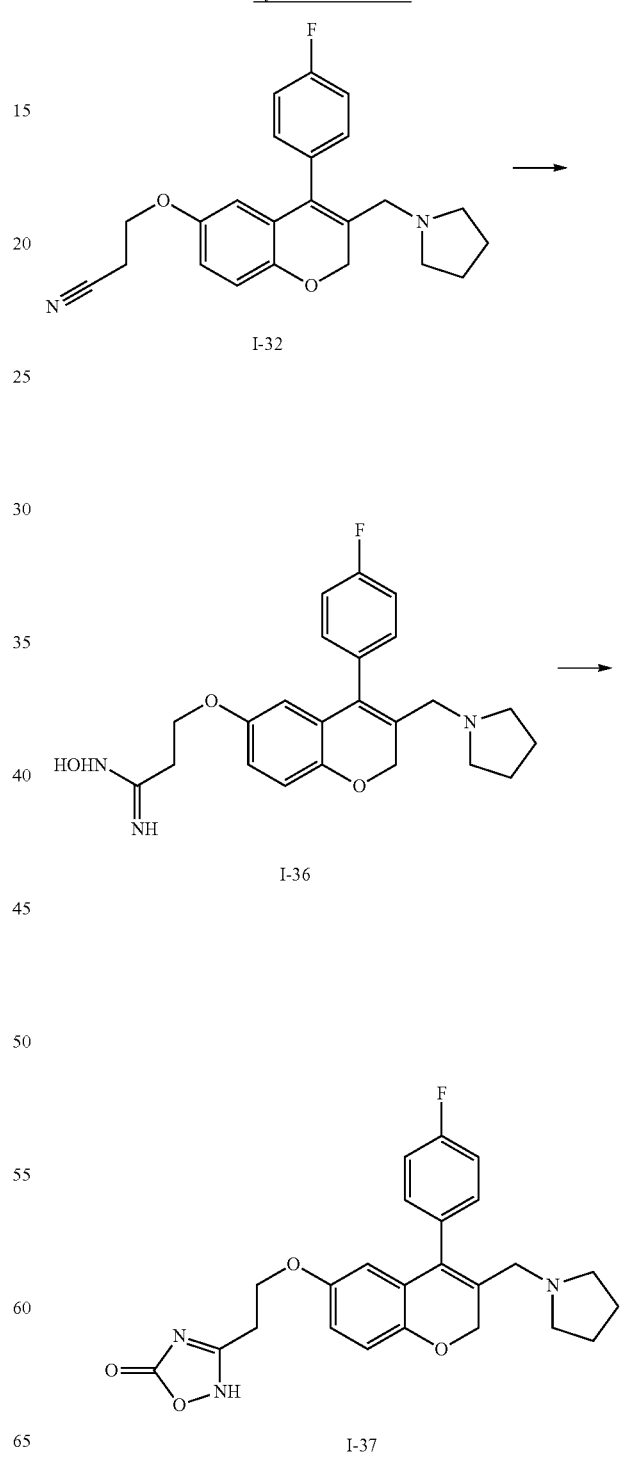

Example 20: 3-((4-(4-fluorophenyl)-3-(pyrrolidin-1-ylmethyl)-2H-chromen-6-yl)oxy)-N-hydroxypropanimidamide

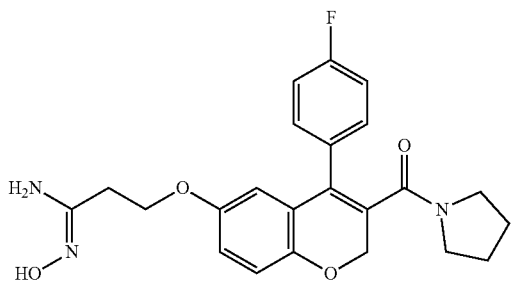

I-36

Synthesis of 3-((4-(4-fluorophenyl)-3-(pyrrolidin-1-ylmethyl)-2H-chromen-6-yl)oxy)-N-hydroxypropanimidamide (I-36)

A solution of I-32 (300 mg, 0.79 mmol), hydroxylamine hydrochloride (110 mg 1.58 mmol), and sodium carbonate (84 mg 0.79 mmol) in ethanol (5 mL) and water (1 mL) was refluxed overnight. The reaction mixture was evaporated under reduced pressure to completely remove ethanol. The product was collected by filtration and air dried to give I-36 (100 mg).

Example 21: 3-(2-((4-(4-fluorophenyl)-3-(pyrrolidin-1-ylmethyl)-2H-chromen-6-yl)oxy)ethyl)-1,2,4-oxadiazol-5(2H)-one

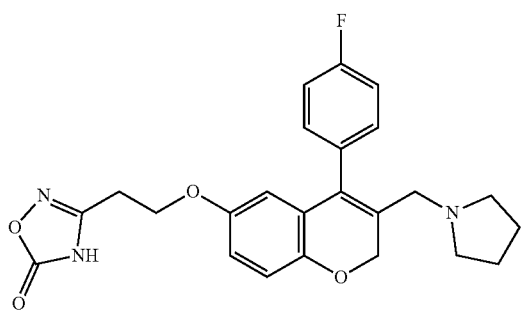

I-37

Synthesis of 3-(2-((4-(4-fluorophenyl)-3-(pyrrolidin-1-ylmethyl)-2H-chromen-6-yl)oxy)ethyl)-1,2,4-oxadiazol-5(2H)-one (I-37)

A solution of I-36 (100 mg, 0.24 mmol) and carbonyldiimidazole (47 mg, 0.29 mmol) in THF (5 mL) was refluxed for 4 hrs. The solvent was removed and the residue was purified by prep TLC to yield compound I-37 (20 mg).

Example 22: Microsomal Stability Assay

Microsomal stability assays were performed using mouse, rat, and human cell lines according to methods well-known in the art. Microsomal stability results are shown in Table 2 for selected compounds of the invention. The compound numbers correspond to the compound numbers in Table 1. Compounds having a designation of "A" provide a half-life of greater than thirty (>30) minutes; compounds having a designation as "B" provide a half-life of between ten (10) and thirty (30) minutes; and compounds having a designation as "C" provide a half-life of less than ten (<10) minutes. "N/A" indicates not assayed.

TABLE 2

| | Microsomal Stability | | |
|---|---|---|---|
| Compound # | Microsomal Stability ($T_{1/2}$ min) Mouse | Microsomal Stability ($T_{1/2}$ min) Rat | Microsomal Stability ($T_{1/2}$ min) Human |
| I-1 | C | C | C |
| I-2 | C | C | B |
| I-3 | C | C | B |
| I-4 | B | B | A |
| I-5 | B | B | B |
| I-6 | A | C | A |
| I-7 | C | C | B |
| I-8 | C | C | A |
| I-9 | B | C | B |
| I-10 | A | A | A |
| I-11 | A | A | A |
| I-12 | A | A | B |
| I-13 | C | C | B |
| I-14 | C | C | B |
| I-15 | C | C | B |
| I-16 | B | C | A |
| I-17 | A | B | A |
| I-18 | N/A | N/A | N/A |
| I-19 | C | C | B |
| I-20 | C | C | B |
| I-21 | C | C | B |
| I-22 | C | C | B |
| I-23 | C | B | B |
| I-24 | C | C | C |
| I-25 | C | C | B |
| I-26 | C | C | B |
| I-27 | C | C | C |
| I-28 | C | C | C |
| I-29 | C | B | C |
| I-30 | C | B | A |
| I-31 | C | C | B |
| I-32 | B | C | B |
| I-33 | A | A | A |
| I-34 | A | A | A |
| I-35 | B | C | A |
| I-36 | B | B | A |
| I-37 | A | B | A |
| I-38 | N/A | N/A | N/A |
| I-39 | A | A | A |
| I-40 | A | A | A |
| I-41 | A | A | C |
| I-42 | C | B | C |
| I-43 | C | A | C |
| I-44 | C | C | C |
| I-45 | N/A | N/A | N/A |
| I-46 | N/A | N/A | N/A |
| I-47 | N/A | N/A | N/A |
| I-48 | N/A | N/A | N/A |
| I-49 | N/A | N/A | N/A |
| I-50 | N/A | N/A | N/A |
| I-51 | N/A | N/A | N/A |
| I-52 | N/A | N/A | N/A |
| I-53 | N/A | N/A | N/A |
| I-54 | N/A | N/A | N/A |
| I-55 | N/A | N/A | N/A |
| I-56 | N/A | N/A | N/A |
| I-57 | N/A | N/A | N/A |
| I-58 | C | C | A |
| I-59 | B | C | A |
| I-60 | N/A | N/A | N/A |
| I-61 | C | C | B |

TABLE 2-continued

Microsomal Stability

| Compound # | Microsomal Stability ($T_{1/2}$ min) Mouse | Microsomal Stability ($T_{1/2}$ min) Rat | Microsomal Stability ($T_{1/2}$ min) Human |
|---|---|---|---|
| I-62 | N/A | N/A | N/A |
| I-63 | B | C | A |

Example 23: Competitive Binding

Inhibition of Nck SH3 domain interaction with the proline rich sequence of TCR subunit CD3ε was measured by optical read-out of a biosensor based on the Interferometric Optical Detection Method (IODM), using established methods (WO 2010/026269; WO 2014/020159; Laguna, M. et al., Sensors, 2015, 15(8):19819-29; and Holgado, M. et al., Sensors, 2014, 14(2): 3675-89).

Briefly, a Biophotonic Cell (BICELL) based on Fabry-Perot interferometers was used as the photonic transducer. The BICELL was fabricated using SU8 in cyclopentanone according to known methods (e.g., Laguna, M. F. et al., Sensors, 2014, 14(4): 6695-6700). Cured film was then treated with 95% sulfuric acid for 10 seconds. Streptavidin was then immobilized on the sensing surface in phosphate buffered saline (PBS; pH 7.4) over 20 min at 37° C. followed by blocking of the surface with 5% skin milk in PBS (pH 7.4). Biotinylated CD3ε peptide (SEQ ID NO: 001) in PBS (pH 7.4) was incubated with the streptavidin coated film to biofunctionalize the sensing surface (20 min at 37° C.).

Competitive binding assays were performed to determine the affinity reaction of inhibitors. The screening was carried out using a ratio of 1:1 between Nck SH3 domain and inhibitors. The optical readout of the biosensor was accomplished by a Fourier transform visible-infrared (FT-VIS-IR) spectrometer. Competitive binding results are shown in Table 3 for selected compounds of the invention. The compound numbers correspond to the compound numbers in Table 1. Compounds having a designation of "A" provide an Increased Relative Optical Power (ΔIROP) of less than or equal to thirty percent (≤30%); compounds having a designation of "B" provide a ΔIROP of between thirty and fifty percent (>30% to ≤50%); compounds having a designation of "C" provide an ΔIROP of between fifty and seventy percent (>50% to ≤70%); and compounds having a designation of "D" provide a ΔIROP of greater than seventy percent (>70%).

TABLE 3

Competitive Binding

| Compound # | ΔIROP |
|---|---|
| I-1 | C |
| I-2 | C |
| I-3 | B |
| I-4 | B |
| I-5 | B |
| I-6 | C |
| I-8 | B |
| I-9 | D |
| I-10 | A |
| I-12 | C |
| I-13 | A |
| I-14 | C |
| I-15 | C |
| I-16 | B |
| I-17 | C |
| I-19 | C |
| I-20 | B |
| I-21 | C |
| I-22 | B |
| I-23 | A |
| I-24 | C |
| I-25 | B |
| I-26 | C |
| I-28 | D |
| I-29 | B |
| I-30 | C |
| I-31 | C |
| I-32 | B |
| I-33 | A |
| I-40 | D |
| I-44 | D |

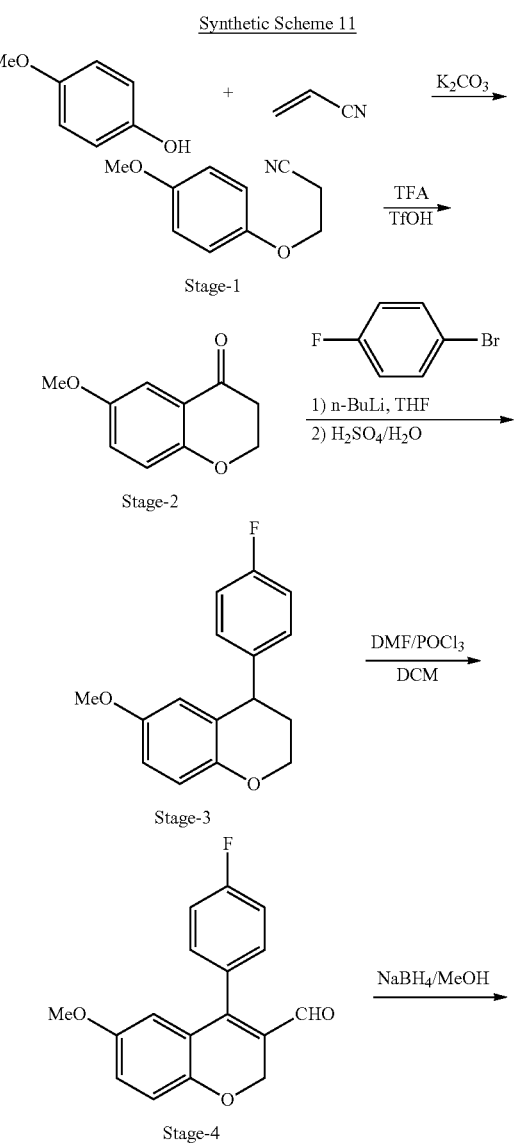

Synthetic Scheme 11

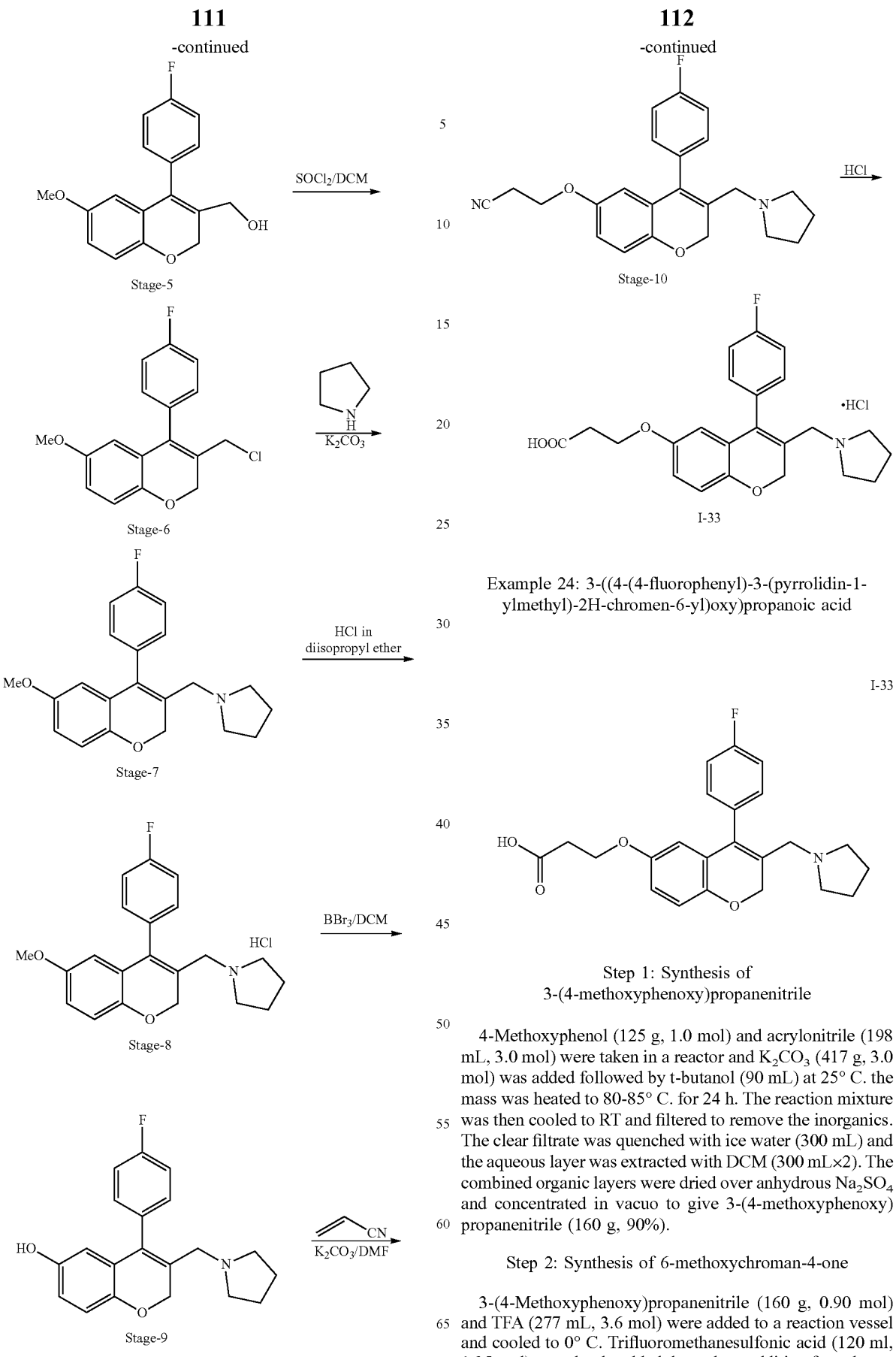

Example 24: 3-((4-(4-fluorophenyl)-3-(pyrrolidin-1-ylmethyl)-2H-chromen-6-yl)oxy)propanoic acid Step 1: Synthesis of 3-(4-methoxyphenoxy)propanenitrile 4-Methoxyphenol (125 g, 1.0 mol) and acrylonitrile (198 mL, 3.0 mol) were taken in a reactor and $K_2CO_3$ (417 g, 3.0 mol) was added followed by t-butanol (90 mL) at 25° C. the mass was heated to 80-85° C. for 24 h. The reaction mixture was then cooled to RT and filtered to remove the inorganics. The clear filtrate was quenched with ice water (300 mL) and the aqueous layer was extracted with DCM (300 mL×2). The combined organic layers were dried over anhydrous $Na_2SO_4$ and concentrated in vacuo to give 3-(4-methoxyphenoxy)propanenitrile (160 g, 90%).

Step 2: Synthesis of 6-methoxychroman-4-one 3-(4-Methoxyphenoxy)propanenitrile (160 g, 0.90 mol) and TFA (277 mL, 3.6 mol) were added to a reaction vessel and cooled to 0° C. Trifluoromethanesulfonic acid (120 ml, 1.35 mol) was slowly added through an addition funnel over a period of 20-30 min. After completion of addition, the reaction was stirred at 25-30° C. for 22-24 h. The reaction was then quenched with water (480 ml). The resulting mixture was extracted with EtOAc (500 mL×2). The combined organic layers were washed with brine, dried over anhydrous $Na_2SO_4$ and concentrated in vacuo to obtain brown colored gummy mass of 6-methoxy-4-chromanone. Diisopropylether (800 mL) was added to the gummy mass of 6-methoxy-4-chromanone and stirred for 5-10 min. The mixture was cooled to 0° C. and stirred for 30 min. The reaction mixture was then filtered with a bucker funnel to separate the pale yellow solid. The compound was dried under vacuum at 25-30° C. to generate 6-methoxychroman-4-one (120 g, 75%).

Step 3: Synthesis of
4-(4-fluorophenyl)-6-methoxy-2H-chromene

A reaction vessel was charged with 1-Bromo-4-fluorobenzene (153 mL) and THF (1.125 L) and cooled to −78° C. to −70° C. Bu-Li in hexane (1.6M; 1.0 L) was added drop-wise to the reaction at −78° C. to −70° C. through an addition funnel over a period of 15-20 min. 6-methoxychroman-4-one (225 g, 1.26 mol) dissolved in THE (1.125 L) was added drop-wise to the reaction at −78° C. to −70° C. through an addition funnel over a period of 15-20 min and the reaction was stirred for 2 h at the same temperature. After completion of the reaction, 10% $NH_4Cl$ solution was added to the reaction at −78° C. to −70° C. and the reaction mixture was gradually warmed to RT. The reaction mixture was extracted with ethyl acetate (1.125 L) and the combined organics were dried over anhydrous $Na_2SO_4$. The solvent was distilled off distilled off to yield a gummy mass of 4-(4-fluoro phenyl)-6-methoxy chroman-4-ol. The crude alcohol was dissolved in 1,4-dioxane and 20% $H_2SO_4$ solution (1.125 L) was added. The mixture was heated to reflux and maintained for 1 h. After completion of the reaction, the reaction was cooled to RT and extracted with ethyl acetate (1.125 L). The organic phase was dried over anhydrous $Na_2SO_4$ and the solvent distilled off completely to yield brown colored gummy mass of crude 4-(4-fluorophenyl)-6-methoxy-2H-chromene. Methanol (500 mL) was added to the crude mass of 4-(4-fluorophenyl)-6-methoxy-2H-chromene and cooled to 0° C. The precipitated solids were filtered to get pure 4-(4-fluorophenyl)-6-methoxy-2H-chromene (160 g, 49%).

Step 4: Synthesis of 4-(4-fluorophenyl)-6-methoxy-2H-chromene-3-carbaldehyde

DMF (75 mL) was added to a reactor and cooled to 0° C. $POCl_3$ (73 mL) was added slowly while maintaining the temperature between 0-5° C. and stirred for 30 min. 4-(4-Fluorophenyl)-6-methoxy-2H-chromene (100 g, 0.39 mol) in DCM (250 mL) was added dropwise at 0-10° C. The reaction was allowed to warm to RT and then heated to 45° C. for 7 h. On completion, reaction was cooled to 20-25° C. and then poured it into ice cold water, extracted with ethyl acetate (400 mL×2), then the organics were dried over anhydrous $Na_2SO_4$. The solvent was distilled off completely to obtain a yellow colored solid as crude product. The product was recrystallized in diisopropylether to obtain pure 4-(4-fluorophenyl)-6-methoxy-2H-chromene-3-carbaldehyde (77 g, 69%).

Step 5: Synthesis of (4-(4-fluorophenyl)-6-methoxy-2H-chromen-3-yl)methanol

Methanol (50 mL) was added to a solution of 4-(4-fluorophenyl)-6-methoxy-2H-chromene-3-carbaldehyde (100 g, 0.35 mol) in toluene (400 mL) at 25-30° C. The reaction was cooled to 5-10° C. and sodium borohydride was added into the reaction mass at 5-10° C. in small portions over a period of 10 min. After completion of the addition, the reaction was allowed to warm to RT and stirred over a period of 1 h. After this time, 200 mL of water was added to the mixture and the organic layer was washed with brine, dried over anhydrous $Na_2SO_4$ and concentrated in vacuo to give the title compound (4-(4-fluorophenyl)-6-methoxy-2H-chromen-3-yl)methanol (90 g, 90%).

Step 6: Synthesis of 3-(chloromethyl)-4-(4-fluorophenyl)-6-methoxy-2H-chromene

Thionyl chloride (33 mL) was added to a mixture of (4-(4-fluorophenyl)-6-methoxy-2H-chromen-3-yl)methanol (90 g, 0.31 mmol) in toluene (200 mL) at 5-10° C. and then stirred at 5-10° C. for 1 h. The reaction was quenched with water (2500 mL) and stirred for 15 min and organic layer dried over anhydrous $Na_2SO_4$ and concentrated in vacuo to obtain 3-(chloromethyl)-4-(4-fluorophenyl)-6-methoxy-2H-chromene as a light brown colored gummy mass (83 g, 88%).

Step 7: Synthesis of 1-((4-(4-fluorophenyl)-6-methoxy-2H-chromen-3-yl)methyl)pyrrolidine Pyrrolidine (33 mL) was added to a solution of 3-(chloromethyl)-4-(4-fluorophenyl)-6-methoxy-2H-chromene (100 g, 0.33 mmol) in diisopropylether (400 mL) and the mixture was cooled to 5-10° C. Anhydrous potassium carbonate (138 g, 1.0 mol) was added at 5-10° C. and the reaction was then heated to 55-60° C. for 1 h. After this time, reaction mass was cooled to 25-30° C. and filtered. The clear filtrate was washed with water (250 mL) and the organic layer was dried over anhydrous sodium sulfate and concentrated to obtain a light brown colored gummy mass of 1-((4-(4-fluorophenyl)-6-methoxy-2H-chromen-3-yl)methyl)pyrrolidine (100 g, 89%).

Step 8: Synthesis of 1-((4-(4-fluorophenyl)-6-methoxy-2H-chromen-3-yl)methyl)pyrrolidine hydrochloride HCl in diisopropylether (250 mL) was added to a solution of 1-((4-(4-fluorophenyl)-6-methoxy-2H-chromen-3-yl)methyl)pyrrolidine (100 g, 0.29 mol) in diisopropylether (400 mL) between 5-10° C. in a drop wise manner over a period of 1 h, followed by stirring for 30 min at 5-10° C. The precipitated solid was filtered and dried under vacuum at 40-45° C. to yield 1-((4-(4-fluorophenyl)-6-methoxy-2H-chromen-3-yl)methyl)pyrrolidine hydrochloride (100 g, 91%).

Step 9: Synthesis of 4-(4-fluorophenyl)-3-(pyrrolidin-1-ylmethyl)-2H-chromen-6-ol Neat $BBr_3$ (100 g, 38 mL, 0.4 mol) was added to a solution of 1-((4-(4-fluorophenyl)-6-methoxy-2H-chromen-3-yl)methyl)pyrrolidine hydrochloride (100 g, 0.27 mol) in dry DCM (1500 mL) at 0-10° C. and after completion of the addition the mixture was stirred at RT for 16 h. The DCM layer was decanted to separate the gummy product mass. The product was quenched with methanol and diluted with water to precipitate out the product. The precipitated solid was filtered and suck dried to yield 4-(4-fluorophenyl)-3-(pyrrolidin-1-ylmethyl)-2H-chromen-6-ol (75 g, 86%).

Step 10: Synthesis of 3-((4-(4-fluorophenyl)-3-(pyrrolidin-1-ylmethyl)-2H-chromen-6-yl)oxy)propanenitrile DMF (125 mL) and potassium carbonate (25.5 g, 185.0 mmol) were added to a solution of 4-(4-fluorophenyl)-3-(pyrrolidin-1-ylmethyl)-2H-chromen-6-ol (25 g, 61.7 mmol) in acrylonitrile (250 mL). The mixture was heated to 80-85° C. for 24 h. After this time, the reaction mixture was concentrated in vacuo. The resulting residue was quenched with water and extracted with ethyl acetate (300 mL). The organic layer was dried over anhydrous sodium sulfate and concentrated to obtain a light brown colored gummy mass which was further purified by column chromatography to yield 3-((4-(4-fluorophenyl)-3-(pyrrolidin-1-ylmethyl)-2H-chromen-6-yl)oxy)propanenitrile as a light brown solid (11 g, 47%).

Step 11: Synthesis of 3-((4-(4-fluorophenyl)-3-(pyrrolidin-1-ylmethyl)-2H-chromen-6-yl)oxy)propanoic acid hydrochloride Concentrated HCl (1.0 L) was added to 3-((4-(4-fluorophenyl)-3-(pyrrolidin-1-ylmethyl)-2H-chromen-6-yl)oxy)propanenitrile (100 g, 26 mol) and the reaction was heated to 95-100° C. for 4 h. The reaction was then cooled to RT and stirred for 3 h. The Precipitated solids were filtered and suck dried to obtain crude I-33 (60 g) with HPLC purity 92-95% a/a.

Example 25: CD3 Mediated Phosphorylation of ZAP70 in Jurkat Cells

Inhibition of CD3 mediated phosphorylation of ZAP70 in Jurkat cells was measured by a cellular based Homogeneous Time-Resolved Fluorescence (HTRF) assay utilizing a Total ZAP-70 HTRF kit. Materials utilized in the HTRF assay are summarized in Table 4, below.

TABLE 4 pZAP70 Inhibition Materials

| Materials | Catalog Number | Supplier |
|---|---|---|
| RPMI 1640 cell culture media | R6504 | Sigma-Aldrich |
| PBS | 10010031 | Thermo Fisher Scientific |
| BSA | B6917 | Sigma-Aldrich |
| ProxiPlate-384 Plus Shallow Well Microplates (White) | 6008281 | PerkinElmer |
| CD3 monoclonal antibody (OKT3) functional grade | 16-0037-81 | Thermo Fisher Scientific |
| Histopaque-1077 | 10771 | Sigma-Aldrich |
| Total ZAP-70 HTRF kit | 64ZATPEG | Cisbio |
| HBSS | 14025092 | Thermo fisher |

Briefly, Jurkat cells (~1.3×10$^6$ cells/mL) were harvested on the day of experimentation. Cells were washed with PBS and resuspended in Assay Buffer (RPMI 1640 media plus 10% FBS) and counted.

Cell count was performed by first diluting 10 µL of cells with 90 µL of media/PBS (1:10). Twenty (20) µL of the diluted cell suspension was then added to 20 µL of trypan blue solution (1:1) and mixed carefully to avoid aerosol formation. The cell culture mixture was then loaded on a Hemocytometer until the area under the coverslip was sufficiently full and the suspension was allowed to settle in the Haemocytometer for at least 10 minutes before counting. Viable cells (clear) and dead cells (blue) were counted in four (4) corners 1 mm squares, including cells that touched the tope line or vertical perimeter line of any corner square, but not the cells that touched either the bottom line or right-vertical perimeter line of any corner square.

To Calculate the number of viable cells/mL:

Cells/mL=Cells in all four squares×10×2×10$^4$/4

10$^4$=Volume conversion factor to 1 mL; 10=dilution factor of cell suspension; 2=Dilution factor with trypan blue Total cell count=cells/mL×Total volume (mL) of cell suspension % Cell viability=(Number of viable cells counted/total number of cells counted (viable+dead))×100

Jurkat cells were seeded in Assay media at a total volume of 4 µL/well (40K cells/well) in a 384-low volume white flat bottom plate. The cells were then incubated at 37° C./5% CO$_2$ for 30 minutes. The cells were then treated in duplicate with test compounds (3×) and reference compounds (3×) in a total volume of 4 µL, respectively. A compound dilution scheme is exemplified in FIG. 1.

The plate was then transferred to an incubator maintained at 37° C./5% CO$_2$ for 2 minutes. Following incubation, cells were stimulated with 20 µg/mL of anti-CD3 antibody (1 mg/mL stock) and assay media was used to bring the total well volume 4 µL/well. The plate was then transferred to the incubator maintained at 37° C./5% CO$_2$ for 2.5 minutes. Following incubation, 4 µL of lysis buffer (4×) provided in the kit was added to each well. The plate was then incubated at RT for 1 hour with gentle shaking. Following incubation, 4 µL of detection mix was added to each well and the plate was sealed with a plate sealer and left overnight at RT in the dark.

The Envision reader was set-up for Eu$^{3+}$ cryptate and fluorescence emission was read at two different wavelengths (620 nm and 665 nm).

Excitation filter: UV2(TRF) 320 nm
Emission filter: 665 nm
2$^{nd}$ Emission filter: Europium 615 nm
Measurement height (mm): 6.5
Excitation light (%): 100
Delay (µs): 50
Window time (µs): 400
Time between flashes (µs): 2000
Number of flashes: 100
Number of flashes for 2$^{nd}$ detector: 100

The data is represented by the signal form the two wavelengths:

$$\frac{\text{Signal}_{665\,nm}}{\text{Signal}_{620\,nm}} \times 10^4$$

The ratio of the signal is calculated for each individual well:

$$\frac{\text{Standard Deviation}}{\text{Mean Ratio}} \times 100$$

The data was plotted using Graph Pad Prism. The significance between untreated vs. treated groups was assessed by One-way ANOVA and Bonferroni posttest comparing all columns in the graph.

ZAP70 $IC_{50}$ results are shown in Table 6 for select compounds of the invention. The compound numbers correspond to the compound numbers in Table 1. Compounds having a designation of "A" provide an $IC_{50}$ of less than one nanomolar (<1 nm). Compounds having a designation of "B" provide an $IC_{50}$ of between one and less than ten nanomolar (1 nm≤x<10 nm). Compounds having a designation of "C" provide an $IC_{50}$ of between ten and less than fifty nanomolar (10 nm≤x<50 nm). Compounds having a designation of "D" provide an $IC_{50}$ of greater than fifty nanomolar or greater (≥50 nm). "ND" indicates not determined.

ZAP70 percent maximum inhibition results are shown in Table 7 for select compounds of the invention. The compound numbers correspond to the compound numbers in Table 1. Compounds having a designation of "A" provide a percent maximum inhibition of greater than fifty percent (>50%). Compounds having a designation of "B" provide a percent maximum inhibition of between fifty and greater than forty percent (50%≥x>40%). Compounds having a designation of "C" provide a percent maximum inhibition of between forty and greater than thirty percent (40%≥x>30%). Compounds having a designation of "D" provide a percent maximum inhibition of thirty percent or less (≤30%).

TABLE 6 pZAP70 Inhibition $IC_{50}$

| Compound # | $IC_{50}$ (nM) |
| --- | --- |
| I-3 | A |
| I-11 | B |
| I-12 | ND |
| I-13 | B |
| I-14 | A |
| I-15 | A |
| I-16 | A |
| I-19 | B |
| I-20 | A |
| I-21 | B |
| I-22 | ND |
| I-23 | B |
| I-24 | B |
| I-27 | D |
| I-30 | B |
| I-33 | B |
| I-34 | A |
| I-35 | B |
| I-36 | A |
| I-37 | B |
| I-39 | B |
| I-40 | B |
| I-41 | B |
| I-42 | D |
| I-43 | C |
| I-44 | B |
| I-58 | D |
| I-59 | A |
| I-61 | B |
| I-62 | B |
| I-63 | B |
| I-64 | B |
| I-65 | A |
| I-66 | B |
| I-67 | C |
| I-68 | A |
| I-69 | B |
| I-70 | B |
| I-76 | B |
| I-76 | B |
| I-79 | B |
| I-80 | B |
| I-81 | B |

TABLE 7 pZAP70 Inhibition - Maximum Percent Inhibition

| Compound # | % Inhibition |
| --- | --- |
| I-3 | D |
| I-11 | D |
| I-12 | D |
| I-13 | B |
| I-14 | C |
| I-15 | C |
| I-16 | C |
| I-19 | A |
| I-20 | B |
| I-21 | B |
| I-22 | D |
| I-23 | A |
| I-24 | B |
| I-27 | D |
| I-30 | B |
| I-33 | A |
| I-34 | C |
| I-35 | D |
| I-36 | B |
| I-37 | C |
| I-39 | D |
| I-40 | C |
| I-41 | C |
| I-42 | D |
| I-43 | C |
| I-44 | C |
| I-58 | C |
| I-59 | C |
| I-61 | B |
| I-62 | C |
| I-63 | C |
| I-64 | C |
| I-65 | A |
| I-66 | A |
| I-67 | A |
| I-68 | A |
| I-69 | A |
| I-70 | B |
| I-76 | A |
| I-76 | B |
| I-79 | A |
| I-80 | A |
| I-81 | A |

We claim:
1. A compound of Formula VIII:

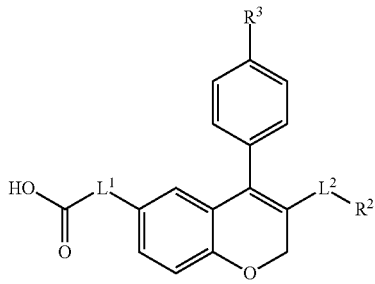

or a pharmaceutically acceptable salt thereof, wherein:
$R^2$ is R, halogen, —C(O)N(R)$_2$, or —N(R)$_2$;
$R^3$ is halogen, —NO$_2$, or $C_{1-4}$ aliphatic substituted with 1-9 halogens;
each R is independently hydrogen or an optionally substituted group selected from $C_{1-6}$ aliphatic, a 3-8 member saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur,
or two R on the same nitrogen are taken together with their intervening atoms to form an optionally substituted 5-6 membered heterocyclic ring having 0-1 heteroatoms in addition to the nitrogen attached thereto wherein such heteroatom is oxygen, nitrogen, or sulfur;
$L^1$ is a covalent bond or a $C_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —CH(R)—, —C(F)$_2$—, —N(R)—, —C(O)N(R)—, —RNC(O)—, —OC(O)N(R)—, —N(R)C(O)N(R)—, or -Cy-;
$L^2$ is a $C_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —CH(R)—, —C(F)$_2$—, —N(R)—, —C(O)N(R)—, —RNC(O)—, —OC(O)N(R)—, or —N(R)C(O)N(R)—; and
each Cy is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur.

2. The compound according to claim 1, or a pharmaceutically acceptable salt thereof, wherein $R^2$ is —N(R)$_2$ wherein the two R groups on the nitrogen are taken together with their intervening atoms to form an optionally substituted 5-6 membered heterocyclic ring having 0-1 heteroatoms in addition to the nitrogen attached thereto wherein such heteroatom is oxygen, nitrogen, or sulfur.

3. The compound according to claim 2, or a pharmaceutically acceptable salt thereof, wherein $R^2$ is

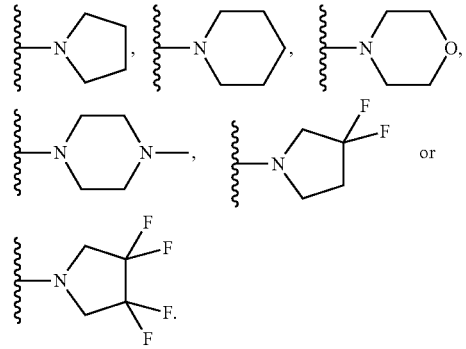

4. The compound according to claim 1, or a pharmaceutically acceptable salt thereof, wherein $R^3$ is $C_{1-4}$ aliphatic substituted with 1-9 halogens.

5. The compound according to claim 1, or a pharmaceutically acceptable salt thereof, wherein $R^3$ is halogen.

6. The compound according to claim 5, or a pharmaceutically acceptable salt thereof, wherein $R^3$ is F.

7. The compound according to claim 4, or a pharmaceutically acceptable salt thereof, wherein $R^3$ is selected from

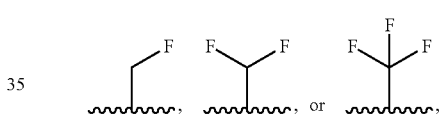

or a pharmaceutically acceptable salt thereof.

8. The compound according to claim 1, or a pharmaceutically acceptable salt thereof, wherein $L^1$ is a $C_{1-4}$ bivalent straight or branched saturated or unsaturated hydrocarbon chain wherein 1-2 methylene units of the chain are independently and optionally replaced with —O—, —C(O)—, —C(O)O—, —OC(O)—, —C(S)—, —C(R)$_2$—, —CH(R)—, —C(F)$_2$—, —N(R)—, —C(O)N(R)—, —RNC(O)—, —OC(O)N(R)—, —N(R)C(O)N(R)—, or -Cy-.

9. The compound according to claim 8, or a pharmaceutically acceptable salt thereof, wherein $L^1$ is a $C_{1-4}$ bivalent straight or branched saturated or unsaturated hydrocarbon chain wherein 1-2 methylene units of the chain are independently and optionally replaced with —O—, —C(R)$_2$—, —C(O)N(R)—, or —RNC(O)—.

10. The compound according to claim 8, or a pharmaceutically acceptable salt thereof, wherein $L^1$ is a $C_{1-4}$ bivalent straight or branched saturated or unsaturated hydrocarbon chain wherein 1-2 methylene unit of the chain is replaced with —O— or —C(O)—.

11. The compound according to claim 1, or a pharmaceutically acceptable salt thereof, wherein $L^1$ is

-continued

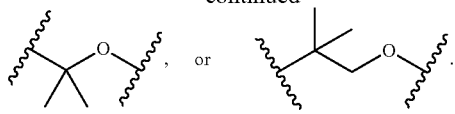

12. The compound according to claim 1, or a pharmaceutically acceptable salt thereof, wherein $L^2$ is a $C_{1-4}$ bivalent straight or branched saturated or unsaturated hydrocarbon chain wherein 1 methylene unit of the chain is optionally replaced with —O—, —C(O)—, —C(O)O—, or —OC(O)—.

13. The compound according to claim 12, or a pharmaceutically acceptable salt thereof, wherein $L^2$ is —C(O)—, —CH$_2$—, or —(CH$_2$)$_2$—.

14. The compound according to claim 1, which is a compound of Formula IX:

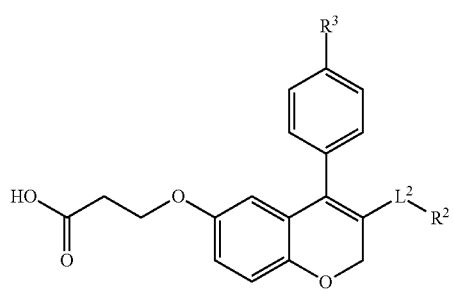

or a pharmaceutically acceptable salt thereof.

15. The compound according to claim 5, which is a compound of Formula X:

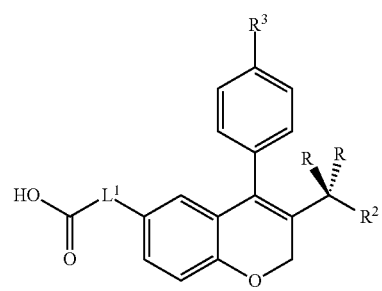

or a pharmaceutically acceptable salt thereof.

16. The compound according to claim 1, which is a compound of Formulae XI-a or XI-b:

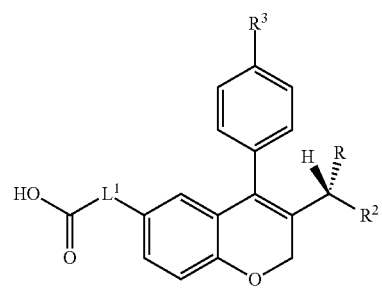

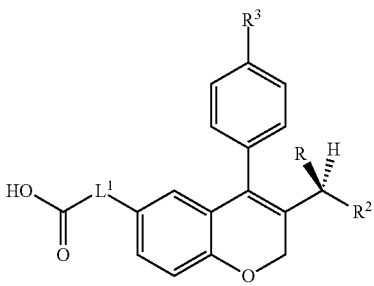

or a pharmaceutically acceptable salt thereof.

17. The compound according to claim 1, selected from the group consisting of:

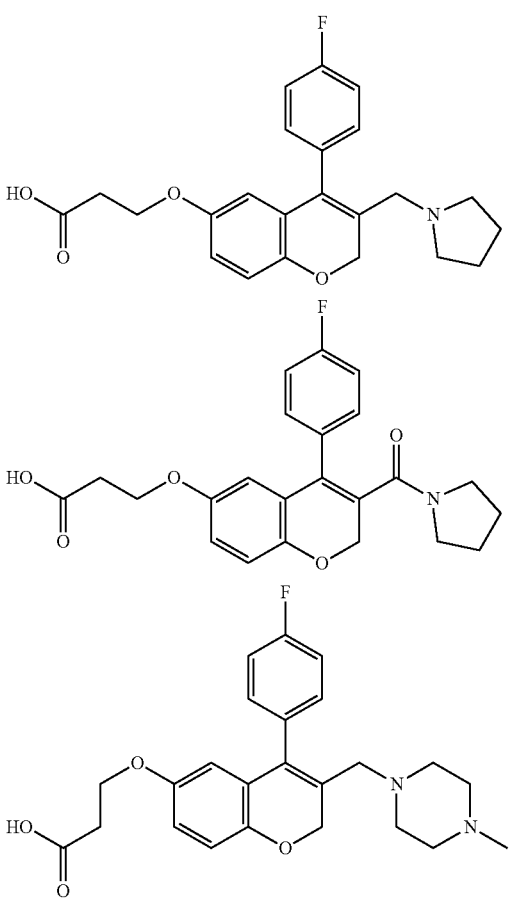

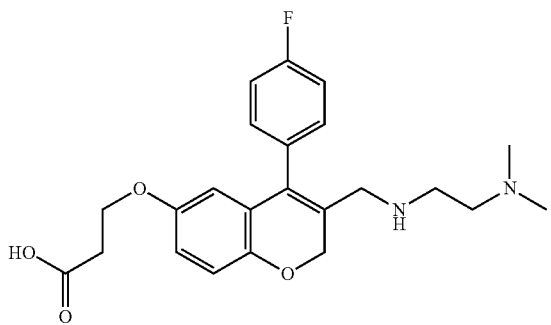

123
-continued
124
-continued
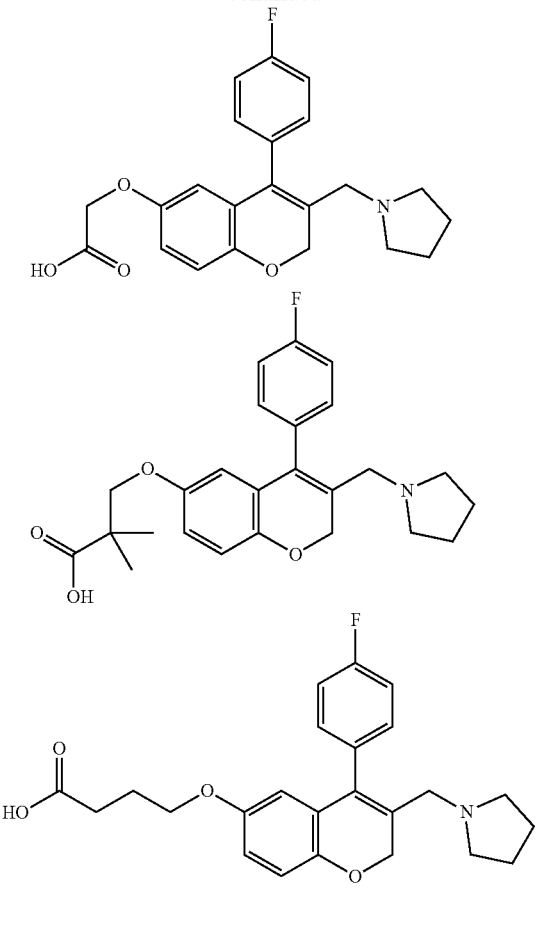
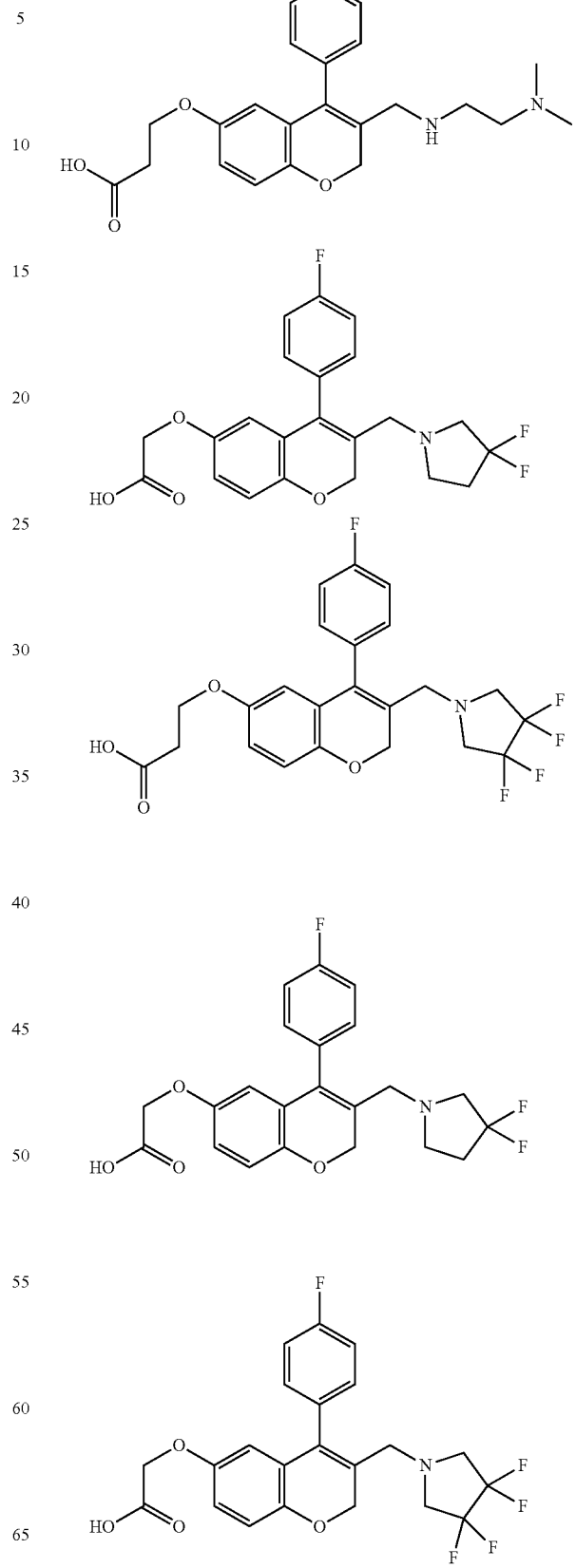

125
-continued
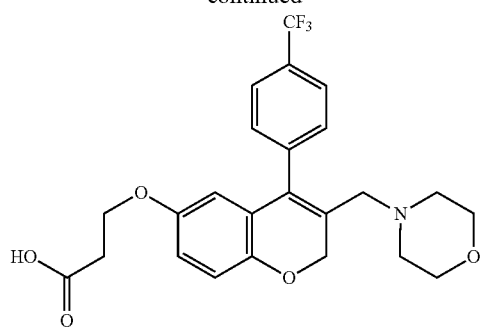
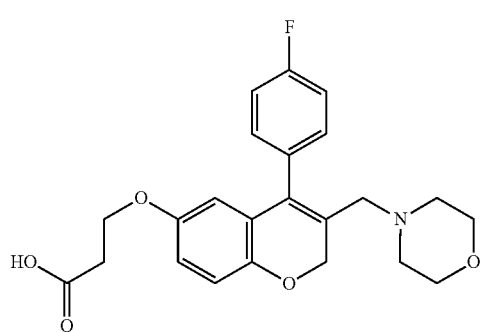
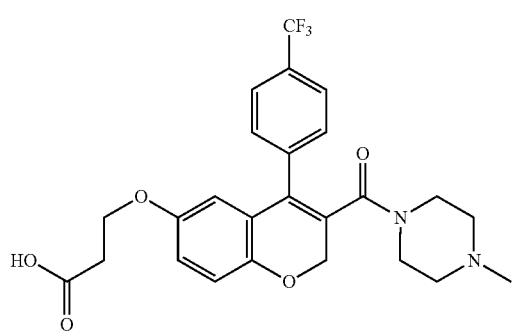
126
-continued
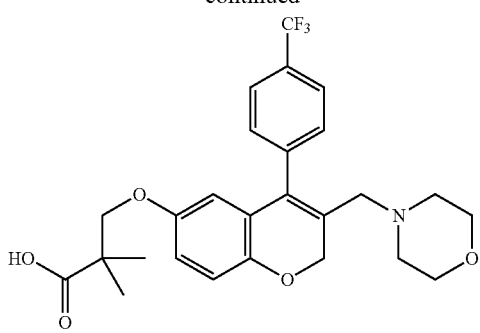
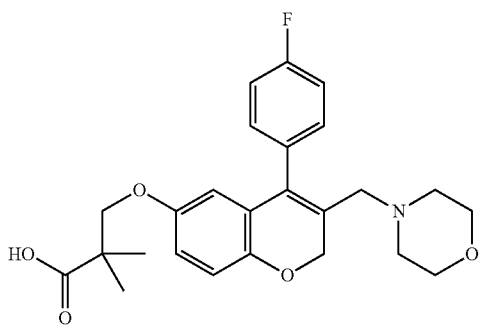
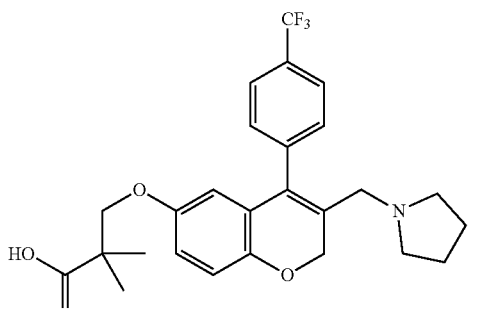
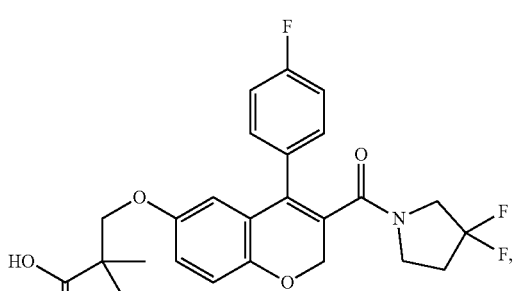
or a pharmaceutically acceptable salt thereof.
18. A pharmaceutically acceptable composition comprising the compound of claim 1, or a pharmaceutically acceptable salt thereof, and a pharmaceutically acceptable excipient, adjuvant, or vehicle.

19. The compound according to claim 1, selected from the group consisting of:
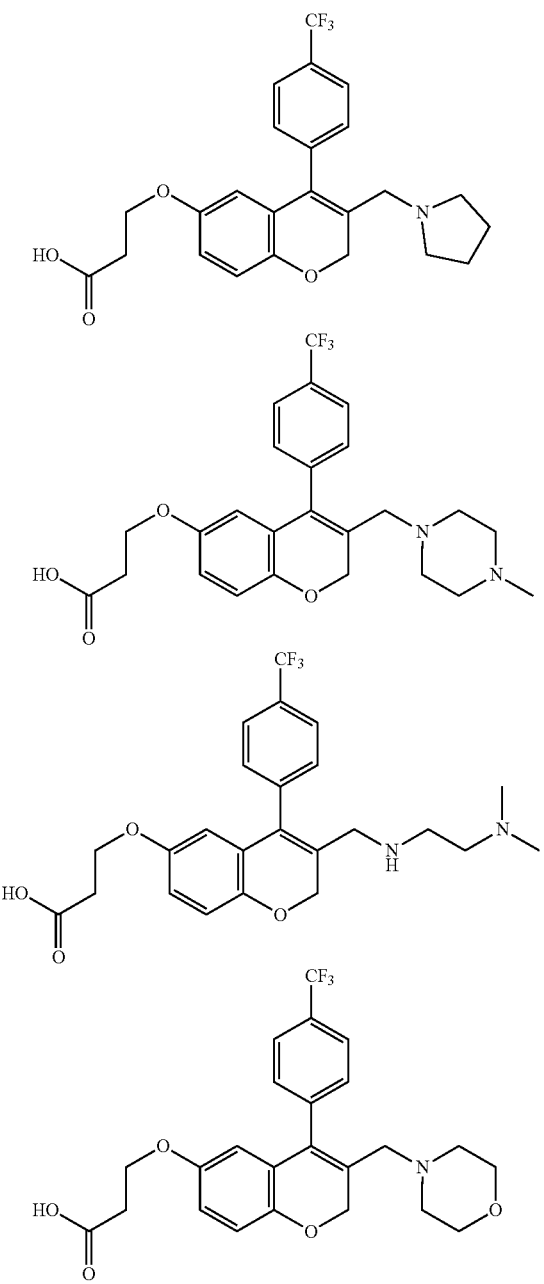
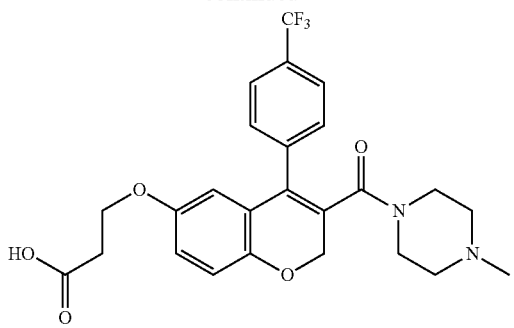
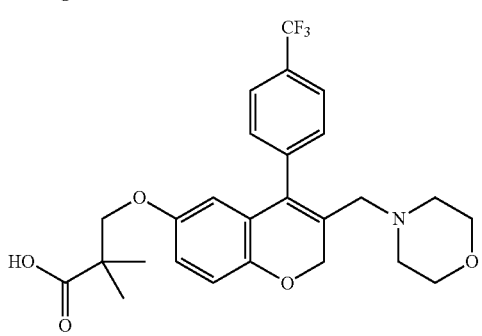
and
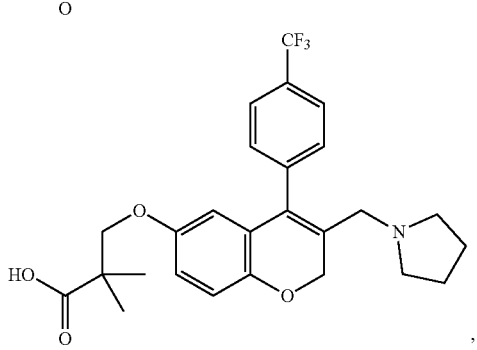
,
or a pharmaceutically acceptable salt thereof.
20. The compound according to claim 1, wherein $R^2$ is or
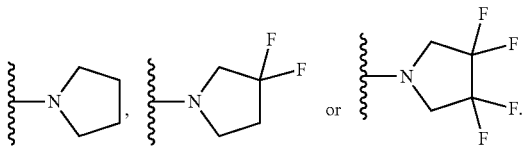
* * * * *